United States Patent
Mohammadi

(10) Patent No.: US 12,227,777 B2
(45) Date of Patent: Feb. 18, 2025

(54) SOLUBLE ALPHA-KLOTHO PROTEINS, PROTEIN FRAGMENTS, AND USES THEREOF

(71) Applicant: New York University, New York, NY (US)

(72) Inventor: Moosa Mohammadi, Scarsdale, NY (US)

(73) Assignee: NEW YORK UNIVERSITY, New York, NY (US)

( * ) Notice: Subject to any disclaimer, the term of this patent is extended or adjusted under 35 U.S.C. 154(b) by 1228 days.

(21) Appl. No.: 16/961,525

(22) PCT Filed: Jan. 11, 2019

(86) PCT No.: PCT/US2019/013282
§ 371 (c)(1),
(2) Date: Jul. 10, 2020

(87) PCT Pub. No.: WO2019/140250
PCT Pub. Date: Jul. 18, 2019

(65) Prior Publication Data
US 2021/0054355 A1    Feb. 25, 2021

Related U.S. Application Data

(60) Provisional application No. 62/616,945, filed on Jan. 12, 2018.

(51) Int. Cl.
*A61K 38/00*   (2006.01)
*C12N 9/24*   (2006.01)

(52) U.S. Cl.
CPC ............ *C12N 9/2402* (2013.01); *A61K 38/00* (2013.01); *C12Y 302/01031* (2013.01)

(58) Field of Classification Search
CPC .................. C12N 9/2402; A61K 38/00; C12Y 302/01031
See application file for complete search history.

(56) References Cited

U.S. PATENT DOCUMENTS

| | | | |
|---|---|---|---|
| 8,889,426 B2 | 11/2014 | Mohammadi et al. |
| 8,889,621 B2 | 11/2014 | Mohammadi et al. |
| 8,999,929 B2 | 4/2015 | Mohammadi et al. |
| 9,272,017 B2 | 3/2016 | Mohammadi et al. |
| 9,464,126 B2 | 10/2016 | Mohammadi et al. |
| 9,474,785 B2 | 10/2016 | Mohammadi et al. |
| 9,475,856 B2 | 10/2016 | Mohammadi et al. |

(Continued)

OTHER PUBLICATIONS

International Search Report and Written Opinion for corresponding PCT International Application No. PCT/US19/13282 (mailed Jun. 17, 2019).

(Continued)

*Primary Examiner* — David W Berke-Schlessel
*Assistant Examiner* — Trent R Clarke
(74) *Attorney, Agent, or Firm* — Troutman Pepper Locke, LLP (Rochester)

(57) ABSTRACT

Disclosed herein are modified soluble α-Klotho proteins and isolated fragments of wildtype soluble α-Klotho protein. Also disclosed are pharmaceutical compositions including the modified soluble α-Klotho proteins and/or isolated fragments of soluble α-Klotho protein and methods of their use in treating a subject.

8 Claims, 31 Drawing Sheets
Specification includes a Sequence Listing.

(56) References Cited

U.S. PATENT DOCUMENTS

| | | |
|---|---|---|
| 9,550,820 B2 | 1/2017 | Mohammadi et al. |
| 9,657,075 B2 | 5/2017 | Mohammadi et al. |
| 9,907,830 B2 | 3/2018 | Mohammadi et al. |
| 9,926,355 B2 | 3/2018 | Mohammadi et al. |
| 9,926,356 B2 | 3/2018 | Mohammadi et al. |
| 10,174,090 B2 | 1/2019 | Mohammadi et al. |
| 10,364,278 B2 | 7/2019 | Mohammadi et al. |
| 10,464,979 B2 | 11/2019 | Mohammadi et al. |
| 10,632,180 B2 * | 4/2020 | Dubal .................... A61P 25/28 |
| 10,633,424 B2 | 4/2020 | Mohammadi et al. |
| 10,654,909 B2 * | 5/2020 | Guo ....................... A61P 19/10 |
| 10,703,788 B2 | 7/2020 | Mohammadi et al. |
| 2015/0079065 A1 | 3/2015 | Wolf et al. |

OTHER PUBLICATIONS

Goetz & Mohammadi, "Exploring Mechanisms of FGF Signaling Through the Lens of Structural Biology," Nat. Rev. Mol. Cell Biol. 14(3):166-180 (2013).

Chen et al., "α-Klotho is a Non-Enzymatic Molecular Scaffold for FGF23 Hormone Signaling," Nature 553(7689): 461-466 (2018).

* cited by examiner

A

B

C

A

B

E

F

G

C

D

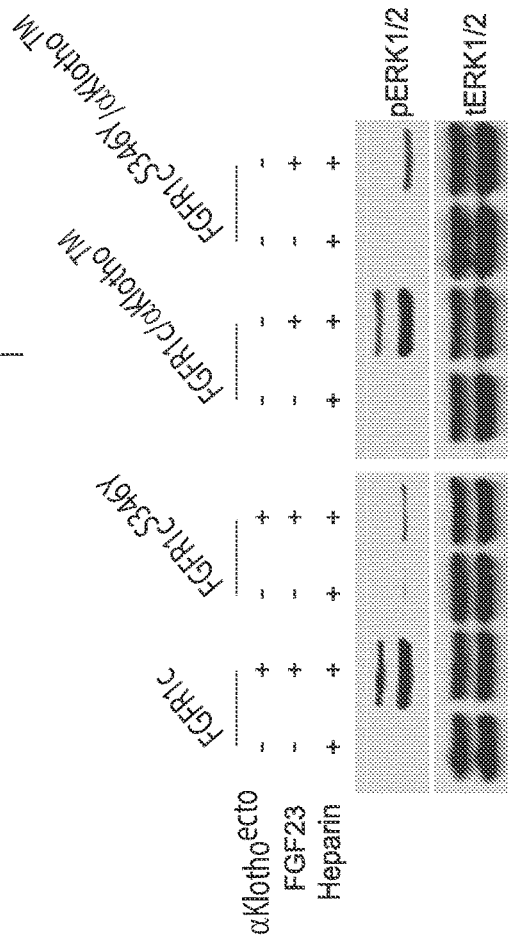
FIG. 9A
FIG. 9B
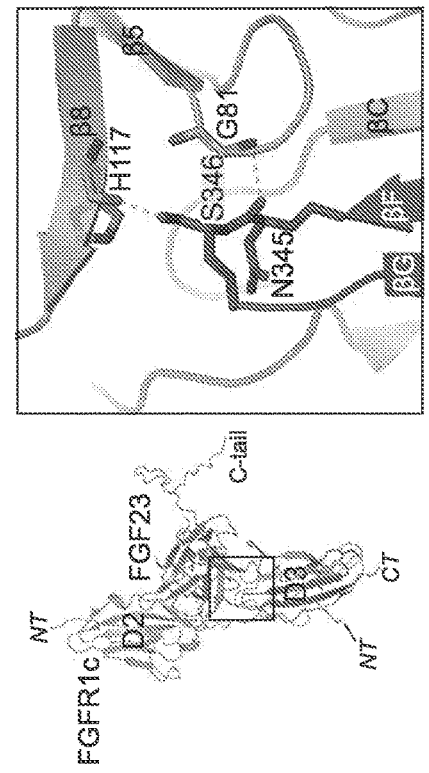
FIG. 9C

FIG. 10A

```
αKlotho 693 ---------------MYSAGHNLL KAHALAWHVY NEKFRHAQNG KISTALQAEN EPAEGTSQK EVAERLLE HIGWLAEPI EGSGDYPWM RDWLMQRN-- -----NFLLPYF TEDEKKLIQG
βKlotho 697 LSDIYNRSGN DFYCAHNLLL VAHALAWRLY DRQFRPSQRG AVSLSLHADM AEPANPYADS AEPANPYADS HWRAAERFLQ FEIAWFAEPL FKHGDYPAAM REYTASKHRR QLSSSALPRL TEARRLLLKG
                      *** *****  ******     *****     ***  *****    *   **** *   ******  **        *  **        ***       *

αKlotho 800 TFDFLALSHY TTILVSEKT IPENYLE VKMDVFNDTG RNLSPSWAVP NGLRKVLNWL KKKYGDLPMY ITENGIDDA EDDQLRYY VMQNVIEAL KAHILDGINL CGYTAYSFN
βKlotho 817 TVDFCALNHF TLRFVMHEQL AGSRYDSDRD IQFLQDITRL SSFTRLAVIP WGVRKLLRWV RRNYGDMDIY ITASGIDDQA -LEDDRLRKY YLGKYLQEVL KAYLIDKVRI KGYYAFKLAE
               **  *    *       *   *      *       ***       *       *   *  *  ** *    * ****   *   *   *      * *  * * juxtamembrane                               transmembrane
αKlotho 920 -RTAPREGLY IPK ASMKHYRKIT DSWGFGEET LERFC-PEEF TVCEGSFFH TRKGLLQAFIA FLFFASTISL SLIFYYSKKG RRSYK
βKlotho 936 EKSFRPRGFT ----TSDFYAK SSTQFYNKVI SSRGPFFTAS SSRCSQTQEN TECTVCLFLV QKK-PLIFLG CCFFSTIVIL LSIIAIFQRQK RREFWKAKNL QHIPLKKCGR VVS
            ****                *        *      ***    *                **    **     *     *       *   **         *      *
```

FIG. 14 (cont.)

```
         βN               β1                    β2               β3                β4
FGF23  25         ASPLLGSSWG GIHLMTATA RN--SYLQI HKNGHVDGAP MQTIYSALMI
FGF21  29    HPIPDS SPLLQFGGQV RQRYLYTDDA QQ-TEAHLEI REDGTVGGAA DQSPESLLQL
FGF19  23 RPLAFSDAGP HVHYGWDPI RLRHLYTSGP HGLSSCFLRI RADGVVDCAR GQSAHSLLEI
                                    *  *         *      **  *

β5               β6                              β7
FGF23  76    RSDAEFVI IGVSRVLC MDFERGNIEGS HYEDPENCRF QHILENGYD VYHSPQYHFL
FGF21  84 KALKPGVIQI LGVKTSRFLC QRPDGALYGS LHFDPEACSF RELLLEDGYN VYQSEAHGLP
FGF19  83 KAVALRTVAI KGVHSVRYLC MGADGKMQGL LQYSEEDCAF EEEIRPDGYN VYRSEKHRLP
                *          *  *              *  *        *  **

βp2
FGF23  136 VSLGRAKRAF LP-GMNPPPY SQFSRNEI PHLHTWTIP RHIRSAEDD SEHLQNIYI
FGF21  144 LHLPGNKSPH RD--PAPRGP ARFLPLPGLP PALPEPPGIL APQPPDVGSS DPLSMVG---
FGF19  143 VSLSSAKQRQ LYKNRGFLPL SHFLPMLPMV PEEPEDLRGH LESDMFSSPL ETDSMDPFGL
                                *                  *

FGF23  195 MAPRSPAPA PAPA SCSQELPSAE DNSPMASDPL GVVRGGRVNT HAGGTGPEGC RPFAKFI
FGF21  199 ---PSQGRSP SYAS
FGF19  203 VTGLEAVRSP SFEK
                 *     *
```

FIG. 15A

SEQUENCE LISTING

<160> NUMBER OF SEQ ID NOS: 29

<210> SEQ ID NO 1
<211> LENGTH: 981
<212> TYPE: PRT
<213> ORGANISM: Artificial Sequence
<220> FEATURE:
<223> OTHER INFORMATION: Wildtype Human alpha-Klotho

<400> SEQUENCE: 1

```
Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Arg Arg Leu Arg
                20                  25                  30

Ala Glu Pro Gly Asp Gly Ala Gln Thr Trp Ala Arg Val Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
                100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
        130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
                180                 185                 190

His Trp Asp Leu Pro Gln Arg Leu Gln Asp Ala Tyr Gly Gly Trp Ala
            195                 200                 205
```

-continued

```
Asn Arg Ala Leu Ala Asp His Phe Arg Asp Tyr Ala Glu Leu Cys Phe
210                 215                 220
Arg His Phe Gly Gly Gln Val Lys Tyr Trp Ile Thr Ile Asp Asn Pro
225                 230                 235                 240
Tyr Val Val Ala Trp His Gly Tyr Ala Thr Gly Arg Leu Ala Pro Gly
            245                 250                 255
Ile Arg Gly Ser Pro Arg Leu Gly Tyr Leu Val Ala His Asn Leu Leu
            260                 265                 270
Leu Ala His Ala Lys Val Trp His Leu Tyr Asn Thr Ser Phe Arg Pro
            275                 280                 285
Thr Gln Gly Gly Gln Val Ser Ile Ala Leu Ser Ser His Trp Ile Asn
290                 295                 300
Pro Arg Arg Met Thr Asp His Ser Ile Lys Glu Cys Gln Lys Ser Leu
305                 310                 315                 320
Asp Phe Val Leu Gly Trp Phe Ala Lys Pro Val Phe Ile Asp Gly Asp
            325                 330                 335
Tyr Pro Glu Ser Met Lys Asn Asn Leu Ser Ser Ile Leu Pro Asp Phe
            340                 345                 350
Thr Glu Ser Glu Lys Lys Phe Ile Lys Gly Thr Ala Asp Phe Phe Ala
            355                 360                 365
Leu Cys Phe Gly Pro Thr Leu Ser Phe Gln Leu Leu Asp Pro His Met
370                 375                 380
Lys Phe Arg Gln Leu Glu Ser Pro Asn Leu Arg Gln Leu Leu Ser Trp
385                 390                 395                 400
Ile Asp Leu Glu Phe Asn His Pro Gln Ile Phe Ile Val Glu Asn Gly
            405                 410                 415
Trp Phe Val Ser Gly Thr Thr Lys Arg Asp Asp Ala Lys Tyr Met Tyr
            420                 425                 430
Tyr Leu Lys Lys Phe Ile Met Glu Thr Leu Lys Ala Ile Lys Leu Asp
            435                 440                 445
Gly Val Asp Val Ile Gly Tyr Thr Ala Trp Ser Leu Met Asp Gly Phe
450                 455                 460
Glu Trp His Arg Gly Tyr Ser Ile Arg Arg Gly Leu Phe Tyr Val Asp
465                 470                 475                 480
Phe Leu Ser Gln Asp Lys Met Leu Leu Pro Lys Ser Ser Ala Leu Phe
            485                 490                 495
Tyr Gln Lys Leu Ile Glu Lys Asn Gly Phe Pro Leu Pro Glu Asn
            500                 505                 510
Gln Pro Leu Glu Gly Thr Phe Pro Cys Asp Phe Ala Trp Gly Val Val
            515                 520                 525
Asp Asn Tyr Ile Gln Val Asp Thr Thr Leu Ser Gln Phe Thr Asp Leu
530                 535                 540
Asn Val Tyr Leu Trp Asp Val His His Ser Lys Arg Leu Ile Lys Val
545                 550                 555                 560
Asp Gly Val Val Thr Lys Lys Arg Lys Ser Tyr Cys Val Asp Phe Ala
            565                 570                 575
Ala Ile Gln Pro Gln Ile Ala Leu Leu Gln Glu Met His Val Thr His
            580                 585                 590
Phe Arg Phe Ser Leu Asp Trp Ala Leu Ile Leu Pro Leu Gly Asn Gln
            595                 600                 605
Ser Gln Val Asn His Thr Ile Leu Gln Tyr Tyr Arg Cys Met Ala Ser
610                 615                 620
Glu Leu Val Arg Val Asn Ile Thr Pro Val Val Ala Leu Trp Gln Pro
```

```
            625                 630                 635                 640
        Met Ala Pro Asn Gln Gly Leu Pro Arg Leu Leu Ala Arg Gln Gly Ala
                        645                 650                 655

Trp Glu Asn Pro Tyr Thr Ala Leu Ala Phe Ala Glu Tyr Ala Arg Leu
                        660                 665                 670

Cys Phe Gln Glu Leu Gly His Val Lys Leu Trp Ile Thr Met Asn
                    675                 680                 685

Glu Pro Tyr Thr Arg Asn Met Thr Tyr Ser Ala Gly His Asn Leu Leu
                    690                 695                 700

Lys Ala His Ala Leu Ala Trp His Val Tyr Asn Glu Lys Phe Arg His
        705                 710                 715                 720

Ala Gln Asn Gly Lys Ile Ser Ile Ala Leu Gln Ala Asp Trp Ile Glu
                        725                 730                 735

Pro Ala Cys Pro Phe Ser Gln Lys Asp Lys Glu Val Ala Glu Arg Val
                    740                 745                 750

Leu Glu Phe Asp Ile Gly Trp Leu Ala Glu Pro Ile Phe Gly Ser Gly
                    755                 760                 765

Asp Tyr Pro Trp Val Met Arg Asp Trp Leu Asn Gln Arg Asn Asn Phe
                    770                 775                 780

Leu Leu Pro Tyr Phe Thr Glu Asp Glu Lys Lys Leu Ile Gln Gly Thr
        785                 790                 795                 800

Phe Asp Phe Leu Ala Leu Ser His Tyr Thr Thr Ile Leu Val Asp Ser
                        805                 810                 815

Glu Lys Glu Asp Pro Ile Lys Tyr Asn Asp Tyr Leu Glu Val Gln Glu
                    820                 825                 830

Met Thr Asp Ile Thr Trp Leu Asn Ser Pro Ser Gln Val Ala Val Val
                835                 840                 845

Pro Trp Gly Leu Arg Lys Val Leu Asn Trp Leu Lys Phe Lys Tyr Gly
                850                 855                 860

Asp Leu Pro Met Tyr Ile Ile Ser Asn Gly Ile Asp Asp Gly Leu His
        865                 870                 875                 880

Ala Glu Asp Asp Gln Leu Arg Val Tyr Tyr Met Gln Asn Tyr Ile Asn
                        885                 890                 895

Glu Ala Leu Lys Ala His Ile Leu Asp Gly Ile Asn Leu Cys Gly Tyr
                    900                 905                 910

Phe Ala Tyr Ser Phe Asn Asp Arg Thr Ala Pro Arg Phe Gly Leu Tyr
                    915                 920                 925

Arg Tyr Ala Ala Asp Gln Phe Glu Pro Lys Ala Ser Met Lys His Tyr
        930                 935                 940

Arg Lys Ile Ile Asp Ser Asn Gly Phe Pro Gly Pro Glu Thr Leu Glu
        945                 950                 955                 960

Arg Phe Cys Pro Glu Glu Phe Thr Val Cys Thr Glu Cys Ser Phe Phe
                    965                 970                 975

His Thr Arg Lys Ser
                    980

<210> SEQ ID NO 2
<211> LENGTH: 932
<212> TYPE: PRT
<213> ORGANISM: Artificial Sequence
<220> FEATURE:
<223> OTHER INFORMATION: modified soluble alpha-Klotho protein

<400> SEQUENCE: 2

Met Pro Ala Ser Ala Pro Pro Arg Arg Pro Arg Pro Pro Pro Ser
```

```
1               5                   10                  15
Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Val Ser Arg Pro
                35                  40                  45

Pro Ala Pro Glu Ala Ala Gly Leu Phe Gln Gly Thr Phe Pro Asp Gly
                50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
                100                 105                 110

Ala Pro Ser Pro Leu Gln Pro Ala Thr Gly Asp Val Ala Ser Asp Ser
                115                 120                 125

Tyr Asn Asn Val Phe Arg Asp Thr Glu Ala Leu Arg Glu Leu Gly Val
                130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
                180                 185                 190

His Trp Asp Leu Pro Gln Arg Leu Gln Asp Ala Tyr Gly Gly Trp Ala
                195                 200                 205

Asn Arg Ala Leu Ala Asp His Phe Arg Asp Tyr Ala Glu Leu Cys Phe
                210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
                260                 265                 270

Leu Ala His Ala Lys Val Trp His Leu Tyr Asn Thr Ser Phe Arg Pro
                275                 280                 285

Thr Gln Gly Gly Gln Val Ser Ile Ala Leu Ser Ser His Trp Ile Asn
                290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
                340                 345                 350

Thr Glu Ser Glu Lys Lys Phe Ile Lys Gly Thr Ala Asp Phe Phe Ala
                355                 360                 365

Leu Cys Phe Gly Pro Thr Leu Ser Phe Gln Leu Leu Asp Pro His Met
                370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
                420                 425                 430
```

```
Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
        450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
            515                 520                 525

Asp Gln Pro Gln Ile Ala Leu Leu Gln Glu Met His Val Thr His Phe
        530                 535                 540

Arg Phe Ser Leu Asp Trp Ala Leu Ile Leu Pro Leu Gly Asn Gln Ser
545                 550                 555                 560

Gln Val Asn His Thr Ile Leu Gln Tyr Tyr Arg Cys Met Ala Ser Glu
                565                 570                 575

Leu Val Arg Val Asn Ile Thr Pro Val Val Ala Leu Trp Gln Pro Met
            580                 585                 590

Ala Pro Asn Gln Gly Leu Pro Arg Leu Leu Ala Arg Gln Gly Ala Trp
        595                 600                 605

Glu Asn Pro Tyr Thr Ala Leu Ala Phe Ala Glu Tyr Ala Arg Leu Cys
610                 615                 620

Phe Gln Glu Leu Gly His His Val Lys Leu Trp Ile Thr Met Asn Glu
625                 630                 635                 640

Pro Tyr Thr Arg Asn Met Thr Tyr Ser Ala Gly His Asn Leu Leu Lys
                645                 650                 655

Ala His Ala Leu Ala Trp His Val Tyr Asn Glu Lys Phe Arg His Ala
            660                 665                 670

Gln Asn Gly Lys Ile Ser Ile Ala Leu Gln Ala Asp Trp Ile Glu Pro
        675                 680                 685

Ala Cys Pro Phe Ser Gln Lys Asp Lys Glu Val Ala Glu Arg Val Leu
        690                 695                 700

Glu Phe Asp Ile Gly Trp Leu Ala Glu Pro Ile Phe Gly Ser Gly Asp
705                 710                 715                 720

Tyr Pro Trp Val Met Arg Asp Trp Leu Asn Gln Arg Asn Asn Phe Leu
                725                 730                 735

Leu Pro Tyr Phe Thr Glu Asp Glu Lys Lys Leu Ile Gln Gly Thr Phe
            740                 745                 750

Asp Phe Leu Ala Leu Ser His Tyr Thr Thr Ile Leu Val Asp Ser Glu
        755                 760                 765

Lys Glu Asp Pro Ile Lys Tyr Asn Asp Tyr Leu Glu Val Gln Glu Met
        770                 775                 780

Thr Asp Ile Thr Trp Leu Asn Ser Pro Ser Gln Val Ala Val Val Pro
785                 790                 795                 800

Trp Gly Leu Arg Lys Val Leu Asn Trp Leu Lys Phe Lys Tyr Gly Asp
                805                 810                 815

Leu Pro Met Tyr Ile Ile Ser Asn Gly Ile Asp Asp Gly Leu His Ala
            820                 825                 830

Glu Asp Asp Gln Leu Arg Val Tyr Tyr Met Gln Asn Tyr Ile Asn Glu
        835                 840                 845
```

```
Ala Leu Lys Ala His Ile Leu Asp Gly Ile Asn Leu Cys Gly Tyr Phe
850                 855                 860

Ala Tyr Ser Phe Asn Asp Arg Thr Ala Pro Arg Phe Gly Leu Tyr Arg
865                 870                 875                 880

Tyr Ala Ala Asp Gln Phe Glu Pro Lys Ala Ser Met Lys His Tyr Arg
                885                 890                 895

Lys Ile Ile Asp Ser Asn Gly Phe Pro Gly Pro Glu Thr Leu Glu Arg
                900                 905                 910

Phe Cys Pro Glu Glu Phe Thr Val Cys Thr Glu Cys Ser Phe Phe His
                915                 920                 925

Thr Arg Lys Ser
    930

<210> SEQ ID NO 3
<211> LENGTH: 49
<212> TYPE: PRT
<213> ORGANISM: Artificial Sequence
<220> FEATURE:
<223> OTHER INFORMATION: alpha-Klotho receptor binding arm portion

<400> SEQUENCE: 3

Asn Tyr Ile Gln Val Asp Thr Thr Leu Ser Gln Phe Thr Asp Leu Asn
1               5                   10                  15

Val Tyr Leu Trp Asp Val His His Ser Lys Arg Leu Ile Lys Val Asp
            20                  25                  30

Gly Val Val Thr Lys Lys Arg Lys Ser Tyr Cys Val Asp Phe Ala Ala
        35                  40                  45

Ile

<210> SEQ ID NO 4
<211> LENGTH: 251
<212> TYPE: PRT
<213> ORGANISM: Artificial Sequence
<220> FEATURE:
<223> OTHER INFORMATION: human FGF23

<400> SEQUENCE: 4

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg Arg
145                 150                 155                 160
```

```
Arg Asn Glu Ile Pro Leu Ile His Phe Asn Thr Pro Ile Pro Arg Arg
            165                 170                 175

His Thr Arg Ser Ala Glu Asp Asp Ser Glu Arg Asp Pro Leu Asn Val
        180                 185                 190

Leu Lys Pro Arg Ala Arg Met Thr Pro Ala Pro Ala Ser Cys Ser Gln
    195                 200                 205

Glu Leu Pro Ser Ala Glu Asp Asn Ser Pro Met Ala Ser Asp Pro Leu
        210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 5
<211> LENGTH: 3039
<212> TYPE: DNA
<213> ORGANISM: Artificial Sequence
<220> FEATURE:
<223> OTHER INFORMATION: human alpha-Klotho gene coding sequence

<400> SEQUENCE: 5
```

| | | |
|---|---|---|
| atgcccgcca gcgccccgcc gcgccgcccg cggccgccgc cgccgtcgct gtcgctgctg | 60 |
| ctggtgctgc tgggcctggg cggccgccgc ctgcgtgcgg agccgggcga cggcgcgcag | 120 |
| acctgggccc gtttctcgcg gcctcctgcc cccgaggccg cgggcctctt ccagggcacc | 180 |
| ttccccgacg gcttcctctg ggccgtgggc agcgccgcct accagaccga gggcggctgg | 240 |
| cagcagcacg gcaagggtgc gtccatctgg gatacgttca cccaccaccc cctggcaccc | 300 |
| ccgggagact cccggaacgc cagtctgccg ttgggcgccc cgtcgccgct gcagcccgcc | 360 |
| accggggacg tagccagcga cagctacaac aacgtcttcc gcgacacgga ggcgctgcgc | 420 |
| gagctcgggg tcactcacta ccgcttctcc atctcgtggg cgcgagtgct ccccaatggc | 480 |
| agcgcgggcg tccccaaccg cgaggggctg cgctactacc ggcgcctgct ggagcggctg | 540 |
| cgggagctgg gcgtgcagcc cgtggtcacc ctgtaccact gggacctgcc ccagcgcctg | 600 |
| caggacgcct acgcggctg ggccaaccgc gccctggccg accacttcag ggattacgcg | 660 |
| gagctctgct tccgccactt cggcggtcag gtcaagtact ggatcaccat cgacaacccc | 720 |
| tacgtggtgg cctggcacgg ctacgccacc gggcgcctgg cccccggcat ccggggcagc | 780 |
| ccgcggctcg gtacctggt ggcgcacaac ctcctcctgg ctcatgccaa agtctggcat | 840 |
| ctctacaata cttctttccg tcccactcag ggaggtcagg tgtccattgc cctaagctct | 900 |
| cactggatca atcctcgaag aatgaccgac cacagcatca agaatgtca aaaatctctg | 960 |
| gactttgtac taggttggtt tgccaaaccc gtatttattg atggtgacta tcccgagagc | 1020 |
| atgaagaata cctttcatc tattctgcct gattttactg aatctgagaa aagttcatc | 1080 |
| aaaggaactg ctgactttt tgctctttgc tttggaccca ccttgagttt caacttttg | 1140 |
| gaccctcaca tgaagttccg ccaattggaa tctcccaacc tgaggcaact gctttcctgg | 1200 |
| attgaccttg aatttaacca tcctcaaata tttattgtgg aaaatggctg gtttgtctca | 1260 |
| gggaccacca gagagatga tgccaaatat atgtattacc tcaaaaagtt catcatggaa | 1320 |
| accttaaaag ccatcaagct ggatggggtg gatgtcatcg gtataccgc atggtccctc | 1380 |
| atggatggtt tcgagtggca cagaggttac agcatcaggc gtggactctc ctatgttgac | 1440 |
| tttctaagcc aggacaagat gttgttgcca agtcttcag ccttgttcta ccaaaagctg | 1500 |
| atagagaaaa atggcttccc tcctttacct gaaaatcagc ccctagaagg gacatttccc | 1560 |

```
tgtgactttg cttggggagt tgttgacaac tacattcaag tagataccac tctgtctcag    1620
tttaccgacc tgaatgttta cctgtgggat gtccaccaca gtaaaaggct tattaaagtg    1680
gatggggttg tgaccaagaa gaggaaatcc tactgtgttg actttgctgc catccagccc    1740
cagatcgctt tactccagga aatgcacgtt acacattttc gcttctccct ggactgggcc    1800
ctgattctcc ctctgggtaa ccagtcccag gtgaaccaca ccatcctgca gtactatcgc    1860
tgcatggcca gcgagcttgt ccgtgtcaac atcaccccag tggtggccct gtggcagcct    1920
atggccccga accaaggact gccgcgcctc ctggccaggc agggcgcctg ggagaacccc    1980
tacactgccc tggcctttgc agagtatgcc cgactgtgct ttcaagagct cggccatcac    2040
gtcaagcttt ggataacgat gaatgagccg tatacaagga atatgacata cagtgctggc    2100
cacaaccttc tgaaggccca tgccctggct tggcatgtgt acaatgaaaa gtttaggcat    2160
gctcagaatg gaaaatatc catagccttg caggctgatt ggatagaacc tgcctgccct    2220
ttctcccaaa aggacaaaga ggtggctgag agagttttgg aatttgacat ggctggctg    2280 gctgagccca ttttcggctc tggagattat ccatgggtga tgagggactg gctgaaccaa    2340
agaaacaatt tcttcttcc ttatttcact gaagatgaaa aaaagctaat ccagggtacc    2400
tttgactttt tggctttaag ccattatacc accatccttg tagactcaga aaagaagat    2460 ccaataaaat acaatgatta cctagaagtg caagaaatga ccgacatcac gtggctcaac    2520
tcccccagtc aggtggcggt agtgccctgg gggttgcgca agtgctgaa ctggctgaag    2580 ttcaagtacg agaccctccc catgtacata atatccaatg aatcgatga cgggctgcat    2640 gctgaggacg accagctgag ggtgtattat atgcagaatt acataaacga agctctcaaa    2700
gcccacatac tggatggtat caatctttgc ggatactttg cttattcgtt taacgaccgc    2760
acagctccga ggtttggcct ctatcgttat gctgcagatc agtttgagcc caaggcatcc    2820
atgaaacatt acaggaaaat tattgacagc aatggtttcc cgggcccaga aactctggaa    2880
agattttgtc cagaagaatt caccgtgtgt actgagtgca gttttttcca cacccgaaag    2940
tctttactgg ctttcatagc ttttctattt tttgcttcta ttatttctct ctcccttata    3000
ttttactact cgaagaaagg cagaagaagt tacaaatag                          3039
```

<210> SEQ ID NO 6
<211> LENGTH: 2880
<212> TYPE: DNA
<213> ORGANISM: Artificial Sequence
<220> FEATURE:
<223> OTHER INFORMATION: Nucleic acid molecule encoding alpha-Klotho ectodomain/delta RBA

<400> SEQUENCE: 6

```
atgcccgcca gcgccccgcc gcgccgcccg cggccgccgc cgccgtcgct gtcgctgctg     60
ctggtgctgc tgggcctggg cggccgccgc ctgcgtgcgg agccgggcga cggcgcgcag    120
acctgggccc gtttctcgcg gcctcctgcc ccgaggccgc gggcctcttc cagggcacc    180 ttccccgacg gcttcctctg ggccgtgggc agcgccgcct accagaccga gggcggctgg    240
cagcagcacg gcaagggtgc gtccatctgg gatacgttca cccaccaccc cctgcacccc    300
ccgggagact cccggaacgc cagtctgccg ttgggcgccc cgtcgccgct gcagcccgcc    360
accggggacg tagccagcga cagctacaac aacgtcttcc gcgacacgga ggcgctgcgc    420
gagctcgggg tcactcacta ccgcttctcc atctcgtggg cgcgagtgct ccccaatggc    480
agcgcgggcg tccccaaccg cgaggggctg cgctactacc ggcgcctgct ggagcggctg    540
```

-continued

```
cgggagctgg gcgtgcagcc cgtggtcacc ctgtaccact gggacctgcc ccagcgcctg      600
caggacgcct acggcggctg ggccaaccgc gccctggccg accacttcag ggattacgcg      660
gagctctgct tccgccactt cggcggtcag gtcaagtact ggatcaccat cgacaacccc      720
tacgtggtgg cctggcacgg ctacgccacc gggcgcctgg cccccggcat ccggggcagc      780
ccgcggctcg ggtacctggt ggcgcacaac ctcctcctgg ctcatgccaa agtctggcat      840
ctctacaata cttcttttcc g tcccactcag ggaggtcagg tgtccattgc cctaagctct     900
cactggatca atcctcgaag aatgaccgac cacagcatca agaatgtca aaaatctctg       960 gactttgtac taggttggtt tgccaaaccc gtatttattg atggtgacta tcccgagagc     1020
atgaagaata accttcatc tattctgcct gattttactg aatctgagaa aaagttcatc     1080
aaaggaactg ctgactttt tgctcttgc tttggaccca ccttgagttt caacttttg        1140 gaccctcaca tgaagttccg ccaattggaa tctcccaacc tgaggcaact gctttcctgg    1200
attgaccttg aatttaacca tcctcaaata tttattgtgg aaaatggctg gtttgtctca    1260
gggaccacca agagagatga tgccaaatat atgtattacc tcaaaaagtt catcatggaa    1320
accttaaaag ccatcaagct ggatggggtg gatgtcatcg gtataccgc atggtccctc     1380 atggatggtt tcgagtggca cagaggttac agcatcaggc gtggactctt ctatgttgac    1440
tttctaagcc aggacaagat gttgttgcca aagtcttcag ccttgttcta ccaaaagctg    1500
atagagaaaa atggcttccc tcctttacct gaaaatcagc ccctagaagg gacatttccc    1560
tgtgactttg cttggggagt tgttgacaac tacattcaag tagatacac tctgtctcag     1620 tttaccgaca agaagaggaa atcctactgt gttgactttg ctgccatcca gccccagatc    1680
gctttactcc aggaaatgca cgttacacat tttcgcttct ccctggactg ggccctgatt    1740
ctccctctgg gtaaccagtc ccaggtgaac cacaccatcc tgcagtacta tcgctgcatg    1800
gccagcgagc ttgtccgtgt caacatcacc ccagtggtgg ccctgtggca gcctatggcc    1860
ccgaaccaag gactgccgcg cctcctggcc aggcagggcg cctgggagaa cccctacact    1920
gccctggcct ttgcagagta tgcccgactg tgctttcaag agctcggcca tcacgtcaag    1980 cttttggataa cgatgaatga gccgtataca aggaatatga catacagtgc tggccacaac    2040
cttctgaagg cccatgccct ggcttggcat gtgtacaatg aaaagtttag gcatgctcag    2100
aatgggaaaa tatccatagc cttgcaggct gattggatag aacctgcctg ccctttctcc    2160
caaaaggaca agaggtggc tgagagagtt ttggaatttg acattggctg gctggctgag    2220
cccattttcg gctctggaga ttatccatgg gtgatgaggg actggctgaa ccaaagaaac    2280
aatttctttc ttccttattt cactgaagat gaaaaaagc taatccaggg tacctttgac    2340
tttttggctt taagccatta taccaccatc cttgtagact cagaaaaga agatccaata    2400 aaatacaatg attacctaga agtgcaagaa atgaccgaca tcacgtggct caactccccc    2460
agtcaggtgg cggtagtgcc ctgggggttg cgcaaagtgc tgaactggct gaagttcaag    2520
tacggagacc tccccatgta cataatatcc aatggaatcg atgacgggct gcatgctgag    2580
gacgaccagc tgagggtgta ttatatgcag aattacataa acgaagctct caaagcccac    2640
atactggatg gtatcaatct ttgcggatac tttgcttatt cgtttaacga ccgcacagct    2700
ccgagggttg gcctctatcg ttatgctgca gatcagtttg agcccaaggc atccatgaaa    2760
cattacagga aaattattga cagcaatggt tccccgggcc cagaaactct ggaaagattt    2820
tgtccagaag aattcaccgt gtgtactgag tgcagttttt ttcacacccg aaagtcttag    2880
```

```
<210> SEQ ID NO 7
<211> LENGTH: 959
<212> TYPE: PRT
<213> ORGANISM: Artificial Sequence
<220> FEATURE:
<223> OTHER INFORMATION: alpha-Klotho ectodomain/delta RBA

<400> SEQUENCE: 7
```

| | | | | | | | | | | | | | | | |
|---|---|---|---|---|---|---|---|---|---|---|---|---|---|---|---|
| Met | Pro | Ala | Ser | Ala | Pro | Pro | Arg | Arg | Pro | Arg | Pro | Pro | Pro | Ser | |
| 1 | | | | 5 | | | | | 10 | | | | | 15 | |
| Leu | Ser | Leu | Leu | Leu | Val | Leu | Leu | Gly | Leu | Gly | Gly | Arg | Arg | Leu | Arg |
| | | | 20 | | | | | 25 | | | | | 30 | | |
| Ala | Glu | Pro | Gly | Asp | Gly | Ala | Gln | Thr | Trp | Ala | Arg | Val | Ser | Arg | Pro |
| | | 35 | | | | | 40 | | | | | 45 | | | |
| Pro | Ala | Pro | Glu | Ala | Ala | Gly | Leu | Phe | Gln | Gly | Thr | Phe | Pro | Asp | Gly |
| | 50 | | | | | 55 | | | | | 60 | | | | |
| Phe | Leu | Trp | Ala | Val | Gly | Ser | Ala | Ala | Tyr | Gln | Thr | Glu | Gly | Gly | Trp |
| 65 | | | | | 70 | | | | | 75 | | | | | 80 |
| Gln | Gln | His | Gly | Lys | Gly | Ala | Ser | Ile | Trp | Asp | Thr | Phe | Thr | His | His |
| | | | | 85 | | | | | 90 | | | | | 95 | |
| Pro | Leu | Ala | Pro | Pro | Gly | Asp | Ser | Arg | Asn | Ala | Ser | Leu | Pro | Leu | Gly |
| | | | 100 | | | | | 105 | | | | | 110 | | |
| Ala | Pro | Ser | Pro | Leu | Gln | Pro | Ala | Thr | Gly | Asp | Val | Ala | Ser | Asp | Ser |
| | | 115 | | | | | 120 | | | | | 125 | | | |
| Tyr | Asn | Asn | Val | Phe | Arg | Asp | Thr | Glu | Ala | Leu | Arg | Glu | Leu | Gly | Val |
| | 130 | | | | | 135 | | | | | 140 | | | | |
| Thr | His | Tyr | Arg | Phe | Ser | Ile | Ser | Trp | Ala | Arg | Val | Leu | Pro | Asn | Gly |
| 145 | | | | | 150 | | | | | 155 | | | | | 160 |
| Ser | Ala | Gly | Val | Pro | Asn | Arg | Glu | Gly | Leu | Arg | Tyr | Tyr | Arg | Arg | Leu |
| | | | | 165 | | | | | 170 | | | | | 175 | |
| Leu | Glu | Arg | Leu | Arg | Glu | Leu | Gly | Val | Gln | Pro | Val | Val | Thr | Leu | Tyr |
| | | | 180 | | | | | 185 | | | | | 190 | | |
| His | Trp | Asp | Leu | Pro | Gln | Arg | Leu | Gln | Asp | Ala | Tyr | Gly | Gly | Trp | Ala |
| | | 195 | | | | | 200 | | | | | 205 | | | |
| Asn | Arg | Ala | Leu | Ala | Asp | His | Phe | Arg | Asp | Tyr | Ala | Glu | Leu | Cys | Phe |
| | 210 | | | | | 215 | | | | | 220 | | | | |
| Arg | His | Phe | Gly | Gly | Gln | Val | Lys | Tyr | Trp | Ile | Thr | Ile | Asp | Asn | Pro |
| 225 | | | | | 230 | | | | | 235 | | | | | 240 |
| Tyr | Val | Val | Ala | Trp | His | Gly | Tyr | Ala | Thr | Gly | Arg | Leu | Ala | Pro | Gly |
| | | | | 245 | | | | | 250 | | | | | 255 | |
| Ile | Arg | Gly | Ser | Pro | Arg | Leu | Gly | Tyr | Leu | Val | Ala | His | Asn | Leu | Leu |
| | | | 260 | | | | | 265 | | | | | 270 | | |
| Leu | Ala | His | Ala | Lys | Val | Trp | His | Leu | Tyr | Asn | Thr | Ser | Phe | Arg | Pro |
| | | 275 | | | | | 280 | | | | | 285 | | | |
| Thr | Gln | Gly | Gly | Gln | Val | Ser | Ile | Ala | Leu | Ser | Ser | His | Trp | Ile | Asn |
| | 290 | | | | | 295 | | | | | 300 | | | | |
| Pro | Arg | Arg | Met | Thr | Asp | His | Ser | Ile | Lys | Glu | Cys | Gln | Lys | Ser | Leu |
| 305 | | | | | 310 | | | | | 315 | | | | | 320 |
| Asp | Phe | Val | Leu | Gly | Trp | Phe | Ala | Lys | Pro | Val | Phe | Ile | Asp | Gly | Asp |
| | | | | 325 | | | | | 330 | | | | | 335 | |
| Tyr | Pro | Glu | Ser | Met | Lys | Asn | Asn | Leu | Ser | Ser | Ile | Leu | Pro | Asp | Phe |
| | | | 340 | | | | | 345 | | | | | 350 | | |
| Thr | Glu | Ser | Glu | Lys | Lys | Phe | Ile | Lys | Gly | Thr | Ala | Asp | Phe | Phe | Ala |
| | | 355 | | | | | 360 | | | | | 365 | | | |

-continued

```
Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                    405                 410                 415

Trp Phe Val Ser Gly Thr Thr Lys Arg Asp Asp Ala Lys Tyr Met Tyr
                420                 425                 430

Tyr Leu Lys Lys Phe Ile Met Glu Thr Leu Lys Ala Ile Lys Leu Asp
            435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                    485                 490                 495

Tyr Gln Lys Leu Ile Glu Lys Asn Gly Phe Pro Pro Leu Pro Glu Asn
                500                 505                 510

Gln Pro Leu Glu Gly Thr Phe Pro Cys Asp Phe Ala Trp Gly Val Val
            515                 520                 525

Asp Asn Tyr Ile Gln Val Asp Thr Thr Leu Ser Gln Phe Thr Asp Lys
    530                 535                 540

Lys Arg Lys Ser Tyr Cys Val Asp Phe Ala Ala Ile Gln Pro Gln Ile
545                 550                 555                 560

Ala Leu Leu Gln Glu Met His Val Thr His Phe Arg Phe Ser Leu Asp
                    565                 570                 575

Trp Ala Leu Ile Leu Pro Leu Gly Asn Gln Ser Gln Val Asn His Thr
                580                 585                 590

Ile Leu Gln Tyr Tyr Arg Cys Met Ala Ser Glu Leu Val Arg Val Asn
            595                 600                 605

Ile Thr Pro Val Val Ala Leu Trp Gln Pro Met Ala Pro Asn Gln Gly
    610                 615                 620

Leu Pro Arg Leu Leu Ala Arg Gln Gly Ala Trp Glu Asn Pro Tyr Thr
625                 630                 635                 640

Ala Leu Ala Phe Ala Glu Tyr Ala Arg Leu Cys Phe Gln Glu Leu Gly
                    645                 650                 655

His His Val Lys Leu Trp Ile Thr Met Asn Glu Pro Tyr Thr Arg Asn
                660                 665                 670

Met Thr Tyr Ser Ala Gly His Asn Leu Leu Lys Ala His Ala Leu Ala
            675                 680                 685

Trp His Val Tyr Asn Glu Lys Phe Arg His Ala Gln Asn Gly Lys Ile
    690                 695                 700

Ser Ile Ala Leu Gln Ala Asp Trp Ile Glu Pro Ala Cys Pro Phe Ser
705                 710                 715                 720

Gln Lys Asp Lys Glu Val Ala Glu Arg Val Leu Glu Phe Asp Ile Gly
                    725                 730                 735

Trp Leu Ala Glu Pro Ile Phe Gly Ser Gly Asp Tyr Pro Trp Val Met
                740                 745                 750

Arg Asp Trp Leu Asn Gln Arg Asn Asn Phe Leu Leu Pro Tyr Phe Thr
            755                 760                 765

Glu Asp Glu Lys Lys Leu Ile Gln Gly Thr Phe Asp Phe Leu Ala Leu
    770                 775                 780

Ser His Tyr Thr Thr Ile Leu Val Asp Ser Glu Lys Glu Asp Pro Ile
```

```
                785                 790                 795                 800
Lys Tyr Asn Asp Tyr Leu Glu Val Gln Glu Met Thr Asp Ile Thr Trp
                805                 810                 815

Leu Asn Ser Pro Ser Gln Val Ala Val Val Pro Trp Gly Leu Arg Lys
                820                 825                 830

Val Leu Asn Trp Leu Lys Phe Lys Tyr Gly Asp Leu Pro Met Tyr Ile
                835                 840                 845

Ile Ser Asn Gly Ile Asp Asp Gly Leu His Ala Glu Asp Asp Gln Leu
    850                 855                 860

Arg Val Tyr Tyr Met Gln Asn Tyr Ile Asn Glu Ala Leu Lys Ala His
865                 870                 875                 880

Ile Leu Asp Gly Ile Asn Leu Cys Gly Tyr Phe Ala Tyr Ser Phe Asn
                885                 890                 895

Asp Arg Thr Ala Pro Arg Phe Gly Leu Tyr Arg Tyr Ala Ala Asp Gln
                900                 905                 910

Phe Glu Pro Lys Ala Ser Met Lys His Tyr Arg Lys Ile Ile Asp Ser
                915                 920                 925

Asn Gly Phe Pro Gly Pro Glu Thr Leu Glu Arg Phe Cys Pro Glu Glu
            930                 935                 940

Phe Thr Val Cys Thr Glu Cys Ser Phe Phe His Thr Arg Lys Ser
945                 950                 955

<210> SEQ ID NO 8
<211> LENGTH: 209
<212> TYPE: PRT
<213> ORGANISM: Artificial Sequence
<220> FEATURE:
<223> OTHER INFORMATION: Human FGF21

<400> SEQUENCE: 8

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
```

195                 200                 205

Ser

<210> SEQ ID NO 9
<211> LENGTH: 822
<212> TYPE: PRT
<213> ORGANISM: Artificial Sequence
<220> FEATURE:
<223> OTHER INFORMATION: Human FGFR1c

<400> SEQUENCE: 9

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Arg Pro Ala Val
            355                 360                 365

Met Thr Ser Pro Leu Tyr Leu Glu Ile Ile Ile Tyr Cys Thr Gly Ala
            370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
            435                 440                 445

Leu Ser Ser Ser Gly Thr Pro Met Leu Ala Gly Val Ser Glu Tyr Glu
            450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
            515                 520                 525

Ile Ser Glu Met Glu Met Met Lys Met Ile Gly Lys His Lys Asn Ile
            530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
            610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
            675                 680                 685

Leu Leu Trp Glu Ile Phe Thr Leu Gly Gly Ser Pro Tyr Pro Gly Val
            690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
                725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
            755                 760                 765

```
Leu Ser Met Pro Leu Asp Gln Tyr Ser Pro Ser Phe Pro Asp Thr Arg
        770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
                805                 810                 815

Gly Gly Leu Lys Arg Arg
            820

<210> SEQ ID NO 10
<211> LENGTH: 20
<212> TYPE: DNA
<213> ORGANISM: Artificial Sequence
<220> FEATURE:
<223> OTHER INFORMATION: PCR Primer for Egr1

<400> SEQUENCE: 10
gaggagatga tgctgctgag                                           20

<210> SEQ ID NO 11
<211> LENGTH: 19
<212> TYPE: DNA
<213> ORGANISM: Artificial Sequence
<220> FEATURE:
<223> OTHER INFORMATION: PCR Primer for Egr1

<400> SEQUENCE: 11
tgctgctgct gctattacc                                            19

<210> SEQ ID NO 12
<211> LENGTH: 20
<212> TYPE: DNA
<213> ORGANISM: Artificial Sequence
<220> FEATURE:
<223> OTHER INFORMATION: PCR Primer for cyclophilin

<400> SEQUENCE: 12
gtctcttttc gccgcttgct                                           20

<210> SEQ ID NO 13
<211> LENGTH: 25
<212> TYPE: DNA
<213> ORGANISM: Artificial Sequence
<220> FEATURE:
<223> OTHER INFORMATION: PCR Primer for cyclophilin

<400> SEQUENCE: 13
tctgctgtct ttggaacttt gtctg                                     25

<210> SEQ ID NO 14
<211> LENGTH: 79
<212> TYPE: PRT
<213> ORGANISM: Artificial Sequence
<220> FEATURE:
<223> OTHER INFORMATION: FGFR1b portion

<400> SEQUENCE: 14

Asp Pro Gln Pro His Ile Gln Trp Leu Lys His Ile Glu Val Asn Gly
1               5                   10                  15

Ser Lys Ile Gly Pro Asp Asn Leu Pro Tyr Val Gln Ile Leu Lys His
            20                  25                  30

Ser Gly Ile Asn Ser Ser Asp Ala Glu Val Leu Thr Leu Phe Asn Val
        35                  40                  45
```

```
Thr Glu Ala Gln Ser Gly Glu Tyr Val Cys Lys Val Ser Asn Tyr Ile
 50                  55                  60
Gly Glu Ala Asn Gln Ser Ala Trp Leu Thr Val Thr Arg Pro Ala
 65                  70                  75
```

<210> SEQ ID NO 15  
<211> LENGTH: 80  
<212> TYPE: PRT  
<213> ORGANISM: Artificial Sequence  
<220> FEATURE:  
<223> OTHER INFORMATION: FGFR1c portion

<400> SEQUENCE: 15

```
Asp Pro Gln Pro His Ile Gln Trp Leu Lys His Ile Glu Val Asn Gly
 1                5                  10                  15
Ser Lys Ile Gly Pro Asp Asn Leu Pro Tyr Val Gln Ile Leu Lys Thr
                 20                  25                  30
Ala Gly Val Asn Thr Thr Asp Lys Glu Met Glu Val Leu His Leu Arg
             35                  40                  45
Asn Val Ser Phe Glu Asp Ala Gly Glu Tyr Thr Cys Leu Ala Gly Asn
 50                  55                  60
Ser Ile Gly Leu Ser His His Ser Ala Trp Leu Thr Val Leu Glu Ala
 65                  70                  75                  80
```

<210> SEQ ID NO 16  
<211> LENGTH: 79  
<212> TYPE: PRT  
<213> ORGANISM: Artificial Sequence  
<220> FEATURE:  
<223> OTHER INFORMATION: FGFR2b portion

<400> SEQUENCE: 16

```
Asp Ala Gln Pro His Ile Gln Trp Ile Lys His Val Glu Lys Asn Gly
 1                5                  10                  15
Ser Lys Tyr Gly Pro Asp Gly Leu Pro Tyr Leu Lys Val Leu Lys His
                 20                  25                  30
Ser Gly Ile Asn Ser Ser Asn Ala Glu Val Leu Ala Leu Phe Asn Val
             35                  40                  45
Thr Glu Ala Asp Ala Gly Glu Tyr Ile Cys Lys Val Ser Asn Tyr Ile
 50                  55                  60
Gly Gln Ala Asn Gln Ser Ala Trp Leu Thr Val Leu Pro Lys Gln
 65                  70                  75
```

<210> SEQ ID NO 17  
<211> LENGTH: 79  
<212> TYPE: PRT  
<213> ORGANISM: Artificial Sequence  
<220> FEATURE:  
<223> OTHER INFORMATION: FGFR2c portion

<400> SEQUENCE: 17

```
Asp Ala Gln Pro His Ile Gln Trp Ile Lys His Val Glu Lys Asn Gly
 1                5                  10                  15
Ser Lys Tyr Gly Pro Asp Gly Leu Pro Tyr Leu Lys Val Leu Lys Ala
                 20                  25                  30
Ala Gly Val Asn Thr Thr Asp Lys Glu Ile Glu Val Leu Tyr Ile Arg
             35                  40                  45
Asn Val Thr Phe Glu Asp Ala Gly Glu Tyr Thr Cys Leu Ala Gly Asn
 50                  55                  60
Ser Ile Gly Ile Ser Phe His Ser Ala Trp Leu Thr Val Leu Pro
```

```
65                  70                  75

<210> SEQ ID NO 18
<211> LENGTH: 80
<212> TYPE: PRT
<213> ORGANISM: Artificial Sequence
<220> FEATURE:
<223> OTHER INFORMATION: FGFR3b portion

<400> SEQUENCE: 18

Asp Ala Gln Pro His Ile Gln Trp Leu Lys His Val Glu Val Asn Gly
1               5                   10                  15

Ser Lys Val Gly Pro Asp Gly Thr Pro Tyr Val Thr Val Leu Lys Ser
            20                  25                  30

Trp Ile Ser Glu Ser Val Glu Ala Asp Val Arg Leu Arg Leu Ala Asn
        35                  40                  45

Val Ser Glu Arg Asp Gly Gly Glu Tyr Leu Cys Arg Ala Thr Asn Phe
    50                  55                  60

Ile Gly Val Ala Glu Lys Ala Phe Trp Leu Ser Val His Gly Pro Arg
65                  70                  75                  80

<210> SEQ ID NO 19
<211> LENGTH: 78
<212> TYPE: PRT
<213> ORGANISM: Artificial Sequence
<220> FEATURE:
<223> OTHER INFORMATION: FGFR3c portion

<400> SEQUENCE: 19

Asp Ala Gln Pro His Ile Gln Trp Leu Lys His Val Glu Val Asn Gly
1               5                   10                  15

Ser Lys Val Gly Pro Asp Gly Thr Pro Tyr Val Thr Val Leu Lys Thr
            20                  25                  30

Ala Gly Ala Asn Thr Thr Asp Lys Glu Leu Glu Val Leu Ser Leu His
        35                  40                  45

Asn Val Thr Phe Glu Asp Ala Gly Glu Tyr Thr Cys Leu Ala Gly Asn
    50                  55                  60

Ser Ile Gly Phe Ser His His Ser Ala Trp Leu Val Val Leu
65                  70                  75

<210> SEQ ID NO 20
<211> LENGTH: 79
<212> TYPE: PRT
<213> ORGANISM: Artificial Sequence
<220> FEATURE:
<223> OTHER INFORMATION: FGFR4 portion

<400> SEQUENCE: 20

Asp Ala Gln Pro His Ile Gln Trp Leu Lys His Ile Val Ile Asn Gly
1               5                   10                  15

Ser Ser Phe Gly Ala Asp Gly Phe Pro Tyr Val Gln Val Leu Lys Thr
            20                  25                  30

Ala Asp Ile Asn Ser Ser Glu Val Glu Val Leu Tyr Leu Arg Asn Val
        35                  40                  45

Ser Ala Glu Asp Ala Gly Glu Tyr Thr Cys Leu Ala Gly Asn Ser Ile
    50                  55                  60

Gly Leu Ser Tyr Gln Ser Ala Trp Leu Thr Val Leu Pro Glu Glu
65                  70                  75

<210> SEQ ID NO 21
```

<211> LENGTH: 469
<212> TYPE: PRT
<213> ORGANISM: Artificial Sequence
<220> FEATURE:
<223> OTHER INFORMATION: Klotho Related Protein KLrP

<400> SEQUENCE: 21

```
Met Ala Phe Pro Ala Gly Phe Gly Trp Ala Ala Thr Ala Ala Tyr
1               5                   10                  15

Gln Val Glu Gly Gly Trp Asp Ala Asp Gly Lys Gly Pro Cys Val Trp
            20                  25                  30

Asp Thr Phe Thr His Gln Gly Gly Glu Arg Val Phe Lys Asn Gln Thr
        35                  40                  45

Gly Asp Val Ala Cys Gly Ser Tyr Thr Leu Trp Glu Glu Asp Leu Lys
    50                  55                  60

Cys Ile Lys Gln Leu Gly Leu Thr His Tyr Arg Phe Ser Leu Ser Trp
65                  70                  75                  80

Ser Arg Leu Leu Pro Asp Gly Thr Thr Gly Phe Ile Asn Gln Lys Gly
                85                  90                  95

Ile Asp Tyr Tyr Asn Lys Ile Ile Asp Asp Leu Leu Lys Asn Gly Val
            100                 105                 110

Thr Pro Ile Val Thr Leu Tyr His Phe Asp Leu Pro Gln Thr Leu Glu
        115                 120                 125

Asp Gln Gly Gly Trp Leu Ser Glu Ala Ile Ile Glu Ser Phe Asp Lys
    130                 135                 140

Tyr Ala Gln Phe Cys Phe Ser Thr Phe Gly Asp Arg Val Lys Gln Trp
145                 150                 155                 160

Ile Thr Ile Asn Glu Ala Asn Val Leu Ser Val Met Ser Tyr Asp Leu
                165                 170                 175

Gly Met Phe Pro Pro Gly Ile Pro His Phe Gly Thr Gly Gly Tyr Gln
            180                 185                 190

Ala Ala His Asn Leu Ile Lys Ala His Ala Arg Ser Trp His Ser Tyr
        195                 200                 205

Asp Ser Leu Phe Arg Lys Lys Gln Lys Gly Met Val Ser Leu Ser Leu
    210                 215                 220

Phe Ala Val Trp Leu Glu Pro Ala Asp Pro Asn Ser Val Ser Asp Gln
225                 230                 235                 240

Glu Ala Ala Lys Arg Ala Ile Thr Phe His Leu Asp Leu Phe Ala Lys
                245                 250                 255

Pro Ile Phe Ile Asp Gly Asp Tyr Pro Glu Val Val Lys Ser Gln Ile
            260                 265                 270

Ala Ser Met Ser Gln Lys Gln Gly Tyr Pro Ser Ser Arg Leu Pro Glu
        275                 280                 285

Phe Thr Glu Glu Glu Lys Lys Met Ile Lys Gly Thr Ala Asp Phe Phe
    290                 295                 300

Ala Val Gln Tyr Tyr Thr Thr Arg Leu Ile Lys Tyr Gln Glu Asn Lys
305                 310                 315                 320

Lys Gly Glu Leu Gly Ile Leu Gln Asp Ala Glu Ile Glu Phe Phe Pro
                325                 330                 335

Asp Pro Ser Trp Lys Asn Val Asp Trp Ile Tyr Val Val Pro Trp Gly
            340                 345                 350

Val Cys Lys Leu Leu Lys Tyr Ile Lys Asp Thr Tyr Asn Asn Pro Val
        355                 360                 365

Ile Tyr Ile Thr Glu Asn Gly Phe Pro Gln Ser Asp Pro Ala Pro Leu
    370                 375                 380
```

```
Asp Asp Thr Gln Arg Trp Glu Tyr Phe Arg Gln Thr Phe Gln Glu Leu
385                 390                 395                 400

Phe Lys Ala Ile Gln Leu Asp Lys Val Asn Leu Gln Val Tyr Cys Ala
                405                 410                 415

Trp Ser Leu Leu Asp Asn Phe Glu Trp Asn Gln Gly Tyr Ser Ser Arg
            420                 425                 430

Phe Gly Leu Phe His Val Asp Phe Glu Asp Pro Ala Arg Pro Arg Val
        435                 440                 445

Pro Tyr Thr Ser Ala Lys Glu Tyr Ala Lys Ile Ile Arg Asn Asn Gly
    450                 455                 460

Leu Glu Ala His Leu
465

<210> SEQ ID NO 22
<211> LENGTH: 1012
<212> TYPE: PRT
<213> ORGANISM: Artificial Sequence
<220> FEATURE:
<223> OTHER INFORMATION: alpha-Klotho

<400> SEQUENCE: 22

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Val Ser Arg Pro
            35                  40                  45

Pro Ala Pro Glu Ala Ala Gly Leu Phe Gln Gly Thr Phe Pro Asp Gly
    50                  55                  60

Phe Leu Trp Ala Val Gly Ser Ala Ala Tyr Gln Thr Glu Gly Gly Trp
65                  70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
                100                 105                 110

Ala Pro Ser Pro Leu Gln Pro Ala Thr Gly Asp Val Ala Ser Asp Ser
            115                 120                 125

Tyr Asn Asn Val Phe Arg Asp Thr Glu Ala Leu Arg Glu Leu Gly Val
        130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270
```

```
Leu Ala His Ala Lys Val Trp His Leu Tyr Asn Thr Ser Phe Arg Pro
            275                 280                 285

Thr Gln Gly Gly Gln Val Ser Ile Ala Leu Ser Ser His Trp Ile Asn
        290                 295                 300

Pro Arg Arg Met Thr Asp His Ser Ile Lys Glu Cys Gln Lys Ser Leu
305                 310                 315                 320

Asp Phe Val Leu Gly Trp Phe Ala Lys Pro Val Phe Ile Asp Gly Asp
                325                 330                 335

Tyr Pro Glu Ser Met Lys Asn Asn Leu Ser Ser Ile Leu Pro Asp Phe
            340                 345                 350

Thr Glu Ser Glu Lys Lys Phe Ile Lys Gly Thr Ala Asp Phe Phe Ala
        355                 360                 365

Leu Cys Phe Gly Pro Thr Leu Ser Phe Gln Leu Leu Asp Pro His Met
    370                 375                 380

Lys Phe Arg Gln Leu Glu Ser Pro Asn Leu Arg Gln Leu Leu Ser Trp
385                 390                 395                 400

Ile Asp Leu Glu Phe Asn His Pro Gln Ile Phe Ile Val Glu Asn Gly
                405                 410                 415

Trp Phe Val Ser Gly Thr Thr Lys Arg Asp Asp Ala Lys Tyr Met Tyr
            420                 425                 430

Tyr Leu Lys Lys Phe Ile Met Glu Thr Leu Lys Ala Ile Lys Leu Asp
        435                 440                 445

Gly Val Asp Val Ile Gly Tyr Thr Ala Trp Ser Leu Met Asp Gly Phe
    450                 455                 460

Glu Trp His Arg Gly Tyr Ser Ile Arg Arg Gly Leu Phe Tyr Val Asp
465                 470                 475                 480

Phe Leu Ser Gln Asp Lys Met Leu Leu Pro Lys Ser Ser Ala Leu Phe
                485                 490                 495

Tyr Gln Lys Leu Ile Glu Lys Asn Gly Phe Pro Pro Leu Pro Glu Asn
            500                 505                 510

Gln Pro Leu Glu Gly Thr Phe Pro Cys Asp Phe Ala Trp Gly Val Val
        515                 520                 525

Asp Asn Tyr Ile Gln Val Asp Thr Thr Leu Ser Gln Phe Thr Asp Leu
    530                 535                 540

Asn Val Tyr Leu Trp Asp Val His His Ser Lys Arg Leu Ile Lys Val
545                 550                 555                 560

Asp Gly Val Val Thr Lys Lys Arg Lys Ser Tyr Cys Val Asp Phe Ala
                565                 570                 575

Ala Ile Gln Pro Gln Ile Ala Leu Leu Gln Glu Met His Val Thr His
            580                 585                 590

Phe Arg Phe Ser Leu Asp Trp Ala Leu Ile Leu Pro Leu Gly Asn Gln
        595                 600                 605

Ser Gln Val Asn His Thr Ile Leu Gln Tyr Tyr Arg Cys Met Ala Ser
    610                 615                 620

Glu Leu Val Arg Val Asn Ile Thr Pro Val Val Ala Leu Trp Gln Pro
625                 630                 635                 640

Met Ala Pro Asn Gln Gly Leu Pro Arg Leu Leu Ala Arg Gln Gly Ala
                645                 650                 655

Trp Glu Asn Pro Tyr Thr Ala Leu Ala Phe Ala Glu Tyr Ala Arg Leu
            660                 665                 670

Cys Phe Gln Glu Leu Gly His His Val Lys Leu Trp Ile Thr Met Asn
        675                 680                 685
```

```
Glu Pro Tyr Thr Arg Asn Met Thr Tyr Ser Ala Gly His Asn Leu Leu
    690                 695                 700

Lys Ala His Ala Leu Ala Trp His Val Tyr Asn Glu Lys Phe Arg His
705                 710                 715                 720

Ala Gln Asn Gly Lys Ile Ser Ile Ala Leu Gln Ala Asp Trp Ile Glu
                725                 730                 735

Pro Ala Cys Pro Phe Ser Gln Lys Asp Lys Glu Val Ala Glu Arg Val
            740                 745                 750

Leu Glu Phe Asp Ile Gly Trp Leu Ala Glu Pro Ile Phe Gly Ser Gly
        755                 760                 765

Asp Tyr Pro Trp Val Met Arg Asp Trp Leu Asn Gln Arg Asn Asn Phe
    770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Glu Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
            930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys Lys Gly Arg
        995                 1000                1005

Arg Ser Tyr Lys
    1010

<210> SEQ ID NO 23
<211> LENGTH: 1044
<212> TYPE: PRT
<213> ORGANISM: Artificial Sequence
<220> FEATURE:
<223> OTHER INFORMATION: beta-Klotho

<400> SEQUENCE: 23

Met Lys Pro Gly Cys Ala Ala Gly Ser Pro Gly Asn Glu Trp Ile Phe
1               5                   10                  15

Phe Ser Thr Asp Glu Ile Thr Arg Tyr Arg Asn Thr Met Ser Asn
            20                  25                  30
```

```
Gly Gly Leu Gln Arg Ser Val Ile Leu Ser Ala Leu Ile Leu Leu Arg
            35                  40                  45

Ala Val Thr Gly Phe Ser Gly Asp Gly Arg Ala Ile Trp Ser Lys Asn
50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
            115                 120                 125

Asp Ser Tyr Ile Phe Leu Glu Lys Asp Leu Ser Ala Leu Asp Phe Ile
130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
            195                 200                 205

Trp Lys Asn Asp Thr Ile Ile Asp Ile Phe Asn Asp Tyr Ala Thr Tyr
            210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
            275                 280                 285

Arg Pro His Gln Lys Gly Trp Leu Ser Ile Thr Leu Gly Ser His Trp
290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
            355                 360                 365

Phe Phe Ala Phe Ser Phe Gly Pro Asn Asn Phe Lys Pro Leu Asn Thr
370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
            420                 425                 430

Ile Tyr Met Met Lys Asn Phe Leu Ser Gln Val Leu Gln Ala Ile Arg
            435                 440                 445

Leu Asp Glu Ile Arg Val Phe Gly Tyr Thr Ala Trp Ser Leu Leu Asp
```

```
            450             455             460
Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
                    500                 505                 510

Ser Thr Pro Asp Val Gln Gly Gln Phe Pro Cys Asp Phe Ser Trp Gly
                515                 520                 525

Val Thr Glu Ser Val Leu Lys Pro Glu Ser Val Ala Ser Ser Pro Gln
            530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                    565                 570                 575

Thr Asp Phe Val Asn Ile Lys Lys Gln Leu Glu Met Leu Ala Arg Met
                580                 585                 590

Lys Val Thr His Tyr Arg Phe Ala Leu Asp Trp Ala Ser Val Leu Pro
            595                 600                 605

Thr Gly Asn Leu Ser Ala Val Asn Arg Gln Ala Leu Arg Tyr Tyr Arg
610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                    645                 650                 655

His Ala Asp Gly Trp Leu Asn Pro Ser Thr Ala Glu Ala Phe Gln Ala
                660                 665                 670

Tyr Ala Gly Leu Cys Phe Gln Glu Leu Gly Asp Leu Val Lys Leu Trp
                675                 680                 685

Ile Thr Ile Asn Glu Pro Asn Arg Leu Ser Asp Ile Tyr Asn Arg Ser
                690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                    725                 730                 735

Ala Val Ser Leu Ser Leu His Ala Asp Trp Ala Glu Pro Ala Asn Pro
                740                 745                 750

Tyr Ala Asp Ser His Trp Arg Ala Ala Glu Arg Phe Leu Gln Phe Glu
                755                 760                 765

Ile Ala Trp Phe Ala Glu Pro Leu Phe Lys Thr Gly Asp Tyr Pro Ala
770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
                    805                 810                 815

Thr Val Asp Phe Cys Ala Leu Asn His Phe Thr Thr Arg Phe Val Met
                820                 825                 830

His Glu Gln Leu Ala Gly Ser Arg Tyr Asp Ser Asp Arg Asp Ile Gln
            835                 840                 845

Phe Leu Gln Asp Ile Thr Arg Leu Ser Ser Pro Thr Arg Leu Ala Val
850                 855                 860

Ile Pro Trp Gly Val Arg Lys Leu Leu Arg Trp Val Arg Arg Asn Tyr
865                 870                 875                 880
```

-continued

```
Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
            900                 905                 910

Glu Val Leu Lys Ala Tyr Leu Ile Asp Lys Val Arg Ile Lys Gly Tyr
        915                 920                 925

Tyr Ala Phe Lys Leu Ala Glu Glu Lys Ser Lys Pro Arg Phe Gly Phe
    930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Arg Cys
                965                 970                 975

Ser Gln Thr Gln Glu Asn Thr Glu Cys Thr Val Cys Leu Phe Leu Val
            980                 985                 990

Gln Lys Lys Pro Leu Ile Phe Leu Gly Cys Cys Phe Phe Ser Thr Leu
        995                 1000                1005

Val Leu  Leu Leu Ser Ile Ala  Ile Phe Gln Arg Gln  Lys Arg Arg
    1010                1015                1020

Lys Phe  Trp Lys Ala Lys Asn  Leu Gln His Ile Pro  Leu Lys Lys
    1025                1030                1035

Gly Lys  Arg Val Val Ser
    1040

<210> SEQ ID NO 24
<211> LENGTH: 16
<212> TYPE: PRT
<213> ORGANISM: Artificial Sequence
<220> FEATURE:
<223> OTHER INFORMATION: Unrelated sequence

<400> SEQUENCE: 24

Val Ser Gln Leu Thr Lys Pro Ile Ser Ser Leu Thr Lys Pro Tyr His
1               5                   10                  15

<210> SEQ ID NO 25
<211> LENGTH: 227
<212> TYPE: PRT
<213> ORGANISM: Artificial Sequence
<220> FEATURE:
<223> OTHER INFORMATION: FGF23 portion

<400> SEQUENCE: 25

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
```

```
                    115                 120                 125
Pro Tyr Ser Gln Phe Leu Ser Arg Arg Asn Glu Ile Pro Leu Ile His
    130                 135                 140

Phe Asn Thr Pro Ile Pro Arg Arg His Thr Arg Ser Ala Glu Asp Asp
145                 150                 155                 160

Ser Glu Arg Asp Pro Leu Asn Val Leu Lys Pro Arg Ala Arg Met Thr
                165                 170                 175

Pro Ala Pro Ala Ser Cys Ser Gln Glu Leu Pro Ser Ala Glu Asp Asn
            180                 185                 190

Ser Pro Met Ala Ser Asp Pro Leu Gly Val Val Arg Gly Gly Arg Val
        195                 200                 205

Asn Thr His Ala Gly Gly Thr Gly Pro Glu Gly Cys Arg Pro Phe Ala
    210                 215                 220

Lys Phe Ile
225

<210> SEQ ID NO 26
<211> LENGTH: 181
<212> TYPE: PRT
<213> ORGANISM: Artificial Sequence
<220> FEATURE:
<223> OTHER INFORMATION: FGF21 portion

<400> SEQUENCE: 26

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 27
<211> LENGTH: 194
<212> TYPE: PRT
<213> ORGANISM: Artificial Sequence
<220> FEATURE:
<223> OTHER INFORMATION: FGF19

<400> SEQUENCE: 27
```

-continued

```
Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 28
<211> LENGTH: 147
<212> TYPE: DNA
<213> ORGANISM: Artificial Sequence
<220> FEATURE:
<223> OTHER INFORMATION: Nucleic acid molecule encoding alpha-Klotho
      receptor binding arm

<400> SEQUENCE: 28
aactacattc aagtagatac cactctgtct cagtttaccg acctgaatgt ttacctgtgg      60
gatgtccacc acagtaaaag gcttattaaa gtggatgggg ttgtgaccaa gaagaggaaa     120
tcctactgtg ttgactttgc tgccatc                                         147

<210> SEQ ID NO 29
<211> LENGTH: 66
<212> TYPE: DNA
<213> ORGANISM: Artificial Sequence
<220> FEATURE:
<223> OTHER INFORMATION: Portion of RBA deleted

<400> SEQUENCE: 29
ctgaatgttt acctgtggga tgtccaccac agtaaaaggc ttattaaagt ggatggggtt      60
gtgacc                                                                 66
```

SOLUBLE ALPHA-KLOTHO PROTEINS, PROTEIN FRAGMENTS, AND USES THEREOF

This application is a national stage application under 35 U.S.C. § 371 of PCT International Application No. PCT/US19/13282, filed Jan. 11, 2019, which claims the priority benefit of U.S. Provisional Application Ser. No. 62/616,945, filed Jan. 12, 2018, which is hereby incorporated by reference in its entirety.

This invention was made with government support under grant number R01 DK091392 awarded by the National Institutes of Health. The government has certain rights in the invention.

FIELD OF THE INVENTION

The present invention relates to modified soluble α-Klotho proteins and isolated fragments of soluble α-Klotho protein. The present invention also relates to compositions comprising such modified soluble α-Klotho proteins and/or isolated fragments of soluble α-Klotho protein, as well as methods of their use.

BACKGROUND OF THE INVENTION

Endocrine fibroblast growth factor 23 (FGF23) regulates phosphate and vitamin D homeostasis by reducing cell surface expression of sodium phosphate co-transporters and by repressing transcription of rate-limiting enzymes for vitamin D biosynthesis (Shimada et al., "Targeted Ablation of Fgf23 Demonstrates an Essential Physiological Role of FGF23 in Phosphate and Vitamin D Metabolism," *J. Clin. Invest.* 113(4):561-568 (2004) and Gattineni et al., "FGF23 Decreases Renal NaPi-2a and NaPi-2c Expression and Induces Hypophosphatemia in Vivo Predominantly via FGF Receptor 1," *Am. J. Physiol. Renal Physiol.* 297(2):F282-291 (2009)) in the kidney. FGF23 exerts its metabolic functions by binding and activating FGF receptor tyrosine kinases (FGFRs) (Lemmon et al., "Cell Signaling by Receptor Tyrosine Kinases," *Cell* 141(7):1117-1134 (2010)) in an αKlotho co-receptor dependent fashion. The extracellular domain of a prototypical FGFR consists of three immunoglobulin-like domains: D1, D2, and D3. The membrane proximal portion comprising D2, D3, and the D2-D3 linker (FGFR$^{ecto}$) is both necessary and sufficient for FGF ligand binding (Schlessinger et al., "Crystal Structure of a Ternary FGF-FGFR-Heparin Complex Reveals a Dual Role for Heparin in FGFR Binding and Dimerization," *Mol. Cell* 6(3):743-750 (2000) and Mohammadi et al., "Structural Basis for Fibroblast Growth Factor Receptor Activation," *Cytokine Growth Factor Rev.* 16(2):107-137 (2005)). Tissue-specific alternative splicing in the D3 domain of FGFR1-3 generates "b" and "c" isoforms, each with distinct ligand-binding specificity (Mohammadi et al., "Structural Basis for Fibroblast Growth Factor Receptor Activation," *Cytokine Growth Factor Rev.* 16(2):107-137 (2005) and Goetz et al., "Exploring Mechanisms of FGF Signalling Through the Lens of Structural Biology," *Nat. Rev. Mol. Cell Biol.* 14(3):166-180 (2013)).

αKlotho, fortuitously discovered as an aging suppressor gene (Kuro-o et al., "Mutation of the Mouse Klotho Gene Leads to a Syndrome Resembling Ageing," *Nature* 390 (6655):45-51 (1997)), is a single-pass transmembrane protein with an extracellular domain composed of two tandem domains (KL1 and KL2), each with significant homology to family 1 glycosidases (Henrissat et al., "Structural and Sequence-Based Classification of Glycoside Hydrolases," *Curr. Opin. Struct. Biol.* 7(5):637-644 (1997)) (FIG. 6A). Membrane-bound αKlotho (αKlotho™) associates with cognate FGFRs of FGF23, namely the "c" splice isoforms of FGFR1 and FGFR3 (FGFR1c and FGFR3c) and FGFR4 (Goetz et al., "Molecular Insights into the Klotho-Dependent, Endocrine Mode of Action of Fibroblast Growth Factor 19 Subfamily Members," *Mol. Cell Biol.* 27(9):3417-3428 (2007); Goetz et al., "Isolated C-Terminal Tail of FGF23 Alleviates Hypophosphatemia by Inhibiting FGF23-FGFR-Klotho Complex Formation," *PNAS USA* 107(1): 407-412 (2010); Urakawa et al., "Klotho Converts Canonical FGF Receptor into a Specific Receptor for FGF23," *Nature* 444(7120):770-774 (2006); and Kurosu et al., "Regulation of Fibroblast Growth Factor-23 Signaling by Klotho," *J. Biol. Chem.* 281:6120-6123 (2006)). This enables them to bind and respond to FGF23 (Goetz et al., "Molecular Insights into the Klotho-Dependent, Endocrine Mode of Action of Fibroblast Growth Factor 19 Subfamily Members," *Mol. Cell Biol.* 27(9):3417-3428 (2007); Urakawa et al., "Klotho Converts Canonical FGF Receptor into a Specific Receptor for FGF23," *Nature* 444(7120): 770-774 (2006); and Kurosu et al., "Regulation of Fibroblast Growth Factor-23 Signaling by Klotho," *J. Biol. Chem.* 281:6120-6123 (2006)). αKlotho™ is predominantly expressed in the kidney distal tubules, the parathyroid gland, and the brain choroid plexus (Kuro-o et al., "Mutation of the Mouse Klotho Gene Leads to a Syndrome Resembling Ageing," *Nature* 390(6655):45-51 (1997) and Li et al., "Immunohistochemical Localization of Klotho Protein in Brain, Kidney, and Reproductive Organs of Mice," *Cell Struct. Funct.* 29(4):91-99 (2004)), and this is considered to determine target tissue specificity of FGF23 (Urakawa et al., "Klotho Converts Canonical FGF Receptor into a Specific Receptor for FGF23," *Nature* 444(7120):770-774 (2006) and Kurosu et al., "Regulation of Fibroblast Growth Factor-23 Signaling by Klotho," *J. Biol. Chem.* 281:6120-6123 (2006)). Cleavage of αKlotho™ by ADAM proteases (van Loon et al., "Shedding of Klotho by ADAMs in the Kidney," *Am. J. Physiol. Renal Physiol.* 309(4):F359-368 (2015) and Lindberg et al., "The Kidney is the Principal Organ Mediating Klotho Effects," *J. Am. Soc. Nephrol.* 25(10):2169-2175 (2014)) in kidney distal tubules sheds the αKlotho ectodomain (αKlotho$^{ecto}$; FIG. 6A) into body fluids, e.g. serum, urine, and cerebrospinal fluid (Chen et al., "Insulin Stimulates the Cleavage and Release of the Extracellular Domain of Klotho by ADAM10 and ADAM17," *PNAS USA* 104(50):19796-19801 (2007); Imura et al., "Secreted Klotho Protein in Sera and CSF: Implication for Post-Translational Cleavage in Release of Klotho Protein From Cell Membrane," *FEBS Lett* 565(1-3):143-147 (2004); Matsumura et al., "Identification of the Human Klotho Gene and its Two Transcripts Encoding Membrane and Secreted Klotho Protein," *Biochem. Biophys. Res. Commun.* 242(3):626-630 (1998); and Shiraki-Lida et al., "Structure of the Mouse Klotho Gene and Its Two Transcripts Encoding Membrane and Secreted Protein," *FEBS Lett* 424(1-2):6-10 (1998)). αKlotho$^{ecto}$ is thought to lack co-receptor activity and act as a circulating anti-aging hormone independent of FGF23 (Kurosu et al., "Suppression of Aging in Mice by the Hormone Klotho," *Science* 309(5742):1829-1833 (2005) and Hu et al., "Fibroblast Growth Factor 23 and Klotho: Physiology and Pathophysiology of an Endocrine Network of Mineral Metabolism," *Annu. Rev. Physiol.* 75:503-533 (2013)). A plethora of activities has been attributed to shed αKlotho$^{ecto}$, the bulk of which require a purported intrinsic glycosidase activity (Chang et al., "The Beta-Glucuronidase Klotho Hydrolyzes and Activates the TRPV5 Channel," *Science* 310(5747):490-493 (2005); Cha et al., "Removal of Sialic Acid Involving Klotho Causes Cell-Surface Retention of TRPV5 Channel Via Binding to Galectin-1,*" PNAS USA* 105(28):9805-9810 (2008); Hu et al., "Klotho: A Novel Phosphaturic Substance Acting as an Autocrine Enzyme in the Renal Proximal Tubule," *FASEB J.* 24(9):3438-3450 (2010); and Imura et al., "Alpha-Klotho as a Regulator of Calcium Homeostasis," *Science* 316(5831):1615-1618 (2007)).

Phosphate is essential to the basic machinery of the cell, where it exists either in organic form as a component of nucleic acids, membrane lipids, enzyme cofactors and nucleoside phosphates, or as inorganic hydroxyapatite, as the major component of vertebrate bone, teeth, and cartilage. Phosphate is also a key modification group in the modulation of enzyme activity, in energy metabolism and in cellular signaling (Razzaque, M. S., "Bone-kidney axis in systemic phosphate turnover," *Arch Biochem Biophys* 561:154-158 (2014)) Plasma levels of phosphate range between 2.2 and 4.9 mg/dl (Dwyer et al., "Severe Hypophosphatemia in Postoperative Patients," *Nutr Clin Pract* 7(6):279-283 (1992), Alon et al., "Calcimimetics as an Adjuvant Treatment for Familial Hypophosphatemic Rickets," *Clin J Am Soc Nephrol* 3: 658-664 (2008)), and are primarily regulated by modifying renal tubular reabsorption. Because of phosphate's pleiotropic activity, imbalances in phosphate homeostasis adversely affect essentially every major tissue/organ.

Hypophosphatemia is a common clinical condition with an incidence ranging from 0.2-3.1% in all hospital admissions to 21.5-80% in specific subgroups of hospitalized patients (Gaasbeek et al., "Hypophosphatemia: An Update on its Etiology and Treatment," *Am J Med* 118(10):1094-1101 (2005), Brunelli et al., "Hypophosphatemia: Clinical Consequences and Management.," *J Am Soc Nephrol* 18(7): 1999-2003 (2007)). Acute clinical manifestations of hypophosphatemia include respiratory failure, cardiac arrhythmia, hemolysis, rhabdomyolysis, seizures, and coma. Chronic clinical manifestations of hypophosphatemia include myalgia and osteomalacia (Gaasbeek et al., "Hypophosphatemia: An Update on its Etiology and Treatment," *Am J Med* 118(10):1094-1101 (2005)). Hypophosphatemia originates from diverse pathophysiologic mechanisms, most importantly from renal phosphate wasting, an inherited or acquired condition in which renal tubular reabsorption of phosphate is impaired (Imel et al., *"Fibroblast Growth Factor* 23: Roles in Health and Disease," *J Am Soc Nephrol* 16(9):2565-2575 (2005); Negri A., "Hereditary Hypophosphatemias: New Genes in the Bone-kidney Axis," *Nephrology (Carlton)* 12(4):317-320 (2007)). Hypophosphatemia can also be associated with alcoholic and diabetic ketoacidosis, acute asthma, chronic obstructive pulmonary disease, sepsis, recovery from organ transplantation, and the "refeeding syndrome," which refers to metabolic disturbances seen in malnourished patients on commencing nutrition (Gaasbeek et al., "Hypophosphatemia: An Update on its Etiology and Treatment," *Am J Med* 118(10):1094-1101 (2005), Miller et al., "Hypophosphatemia in the Emergency Department Therapeutics," *Am J Emerg Med* 18(4):457-461 (2000), Marinella M A., "Refeeding Syndrome and Hypophosphatemia," *J Intensive Care Med* 20(3):155-159 (2005)).

Oral or intravenous administration of inorganic phosphate salts is the current mainstay for the management of hypophosphatemia. Oral phosphate therapy requires high doses, which frequently lead to diarrhea or gastric irritation (Shiber et al., "Serum Phosphate Abnormalities in the Emergency Department," *J Emerg Med* 23(4):395-400 (2002)). For intravenous phosphate therapy, the response to any given dose is sometimes unpredictable (Bohannon N J., "Large Phosphate Shifts with Treatment for Hyperglycemia," *Arch Intern Med* 149(6):1423-1425 (1989), Charron et al., "Intravenous Phosphate in the Intensive Care Unit: More Aggressive Repletion Regimens for Moderate and Severe Hypophosphatemia," *Intensive Care Med* 29(8):1273-1278 (2003); Rosen et al., "Intravenous Phosphate Repletion Regimen for Critically Ill patients with Moderate Hypophosphatemia," *Crit Care Med* 23(7):1204-1210 (1995)), and complications include "overshoot" hyperphosphatemia, hypocalcemia, and metastatic calcification (Gaasbeek et al., "Hypophosphatemia: An Update on its Etiology and Treatment," *Am J Med* 118(10):1094-1101 (2005); Shiber et al., "Serum Phosphate Abnormalities in the Emergency Department," *J Emerg Med* 23(4):395-400 (2002)). In addition, parenteral regimens are not practical for chronic disorders. Most importantly, replacement therapy alone is never adequate when there is significant renal phosphate wasting. Therefore, novel strategies for the treatment of hypophosphatemia are needed.

Kidney transplantation is the preferred treatment of end-stage renal failure, and hypophosphatemia is a well recognized problem during the first weeks after engraftment. The majority of kidney transplant patients often experience excessive renal phosphate leakage (Schwarz et al., "Impaired Phosphate Handling of Renal Allografts is Aggravated under Rapamycin-based Immunosuppression," *Nephrol Dial Transplant* 16: 378-382 (2001); Moorhead et al., "Hypophosphataemic Osteomalacia after Cadaveric Renal Transplantation," *Lancet* 1(7860):694-697 (1974)), because the transplanted kidneys only marginally reabsorb the urinary phosphate to the circulation. The reasons for this poor reabsorbing activity on the part of transplanted kidneys are unknown. It frequently causes the patients malnutrition and secondary osteoporosis. This problem cannot be treated by a simple exogenous supplementation of phosphate. Similar renal phosphate leakage with unknown pathology is often observed in pediatric medicine, with outcomes such as malnutrition or growth retardation. A recent study in adults demonstrated that as many as 93% of patients develop moderate to severe hypophosphatemia (serum phosphate concentration 0.9-2.25 mg/dL), an average of 5 weeks following transplantation (Ambuhl et al., "Metabolic Aspects of Phosphate Replacement Therapy for Hypophosphatemia After Renal Transplantation: Impact on Muscular Phosphate Content, Mineral Metabolism, and Acid/base Homeostasis," *Am J Kidney Dis* 34:875-83 (1999)).

There remains a significant need for inhibition of the FGF23 pathway for the long-term treatment of phosphate metabolism and other disorders. The invention described herein marks a significant step forward in providing biologics for inhibiting FGF23 signaling in human inherited and acquired diseases that are associated with excessive FGF23 signaling.

The present invention is directed to overcoming these and other deficiencies in the art.

SUMMARY OF THE INVENTION

One aspect of the present invention relates to a modified soluble α-Klotho protein, where the modified soluble α-Klotho protein comprises a KL2 extracellular domain comprising a modification to substantially decrease or eliminate binding affinity for fibroblast growth factor receptor (FGFR)1c, FGFR3c, and/or FGFR4, as compared to a wildtype soluble α-Klotho protein.

Another aspect of the present invention relates to a modified soluble α-Klotho protein possessing a modification as compared to a wildtype soluble α-Klotho protein, where the modified soluble α-Klotho protein comprises an amino acid sequence at least 80% identical to the amino acid sequence of E34 to S932 of SEQ ID NO:2.

Yet another aspect of the present invention relates to an isolated fragment of wildtype soluble α-Klotho protein, where the isolated fragment comprises a fibroblast growth factor receptor (FGFR)1c binding domain and where the isolated fragment has no binding affinity for fibroblast growth factor (FGF)23, as compared to wildtype soluble α-Klotho protein.

A further aspect of the present invention relates to an isolated fragment of wildtype soluble α-Klotho protein, where the isolated fragment comprises an amino acid sequence at least 80% identical to the amino acid sequence of SEQ ID NO:3.

Yet a further aspect of the present invention relates to pharmaceutical compositions comprising the modified soluble α-Klotho protein(s) and/or fragment(s) of wildtype soluble α-Klotho protein described herein and a pharmaceutically acceptable carrier.

Another aspect of the present invention relates to isolated nucleic acid molecules encoding the modified soluble α-Klotho protein(s) or fragment(s) of wildtype soluble α-Klotho protein described herein.

Yet another aspect of the present invention is a vector comprising the nucleic acid molecule(s) described herein, as well as host cell(s) comprising the nucleic acid molecule(s) or the modified soluble α-Klotho protein(s) or fragment(s) of wildtype soluble α-Klotho protein described herein.

Yet another aspect of the present invention is directed to a method of treating a disease or disorder mediated by interaction of FGF23 with an FGFR/α-Klotho complex. The method involves administering to a patient in need thereof the modified soluble α-Klotho protein and/or the isolated fragment of wildtype soluble α-Klotho protein described herein.

Yet another aspect of the present invention is directed to a method of treating a renal phosphate wasting disorder. The method involves administering to a patient in need thereof the modified soluble α-Klotho protein and/or the isolated fragment of wildtype soluble α-Klotho protein described herein.

Yet another aspect of the present invention is directed to a method of treating autosomal dominant hypophosphatemic rickets (ADHR), X-linked hypophosphatemic rickets (XLH), tumor-induced osteomalacia (TIO), fibrous dysplasia (FD), or chronic kidney disease (CKD). The method involves administering to a patient in need thereof the modified soluble α-Klotho protein and/or the isolated fragment of wildtype soluble α-Klotho protein described herein.

Yet another aspect of the present invention is directed to a method of treating one or more complications of chronic kidney disease (CKD). The method involves administering to a patient in need thereof the modified soluble α-Klotho protein and/or the isolated fragment of wildtype soluble α-Klotho protein described herein.

Yet another aspect of the present invention is directed to a method of inhibiting FGF23/FGFR/α-Klotho ternary complex formation in a patient having a disease or disorder mediated by interaction of FGF23 with an FGFR/α-Klotho complex. The method involves administering to the patient the modified soluble α-Klotho protein and/or the isolated fragment of wildtype soluble α-Klotho protein described herein.

Yet another aspect of the present invention is directed to a method of inhibiting FGF23/FGFR/α-Klotho ternary complex formation in a patient having one or more complications of chronic kidney disease (CKD). The method involves administering to the patient the modified soluble α-Klotho protein and/or the isolated fragment of wildtype soluble α-Klotho protein described herein.

The aging suppressor αKlotho binds to the fibroblast growth factor receptor (FGFR). This commits FGFR to respond to FGF23, a key hormone in the regulation of mineral ion/vitamin D homeostasis. As described herein, to understand the molecular mechanism for this co-receptor function of αKlotho, the atomic structure of a 1:1:1 ternary complex consisting of the extracellular domain) (αKlotho$^{ecto}$) shed from membrane-anchored αKlotho into body fluids, the FGFR1c ligand-binding domain, and FGF23 was determined. In this complex, αKlotho simultaneously tethers FGFR1c by its D3 domain and FGF23 by its C-terminal tail, thus implementing FGF23-FGFR1c proximity and conferring stability. Significantly, it was found that anchoring of FGFR1c to the αKlotho co-receptor is mediated by a long β1α1 loop of KL2, termed the αKlotho "Receptor Binding Arm" (RBA), which protrudes as much as 35 Å away from the KL2 core and latches on to the FGFR1c D3 domain. Further, to functionally validate the crystallographically-deduced focal role of the RBA in mediating the co-receptor function of αKlotho, a mutant form of soluble αKlotho lacking a portion of the RBA (αKlotho$^{ecto/\Delta RBA}$, with the deleted portion of the RBA corresponding to L544 to T565 of SEQ ID NO:1) was generated, as set forth in the Examples. Consistent with the crystal structure, SEC-MALS analysis showed that deletion of RBA prevents αKlotho$^{ecto/\Delta RBA}$ from forming a binary complex with FGFR1c$^{ecto}$ but does not affect the ability of αKlotho$^{ecto/\Delta RBA}$ to form binary complex with FGF23. Because of this half functionality, the αKlotho$^{ecto/\Delta RBA}$ mutant acts as an FGF23 ligand trap, sequestering FGF23 into inactive FGF23-αKlotho$^{ecto/\Delta RBA}$ binary complexes. In doing so, the αKlotho$^{ecto/\Delta RBA}$ mutant competitively inhibits formation of wild-type αKlotho-FGF23 complexes and hence antagonizes the co-receptor activity of wild-type αKlotho both in vitro and in vivo. Specifically, measurements of FGFR activation using downstream ERK phosphorylation as readout showed that the αKlotho$^{ecto/\Delta RBA}$ mutant inhibits the ability of wild-type αKlotho$^{ecto}$ to promote FGF23 signaling in HEK293 cells in a dose-dependent manner. In normal mice αKlotho$^{ecto/\Delta RBA}$ consistently raised serum phosphate and suppressed Egr1 transcription in the kidney and the heart. Further, the RBA peptide fragment itself serves as an inhibitor of FGF23 signaling by binding FGFR and blocking ternary complex formation with αKlotho-FGF23 complexes.

BRIEF DESCRIPTION OF THE DRAWINGS

FIG. 1A is a cartoon (left) and surface representation (right) of the ternary complex structure. αKlotho KL1 and KL2 domains are identified and are joined by a short proline-rich linker. FGF23 is identified with its proteolytic cleavage motif outlined by the dashed-line box in gray. D2 and D3 of FGFR 1c are indicated. NT, N-terminus; CT, C-terminus. FIG. 1B illustrates the binding interfaces between αKlotho$^{ecto}$ and the FGF23-FGFR1c$^{ecto}$ complex. The ternary complex (center) is shown in two different orientations related by a 180° rotation along the vertical axis. FGF23-αKlotho$^{ecto}$ (is indicated) and FGFR1c$^{ecto}$-αKlotho$^{ecto}$ interfaces are visualized by pulling αKlotho$^{ecto}$ and FGF23-FGFR1c$^{ecto}$ complex away from each other. The separated components are shown to the left and right of the ternary complex.

FIG. 2A shows the triosephosphate isomerase (TIM) barrel topology of αKlotho KL1 and KL2 domains. KL1 is in the same orientation as in FIG. 1A, whereas KL2 has been superimposed onto KL1 and has thus been reoriented. The eight alternating β strands (indicated) and α helices (indicated) which define the TIM barrel are labeled according to the standard nomenclature for the TIM fold (Henrissat et al., "Structural and Sequence-Based Classification of Glycoside Hydrolases," *Curr. Opin. Struct. Biol.* 7 (5): 637-644 (1997), which is hereby incorporated by reference in its entirety). KL1 and KL2 differ dramatically in the conformation of the β1α1 loop (indicated). In KL2, this loop protrudes away from the TIM barrel and serves as a Receptor Binding Arm (RBA; FIG. 1). FIG. 2B shows the molecular surfaces of KLrP-glucosylceramide (Glc) (center; KLrP), KL1-Glc (left; KL1) and KL2-Glc (right; KL2). Binding of Glc to KL1 and KL2 was simulated by superimposing KL1 and KL2 onto KLrP-Glc. In all cases, Glc is indicated. The divergent conformation of the β6α6 loop (indicated) in KL1 almost seals off the entrance to the catalytic pocket, while the divergent conformations of β1α1 (RBA; indicated), β6α6 (indicated) and β8α8 (indicated) loops in KL2 leave the central barrel cavity in KL2 in a more solvent-exposed state that is less capable of ligating substrate (see also FIG. 10). FIG. 2C shows the glycosidase activity of (from left to right) αKlotho$^{ecto}$, β-glucuronidase, and sialidase. Bars: mean values; error bars: SD; dots: individual data points; n=3 independent experiments. RU, relative units.

FIG. 3A shows the ternary complex structure in surface representation. Coloring is the same as in FIG. 1A, except that the alternatively spliced region of FGFR 1c is shown below FGF23. Left boxes: perimeter of interface between distal tip of αKlotho Receptor Binding Arm (RBA) and the hydrophobic FGFR1c D3 groove. Right box: perimeter of αKlotho-FGF23$^{C-tail}$ interface. FIG. 3B shows that the RBA stretches out of the KL2 domain of αKlotho$^{ecto}$ and latches onto the FGFR1c D3 domain. Upper panel: interface between the distal tip of RBA and the D3 groove detailing hydrophobic interactions (transparent surfaces). Note that Leu342 (transparent surface) from the spliced region of the D3 groove is strictly conserved in "c" splice isoforms of FGFR1-3 and FGFR4 and is mutated in Kallmann syndrome (Pitteloud et al., "Digenic Mutations Account for Variable Phenotypes in Idiopathic Hypogonadotropic Hypogonadism," *J. Clin. Invest.* 117 (2): 457-463 (2007), which is hereby incorporated by reference in its entirety). Lower panel: Close-up view of the extended β sheet between the RBA-β1: RBA-β2 strand pair and the four-stranded β sheet in D3 (βC'-βC-βF-βG). This structure forms via hydrogen bonding (dashed (yellow) lines) between backbone atoms of RBA-β1 and D3-βC'. FIG. 3C shows that both KL domains of αKlotho$^{ecto}$ participate in tethering of the flexible C-terminal tail of FGF23 (FGF23$^{C-tail}$). FGF23$^{C-tail}$ residues Asp-188-Thr-200 thread through the KL1-KL2 cleft and the β-barrel cavity of KL2. Of these residues, Asp188-Leu-193 adopt a cage-like conformation that is partially stabilized by intramolecular hydrogen bonds (dashed lines protruding from the indicated residues). Dashed lines in the inset: intermolecular hydrogen bonds; transparent surfaces: hydrophobic interactions. Note that Tyr-433 from the KL1 α7 helix deep inside the KL1-KL2 cleft plays a prominent role in tethering the cage-like structure in the FGF23$^{C-tail}$ formed by Asp-188-Leu-193. Dashed circle (shown at greater magnification below): the KL1-KL2 interface where residues from both αKlotho domains jointly coordinate a Zn$^{2+}$ ion (indicated by the sphere).

FIG. 4A shows SEC-MALS analysis of FGFR1c$^{ecto}$ interaction with wild-type αKlotho$^{ecto}$ or its RBA deletion mutant. RU, relative units. FIGS. 4B-4E are representative immunoblots of phosphorylated ERK (upper panels) and total ERK (lower panels, done as sample loading controls) in total HEK293 cell lysates (n=3 independent experiments for each panel). FIG. 4B is an analysis of the effects of RBA deletion on the co-receptor activity of αKlotho$^{ecto}$ and αKlotho isoforms. FIG. 4C is an analysis of mutations in the αKlotho binding pocket that engages the FGF23$^{C-tail}$. FIG. 4D is an analysis of mutations in the FGF23$^{C-tail}$ that disrupt αKlotho-FGF23$^{C-tail}$ interaction. FIG. 4E is an analysis of mutations of the four Zn$^{2+}$-coordinating amino acids in αKlotho.

FIG. 5A shows SEC-MALS analysis of FGF23-FGFR 1c$^{ecto}$-αKlotho$^{ecto}$ complex in the absence or presence of heparin hexasaccharide (HS6) present at various molar ratios. FIG. 5B shows SEC-MALS analysis of FGF23-FGFR1c$^{ecto}$-αKlotho$^{ecto}$ complexes containing HS-binding site mutations of FGF23 and FGFR1c. FIGS. 5C-5E show representative immunoblots of phosphorylated ERK (top panels) and total ERK (bottom panels; sample loading controls) in total BaF3 cell lysates (n=3 independent experiments for each panel). FIG. 5C shows the analysis of HS dependency of FGF23 signaling. FIGS. 5D-5E shows the analysis of mutations in the HS-binding site of FGFR1c (FIG. 5D) and in the HS-binding site or secondary receptor-binding site of FGF23 (FIG. 5E). FIG. 5F shows SEC-MALS analysis of FGF23-FGFR1c$^{ecto}$-αKlotho$^{ecto}$ complexes containing a secondary receptor-binding site mutation in FGF23, a secondary ligand-binding site mutation in FGFR1c, or a direct receptor-receptor binding site mutation in FGFR1c. In FIG. 5B and FIG. 5F, wild-type ternary complex served as controls. FIG. 5G shows the molecular surface of a 2:2:2:2 FGF23-FGFR1c-αKlotho-HS dimer in two orientations related by a 90° rotation around the horizontal axis: a side-view looking parallel to the plane of a cell membrane (left) and a bird's-eye view looking down onto the plane of a cell membrane (right). HS molecules are indicated.

FIG. 6A shows the domain organization of membrane-bound αKlotho (αKlotho™) and its soluble isoform αKlotho$^{ecto}$ generated by an ectodomain shedding in the kidney (Chen et al., "Insulin Stimulates the Cleavage and Release of the Extracellular Domain of Klotho by ADAM10 and ADAM17," *PNAS USA* 104(50):19796-19801 (2007), which is hereby incorporated by reference in its entirety). KL1 and KL2: tandem domains with homology to family 1 glycosidases (Henrissat et al., "Structural and Sequence-Based Classification of Glycoside Hydrolases," *Curr. Opin. Struct. Biol.* 7(5):637-644 (1997), which is hereby incorporated by reference in its entirety). FIG. 6B shows representative immunoblots of phosphorylated ERK (top blots) and total ERK (bottom blots; sample loading control) in total HEK293 cell lysates (n=3 independent experiments). Upper panel: lysates from untransfected HEK293 cells that were pre-treated with a fixed αKlotho$^{ecto}$ concentration (10 nM) and then stimulated with increasing FGF23 concentrations, and lysates from HEK293-αKlotho™ cells treated with increasing concentrations of FGF23 alone. Lower panel: lysates from HEK293-αKlotho™ cells that were pre-treated with increasing αKlotho$^{ecto}$ concentrations and then stimulated with a fixed FGF23 concentration. FIG. 6C shows plasma phosphate, fractional excretion of phosphate, and phosphate excretion rate in wild-type mice before and after a single injection of αKlotho$^{ecto}$ (0.1 mg/kg BW) or isotonic saline alone (buffer) . Circles: mean values; error bars: SD; n=10 mice per group; * p<0.05, paired Student's t test. FIG. 6D shows relative Egr1 mRNA levels in the kidney of wild-type mice after a single injection with αKlotho$^{ecto}$ (0.1 mg/kg BW) or isotonic saline alone (buffer). Bars: mean values; error bars: SD; n=3 mice per group. The same batch of αKlotho$^{ecto}$ protein was used in the experiments shown in panels FIGS. 6B-6D.

FIG. 7A is a cartoon representation of 1:1:1 FGF23-FGFR 1c$^{ecto}$-αKlotho$^{ecto}$ complex in four different orientations related by 90° rotation. αKlotho domains KL1 and KL2 are indicated; KL1-KL2 linker is positioned between the KL1 and KL2 domains. FGFR1c and FGF23 are indicated. The ternary complex resembles an oblique rectangular prism with an average dimension of 100 Å×90 Å×50 Å. The long axes of αKlotho$^{ecto}$ and FGF23-FGFR1c complex in the ternary complex are each about 90 Å long, and parallel to one another such that the C-termini of FGFR 1c$^{ecto}$ and αKlotho$^{ecto}$ end up on the same side of the ternary complex, ready to insert into the cell membrane (bar). First N-acetyl glucosamine moiety (purple sticks) at six of the seven consensus N-linked αKlotho glycosylation sites could be built due to sufficient electron density. Asn-694 is the only glycosylation site that falls in the vicinity of a binding interface, namely αKlotho$^{ecto}$-FGF23. FIG. 7B is a close-up view of KL1-KL2 interdomain interface. Zinc-mediated contacts facilitate overall αKlotho$^{ecto}$ conformation. Dashed lines (yellow) in the inset: hydrogen bonds; gray transparent surfaces: hydrophobic contacts. FIG. 7C shows the emission energy spectrum obtained from excitation/emission scan of FGF23-FGFR 1c$^{ecto}$-αKlotho$^{ecto}$ crystal. Inset: expanded view of zinc fluorescence at 8,637 eV of emission energy.

FIG. 8A shows an open-book view of FGF23-FGFR 1c$^{ecto}$ complex interface. FGF23 (is indicated on the left) and FGFR 1c$^{ecto}$ (is indicated on the right) are pulled apart and rotated by 90° around the vertical axis to expose the binding interface (is indicated in dark grey). FIG. 8B shows ligand-receptor D3 and ligand-receptor D2-D3 linker interfaces of endocrine FGF23-FGFR1c and paracrine FGF9-FGFR1c (Liu et al., "Regulation of Receptor Binding Specificity of FGF9 by an Autoinhibitory Homodimerization," *Structure* 25 (9): 1325-1336 (2017), which is hereby incorporated by reference in its entirety) structures. Gray transparent surfaces: hydrophobic interactions; dashed lines: hydrogen bonds. Because FGF9 Arg-62 is replaced with glycine in FGF23 (Gly-38) and FGF9 Glu-138 is replaced with histidine in FGF23 (His-117), neither the side chain of Asp-125 in FGF23 (Asn-146 in FGF9), nor the side chain of invariant Arg-250 in the FGFR1c D2-D3 linker can be tethered through intramolecular hydrogen bonds. Thus, these side chains possess greater freedom of motion in the FGF23-FGFR1c complex, and as a result, hydrogen bonding between FGF23 and FGFR1c D2-D3 linker entails greater entropic cost, which generates less binding affinity. Substitution of Phe-140 and Pro-189 in FGF9 with hydrophilic Thr-119 and Ser-159 in FGF23 further diminishes the ability of FGF23 to gain binding affinity from hydrogen bonding with FGFR1c D2-D3 linker. A lack of contacts between FGF23 N-terminus and FGFR1c D3 cleft, which forms between alternatively spliced βC'-βE and βB'-βC loops (Belov et al., "Molecular Mechanisms of Fibroblast Growth Factor Signaling in Physiology and Pathology," *Cold Spring Harb. Perspect. Biol.* 5 (6): doi: 10.1101/cshperspect. a015958 (2013), which is hereby incorporated by reference in its entirety), likely further exacerbates FGF23's weak FGFR-binding affinity. FIG. 8C shows the ligand-receptor D2 interface in endocrine FGF23-FGFR1c and paracrine FGF9-FGFR1c (Liu et al., "Regulation of Receptor Binding Specificity of FGF9 by an Autoinhibitory Homodimerization," *Structure* 25 (9): 1325-1336 (2017), which is hereby incorporated by reference in its entirety) structures. Gray transparent surfaces: hydrophobic interactions; dashed lines: hydrogen bonds. Many contacts at this interface are conserved between paracrine FGFs and FGF23, and hence FGF23 gains much of its FGFR-binding affinity through these contacts. Three hydrogen bonds involving Asn-49, Ser-50, and His-66 of FGF23 are unique to the FGF23-FGFR1c complex.

FIGS. 9A-9E show the structural basis for FGFR isoform specificity of αKlotho and FGF23. FIG. 9A shows a structure-based sequence alignment of a segment of FGFR D3 (SEQ ID NOs: 14-20 for FGFR1b, 1c, 2b, 2c, 3b, 3c, and 4, respectively). The alternatively spliced regions of all seven FGFRs are boxed with a rectangle. β strand locations above the alignment are indicated as light grey arrows (constant region) and dark grey arrows (alternatively spliced region). A leucine (boxed) of hydrophobic groove residues (lightly highlighted) in the alternatively spliced region is conserved only among "c" isoforms of FGFR1-3 and FGFR4, which explains αKlotho binding selectivity for these receptors. FIG. 9B shows the interface between FGF23 and the BF-BG loop of FGFR1c D3 in the FGF23-FGFR1c structure of the ternary complex. Backbone atoms of His-117 and Gly-81 in FGF23 make specific hydrogen bonds with Ser-346 side-chain and Asn-345 backbone atoms of the BF-BG loop. Serine corresponding to Ser-346 in FGFR1c (indicated) is conserved only among "c" isoforms of FGFR1-3 and FGFR4 (see panel FIG. 9A). FIG. 9C show representative immunoblots of phosphorylated ERK (top blot) and total ERK (bottom blot; sample loading control) in total BaF3 cell lysates (n=3 independent experiments). FIG. 9D show cartoon representations of four paracrine FGF-FGFR complex structures (Shimada et al., "Targeted Ablation of Fgf23 Demonstrates an Essential Physiological Role of FGF23 in Phosphate and Vitamin D Metabolism," *J. Clin. Invest.* 113 (4): 561-568 (2004); Gattineni et al., "FGF23 Decreases Renal NaPi-2a and NaPi-2c Expression and Induces Hypophosphatemia In Vivo Predominantly Via FGF Receptor 1," *Am. J. Physiol. Renal Physiol.* 297 (2): F282-291 (2009); Lemmon et al., "Cell Signaling by Receptor Tyrosine Kinases," *Cell* 141 (7): 1117-1134 (2010); and Schlessinger et al., "Crystal Structure of a Ternary FGF-FGFR-Heparin Complex Reveals a Dual Role for Heparin in FGFR Binding and Dimerization," *Mol. Cell* 6 (3): 743-750 (2000), each of which is hereby incorporated by reference in its entirety). Solid black oval: hydrophobic D3 groove. Dashed black circle: second binding pocket (SBP) for αKlotho in D3. While the hydrophobic groove is engaged by FGF8 (see also FIG. 9E), the SBP is not utilized in any of the current paracrine FGF-FGFR structures. In most paracrine FGF-FGFR structures, the βC-βC' loop is disordered (indicated with dashed lines) since it does not participate in FGF binding. Evidently, SBP and βC-βC' loop in D3 have evolved to mediate αKlotho binding to FGFR. FIG. 9E shows that αKlotho and FGF8b both bind to the hydrophobic groove in FGFR1c D3. FGF8b (indicated and dark grey) from the FGF8b-FGFR2c structure (Lemmon et al., "Cell Signaling by Receptor Tyrosine Kinases," *Cell* 141 (7): 1117-1134 (2010), which is hereby incorporated by reference in its entirety) was superimposed onto FGF23 in the FGF23-FGFR1c$^{ecto}$-αKlotho$^{ecto}$ complex. The αN helix of FGF8b occupies the same binding pocket in FGFR1c D3 as the distal tip of αKlotho RBA.

FIGS. 10A-10D show that αKlotho is the first non-enzymatic scaffold among TIM barrel proteins. FIG. 10A is a structure-based sequence alignment of TIM barrels of αKlotho KL1 and KL2 domains (residues of SEQ ID NO:1) and Klotho Related Protein (KLrP, SEQ ID NO:21). Most glycoside hydrolases (GH), a functionally diverse group of enzymes that cleave glycosidic bonds of complex carbohydrates on glycoproteins (Henrissat et al., "Structural and Sequence-Based Classification of Glycoside Hydrolases," *Curr. Opin. Struct. Biol.* 7 (5): 637-644 (1997), which is hereby incorporated by reference in its entirety), adopt TIM barrel fold. Locations and lengths of TIM barrel β-strands and α-helices are indicated above the alignment. Among GH family 1 members of the Klotho subfamily, only KLrP has a verified glycosylceramidase activity (Hayashi et al., "Klotho-Related Protein is a Novel Cytosolic Neutral Beta-Glycosylceramidase," *J. Biol. Chem.* 282 (42): 30889-30900 (2007), which is hereby incorporated by reference in its entirety), and E165 and E373 are its catalytically essential glutamic acids. KLrP residues Q17, H110, F111, E165, N164, N167, V168, V171, M172, L176, M178, F179, Y191, A194, F225, V227, L229, A246, F249, H250, L253, F254, Y308, Y309, I314, I326, L327, I332, F334, W345, E373, E424, W417, W425, and F433 colored cyan participate in substrate recognition/hydrolysis. αKlotho KL1 residues F377, Q378, E400, P401, W426, F427, K138, Y141, Y142, K145, F146 and αKlotho KL2 residues R693, N694, M695, D733, I735, V752, D756, I812, E819, D820, I822, K823, Y824, D826, Y827, Q831, E832, M833, T834, I836, N840, Q844, G378, L379, H380, A381, and D419 bind FGF23, and αKlotho residues of the KL2 β1α1 loop (D535, S539, Q540, F541, T542, D543, N545, V546, Y547, L548, W549, D550, V551, H552, H553, K555, L557, I558, V564, K566, R568, Y571, V573, and A576 of SEQ ID NO:1) highlighted grey within the box interact with the FGFR1c D3 domain. FIG. 10B shows the superimposition of KL1 Cα trace (dark gray) onto that of KLrP (light gray). Superimposition RMSD is 1.08 Å. Structurally most divergent regions between KL1 and KLrP are in cartoon representation. Glucose moiety and aliphatic chains of glucosylceramide (KLrP substrate) are in sticks. Catalytically essential Glu-165 in KLrP is replaced by an asparagine in KL1. Hydrophobic residues from KL1 β6-α6 loop occupy the pocket that accommodates the aliphatic chains of glucosylceramide in KLrP. KL1 N-terminus supports KL1-KL2 cleft formation (FIG. 7A) and KL1 β6-α6 loop conformation contributes to a key portion of the binding pocket in this cleft for the FGF23 C-terminal tail (FIG. 3C). FIGS. 10C-10D show the superimposition of KL2 Cα trace (dark gray) onto that of KLrP (light gray). Superimposition RMSD is 1.37 Å. Structurally divergent β1α1 (FIG. 10C), β6α6 and β8α8 (FIG. 10D) loops of KL2 and KLrP are rendered in cartoon. β1α1 loop in KL2 is disengaged from the central TIM barrel and stretches away from it by as much as 35 Å. Catalytically essential Glu-373 in KLrP is replaced by a serine in KL2. KLrP residues from β6α6 and β8α8 loops bind glucosylceramide (KLrP substrate); for example, W345 in the β6α6 loop and E424 and W425 in the β8α8 loop. Sequence divergence (panel a) and altered loop conformations are incompatible with glucosylceramide coordination by KL2. β1α1, β6α6 and β8α8 loops lie at the rim of the catalytic mouth in the TIM barrel (see FIG. 2B). Divergent conformations of these three loops in KL2 result in significant widening of the central barrel cavity in KL2, which merges with the KL1-KL2 cleft to form an expansive basin that accommodates the distal portion of the FGF23 C-terminal tail.

FIG. 11A shows a partial view of the ternary complex. αKlotho$^{ecto}$ (αKlotho$^{ecto}$ KL1 domain is indicated, αKlotho$^{ecto}$ KL2 domain and the receptor binding arm (RBA) is shown, FGF23 (indicated), FGFR1c (constant region: is indicated; alternatively splice region: is shown as a dark grey). Dashed black circle: perimeter of the interface between proximal end of αKlotho RBA and a second binding pocket (SBP) in FGFR1c D3 next to the hydrophobic groove. Solid black box: perimeter of αKlotho-FGF23$^{core}$ interface. FIG. 11B is a close-up view of the interface between proximal end of RBA and SBP in D3. Disulfide bridge between Cys-572 (N-terminal end of RBA) and Cys-621 (α2 helix) at the base of the RBA likely imparts some degree of conformational rigidity to the proximal RBA portion, whereas the conformation of the distal RBA tip is dictated by contacts with FGFR1c D3. FIG. 11C is a close-up view of the αKlotho-FGF23$^{core}$ interface detailing hydrogen bonding (upper panel) and hydrophobic contacts (lower panel). Gray transparent surfaces: hydrophobic interactions; dashed lines: hydrogen bonding contacts.

FIG. 12A shows plasma phosphate and fractional excretion of phosphate in wild-type mice before and after a single injection of αKlotho$^{ecto}$ (0.1 mg/kg BW), mutant αKlotho$^{ecto/\Delta RBA}$ (0.1 mg/kg BW), or isotonic saline alone (buffer). Circles: mean values; error bars: SD; n=6 mice per group; p: significance value determined by a paired Student's t test. FIG. 12B shows relative Egr1 mRNA levels in the kidney of wild-type mice injected once with αKlotho$^{ecto}$ (0.1 mg/kg BW; n=3), mutant αKlotho$^{ecto/\Delta RBA}$ (0.1 mg/kg BW; n=4), or isotonic saline alone (buffer; n=3). Bars: mean values; error bars: SD. FIG. 12C shows representative elution profiles of FGF23/αKlotho$^{ecto}$ and FGF23/αKlotho$^{ecto/\Delta RBA}$ mixtures from a size-exclusion column and representative Coomassie Brilliant Blue-stained SDS-polyacrylamide gels of eluted protein peak fractions. FIG. 12D shows the results of a thermal shift assay of αKlotho$^{ecto}$ and αKlotho$^{ecto/\Delta RBA}$ mutant in the presence and absence of FGF23 C-terminal tail peptide (FGF23$^{C\text{-}tail}$) (n=3 independent experiments). Increased melting temperatures in the presence of the FGF23$^{C\text{-}tail}$ indicate interaction of both αKlotho$^{ecto}$ proteins with the peptide. Higher melting temperature of αKlotho$^{ecto/\Delta RBA}$ mutant relative to wild-type αKlotho$^{ecto}$ indicates greater stability of the mutant protein. FIG. 12E shows representative immunoblots of phosphorylated ERK (top blot) and total ERK (bottom blot; sample loading control) in total lysates from HEK293-αKlotho™ cells co-stimulated with a fixed FGF23 concentration and increasing αKlotho$^{ecto/\Delta RBA}$ concentrations (n=3 independent experiments). αKlotho$^{ecto/\Delta RBA}$ mutant inhibits FGF23-induced ERK phosphorylation due to sequestering FGF23 into inactive FGF23-αKlotho$^{ecto/\Delta RBA}$ binary complexes. This also explains why αKlotho$^{ecto/\Delta RBA}$ injection into mice causes an increase in plasma phosphate (FIG. 12A) concomitant with renal Egr1 gene repression (FIG. 12B).

FIG. 13A shows a 2:2:2:1 FGF23-FGFR 1c$^{ecto}$-αKlotho$^{ecto}$-HS quaternary dimer in two orientations related by a 90° rotation around the horizontal axis. The dimer was constructed by superimposing FGF23 from two copies of 1:1:1 FGF23-FGFR1c$^{ecto}$-αKlotho$^{ecto}$ complex onto the two FGF1 molecules in the 2:2:1 FGF1-FGFR2c-HS dimer (Pellegrini et al., "Crystal Structure of Fibroblast Growth Factor Receptor Ectodomain Bound to Ligand and Heparin," Nature 407 (6807): 1029-1034 (2000); Harmer et al., "Towards a Resolution of the Stoichiometry of the Fibroblast Growth Factor (FGF)-FGF Receptor-Heparin Complex," J. Mol. Biol. 339 (4): 821-834 (2004); Robinson et al., "Cooperative Dimerization of Fibroblast Growth Factor 1 (FGF1) Upon a Single Heparin Saccharide May Drive the Formation of 2:2:1 FGF1.FGFR2c.Heparin Ternary Complexes," J. Biol. Chem. 280 (51): 42274-42282 (2005); Goodger et al., "Evidence That Heparin Saccharides Promote FGF2 Mitogenesis Through Two Distinct Mechanisms," J. Biol. Chem. 283 (19): 13001-13008 (2008), each of which is hereby incorporated by reference in its entirety). The dimer is held together solely by HS, which bridges two FGF23 molecules in trans. Left boxed surface: location of Ala-171, Ile-203, and Val-221 of FGFR1c, the mutation of which impairs the ability of HS to induce 2:2:2:2 quaternary dimer formation (FIG. 5F). Right boxed region: location of Met-149, Asn-150, and Pro-151 of FGF23, the mutation of which diminishes HS-induced quaternary dimerization (FIGS. 5E-5F). None of these residues plays any role in 2:2:2:1 quaternary dimer formation, and hence, contrary to experimental evidence (FIG. 5), mutation of these residues should not impact HS-induced FGF23-FGFR 1c$^{ecto}$-αKlotho$^{ecto}$ dimerization. FIG. 13B shows a 2:2:2:2 FGF23-FGFR 1c$^{ecto}$-αKlotho$^{ecto}$-HS quaternary dimer in two orientations related by a 90° rotation around the horizontal axis. See also FIG. 5G. The dimer was constructed by superimposing FGF23 from two copies of 1:1:1 FGF23-FGFR 1c$^{ecto}$-αKlotho$^{ecto}$ complex onto the two FGF2 molecules in the 2:2:2 FGF2-FGFR1c-HS dimer (Schlessinger et al., "Crystal Structure of a Ternary FGF-FGFR-Heparin Complex Reveals a Dual Role for Heparin in FGFR Binding and Dimerization," Mol. Cell 6 (3): 743-750 (2000), which is hereby incorporated by reference in its entirety). Insets: close-up views of the secondary FGF-FGFR (upper inset) and direct FGFR-FGFR (lower inset) interfaces. Gray transparent surfaces: hydrophobic interactions. Mutation of Ala-171, Ile-203, and Val-221 (indicated) impairs the ability of HS to dimerize FGF23-FGFR 1c$^{ecto}$-αKlotho$^{ecto}$ ternary complex (FIG. 5F).

FIGS. 15A-15C show that βKlotho-dependent FGFR activation by FGF19/FGF21 is mechanistically similar to αKlotho-dependent FGFR activation by FGF23. FIG. 15A shows a structure-based sequence alignment of portions of endocrine FGFs (SEQ ID NOs: 25-27 for FGF23, 21, and 19, respectively). β-strands and αC helix comprising the atypical β-trefoil core of FGF23 are indicated above the alignment. Asterisks and dots below the alignment denote sequence identity and similarity, respectively. Scissor symbols mark inactivating proteolytic cleavage sites in FGF23 and FGF21 (Dunshee et al., "Fibroblast Activation Protein Cleaves and Inactivates Fibroblast Growth Factor 21," J. Biol. Chem. 291 (11): 5986-5996 (2016), which is hereby incorporated by reference in its entirety). RXXR cleavage motif in FGF23 is in bold letters. FGFR1c-binding residues Y25, P26, N27, S29, P30, Y43, A47, R48, N49, S50, H52, P65, H66, M74, I75, R76, S77, E78, D79, A80, G81, V83, V84, T86, Y93, F108, H117, Q118, T119, N122, G123, Y124, D125, L158, S159, R160, E163 of FGF23 are shown, αKlotho-binding residues L39, V88, M89, L166, I167, F169, N170, P172, R187, D188, P189, L190, N191, V192, L193, K194, P195, R196, R198, M199, and T200 are shown. Vertical arrow marks the C-terminal boundary of the FGF23 variant used to solve the FGF23-FGFR 1c$^{ecto}$-αKlotho$^{ecto}$ complex structure. Five residues at the distal C-terminal region of FGF19/FGF21 (FGF21 residues R203, S204, P205, S206, and Y207; FGF19 residues R210, S211, P212, S213, and F214) (shown in black/gray) mediate binding of FGF19/FGF21 to βKlotho. These residues completely diverge from the αKlotho-binding residues in the FGF23 C-terminal tail. αKlotho-binding residues in the FGF23 core also are not conserved in FGF19/FGF21. FIG. 15B shows representative immunoblots of phosphorylated ERK (top blot) and total ERK (bottom blot; sample loading control) in total lysates from HEK293 cells expressing wild-type or mutant βKlotho™ (n=3 independent experiments). Similar to αKlotho$^{ARBA}$, βKlotho$^{ARBA}$ failed to support FGF21-induced FGFR activation, and βKlotho$^{L394P}$ and βKlotho$^{M435Y}$ mutants also had greatly diminished ability to promote FGF21 signaling. Thus, βKlotho tethers FGFR1c and FGF21 to itself in a manner similar to that identified for αKlotho to enable FGF21 signaling. FIG. 15C shows representative immunoblots of phosphorylated ERK (top blot) and total ERK (bottom blot; sample loading control) in total lysates from BaF3 cells expressing FGFR1c and βKlotho™ (n=3 independent experiments). Like αKlotho, βKlotho also requires heparin to support FGF21-mediated FGFR1c activation.

DETAILED DESCRIPTION OF THE INVENTION

Modified Soluble α-Klotho Proteins

Figures 1A, 1B:
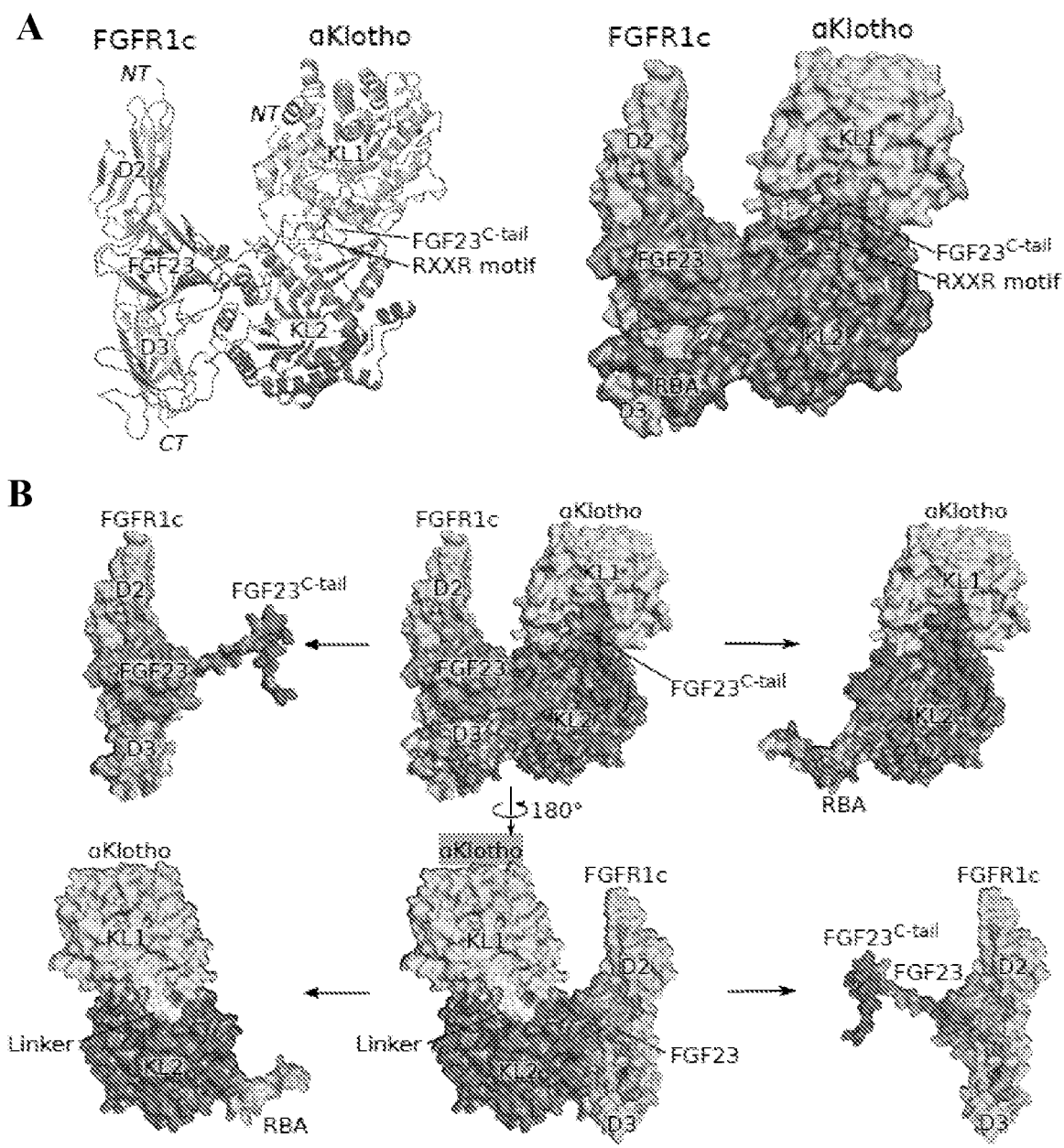
FIGS. 1A-1B show the overall topology of the FGF23-FGFR 1c$^{ecto}$-αKlotho$^{ecto}$ complex.

One aspect of the present invention relates to a modified soluble α-Klotho protein, where the modified soluble αKlotho protein comprises a KL2 extracellular domain comprising a modification to substantially decrease or eliminate binding affinity for fibroblast growth factor receptor (FGFR)1c, FGFR3c, and/or FGFR4, as compared to a wildtype soluble α-Klotho protein.

Also encompassed are fragments (e.g., active fragments) of the modified soluble α-Klotho proteins described herein. An active fragment is one that has the ability to bind FGF23 protein or polypeptide. Reference to modified soluble α-Klotho protein herein refers to modified soluble α-Klotho protein and fragments thereof.

As discussed above, αKlotho, fortuitously discovered as an aging suppressor gene (Kuro-o et al., "Mutation of the Mouse Klotho Gene Leads to a Syndrome Resembling Ageing," *Nature* 390(6655):45-51 (1997), which is hereby incorporated by reference in its entirety), is a single-pass transmembrane protein with an extracellular domain (also sometimes referred to as ectodomain) composed of two tandem domains (KL1 and KL2), each with significant homology to family 1 glycosidases (Henrissat et al., "Structural and Sequence-Based Classification of Glycoside Hydrolases," *Curr. Opin. Struct. Biol.* 7(5):637-644 (1997), which is hereby incorporated by reference in its entirety). Cleavage of full-length, membrane-bound α-Klotho (α-Klotho$^{transmembrane}$™) by ADAM proteases (van Loon et al., "Shedding of Klotho by ADAMs in the Kidney," *Am J Physiol Renal Physiol* 309: F359-368 (2015); Lindberg et al., "The Kidney is the Principal Organ Mediating Klotho Effects," *J Am Soc Nephrol* 25: 2169-2175 (2014), each of which is hereby incorporated by reference in its entirety) in kidney distal tubules sheds the α-Klotho ectodomain. Wild-type soluble α-Klotho protein as used herein refers to the ectodomain (or extracellular domain) of full-length wildtype membrane-bound α-Klotho protein.

As used herein, an unmodified or wildtype soluble α-Klotho protein as referred to herein refers to the ectodomain or extracellular domain of a human wildtype α-Klotho protein. Nucleotide and amino acid sequences of a human wildtype α-Klotho protein are found in the GenBank Accession Nos. NM 004795 and NP 004786 as well as in AB005142.1 and BAA23382.1, respectively, which are hereby incorporated by reference in their entirety. In certain embodiments, wildtype soluble α-Klotho protein as referred to herein is the ectodomain of wildtype human α-Klotho protein (SEQ ID NO: 1), as set forth below:

```
Soluble human α-Klotho (α-Klotho^ecto) (signal peptide underlined, FGF
Receptor Binding Arm (RBA) bold underline; KL2 domain (LEGTF . . . GFPGP)
italic shaded)
                                                              (SEQ ID NO: 1)
MPASAPPRRPRPPPPSLSLLLVLLGLGGRRLRAEPGDGAQTWARVSRPPAPEAAGLFQGTFPDGFLWAVGSAAYQ

TEGGWQQHGKGASIWDTFTHHPLAPPGDSRNASLPLGAPSPLQPATGDVASDSYNNVFRDTEALRELGVTHYRFS

ISWARVLPNGSAGVPNREGLRYYRRLLERLRELGVQPVVTLYHWDLPQRLQDAYGGWANRALADHFRDYAELCFR

HFGGQVKYWITIDNPYVVAWHGYATGRLAPGIRGSPRLGYLVAHNLLLAHAKVWHLYNTSFRPTQGGQVSIALSS

HWINPRRMTDHSIKECQKSLDFVLGWFAKPVFIDGDYPESMKNNLSSILPDFTESEKKFIKGTADFFALCFGPTL

SFQLLDPHMKFRQLESPNLRQLLSWIDLEFNHPQIFIVENGWFVSGTTKRDDAKYMYYLKKFIMETLKAIKLDGV

DVIGYTAWSLMDGFEWHRGYSIRRGLFYVDFLSQDKMLLPKSSALFYQKLIEKNGFPPLPENQPLEGTFPCDFAW

GVVDNYIQVDTTLSQFTDLNVYLWDVHHSKRLIKVDGVVTKKRKSYCVDFAAIQPQIALLQEMHVTHFRFSLDWA

SILPTGNLSQVNHTILQYYRCMASELVRVNITPVVALWQPMAPNQGLPRLLARQGAWENPYTALAFAEYARLCFQ

ELGHHVKLWITMNEPYTRNMTYSAGHNLLKAHALAWHVYNEKFRHAQNGKISIALQADWIEPACPFSQRDKEVAE

RVLEFDIGWLAEPIFGSGDYPWVMRDWLNQRNNFLLPYFTEDEKKLIQGTFDFLALSHYTTILVDSEKEDPIKYN

DYLEVQEMTDITWLNSPSQVAVVPWGLRKVLNWLKFKYGDLPMYIISNGIDDGLHAEDDQLRVYYMQNYINEALK

AHILDKINLCGYFAYSFNDRTAPRFGLYRYAADQFEPKASMKHYRKIIDSNGFPGPETLERFCPEEFTVCTECSF

FHTRKS.
```

In certain embodiments, the wildtype soluble α-Klotho protein excludes the above-noted signal peptide and comprises the mature wildtype soluble α-Klotho protein sequence having an amino acid sequence from residue E34 to S981 of SEQ ID NO:1.

Figure 10A:
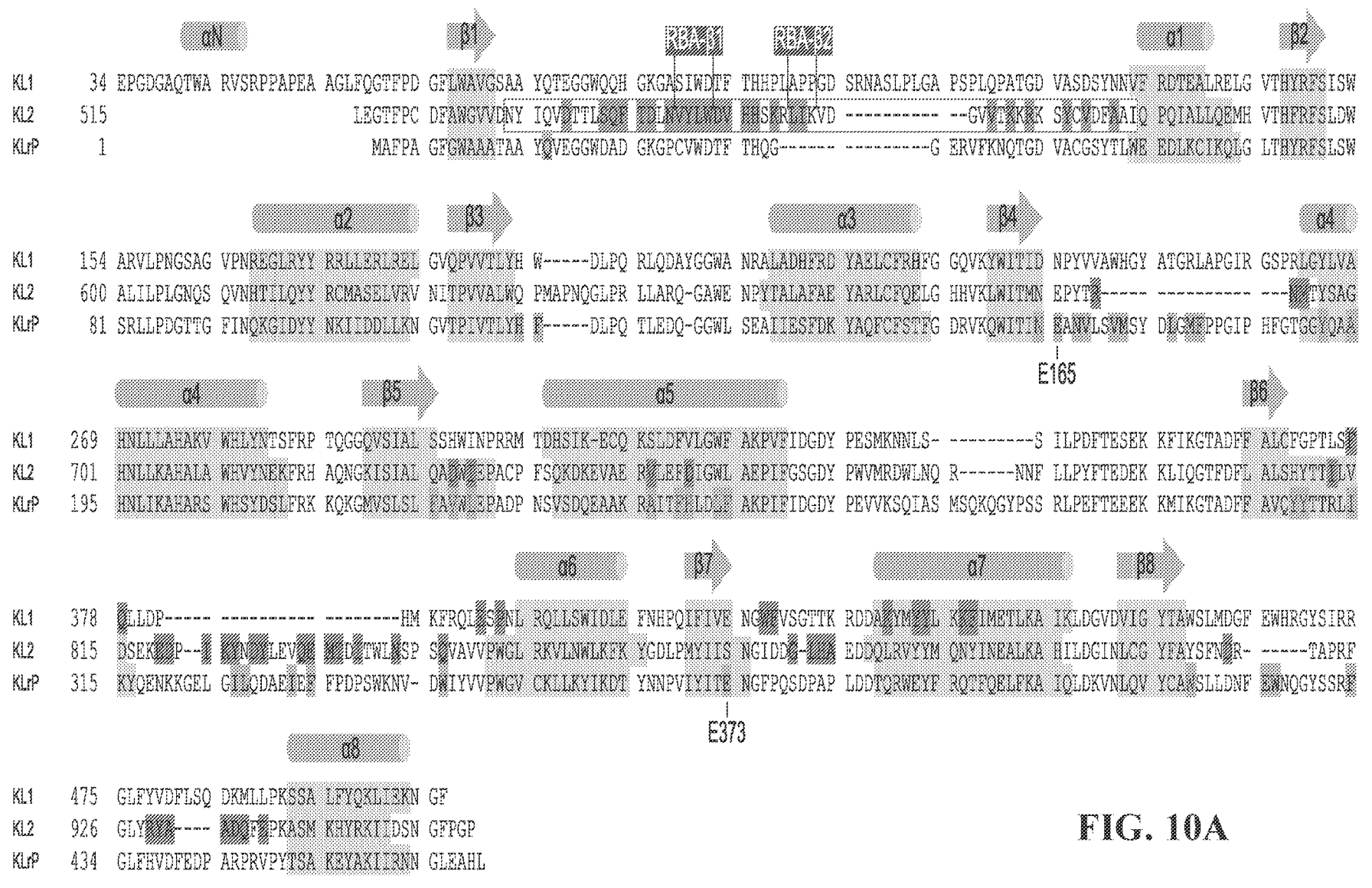
Figure 10B:
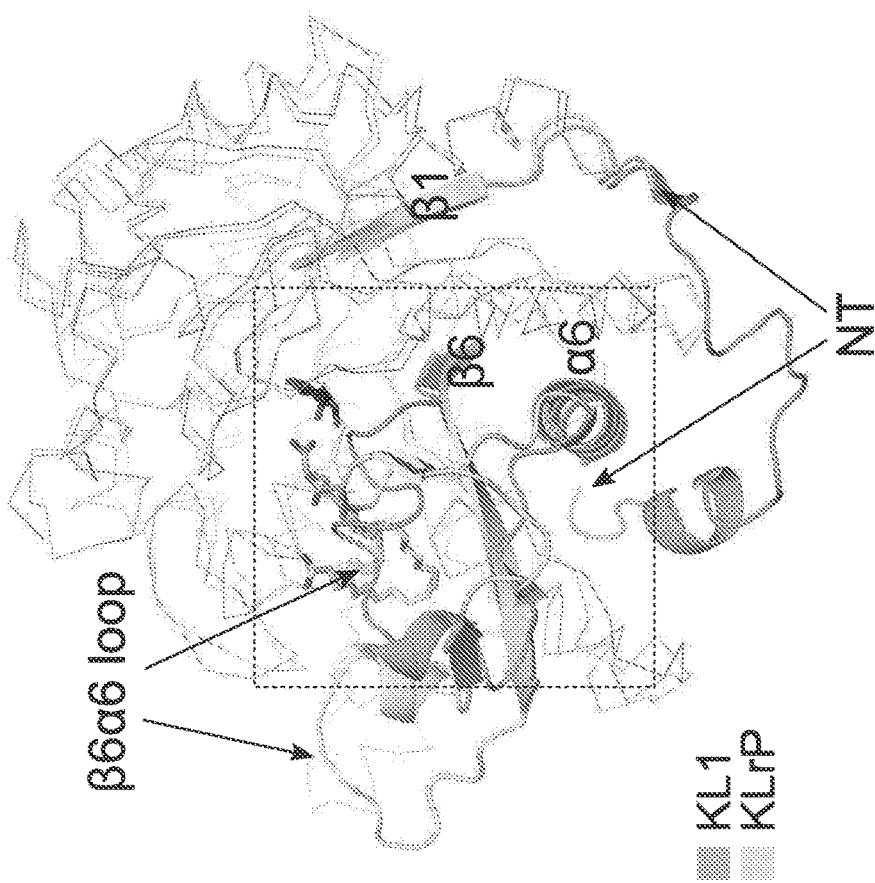
Figure 10B:
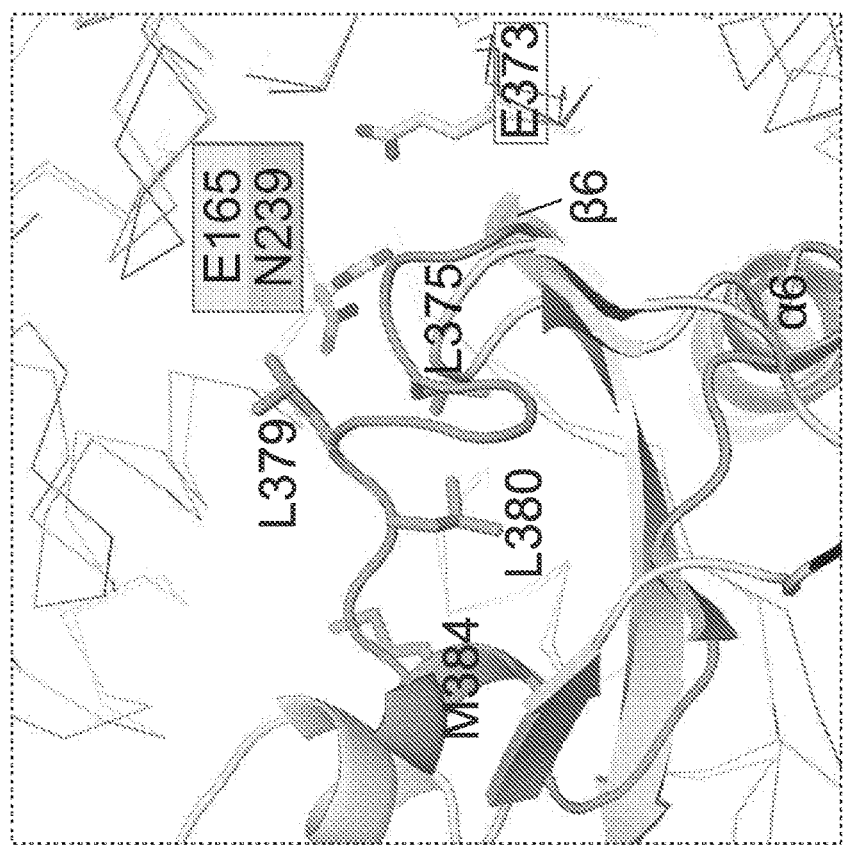
Figures 10C, 10D:
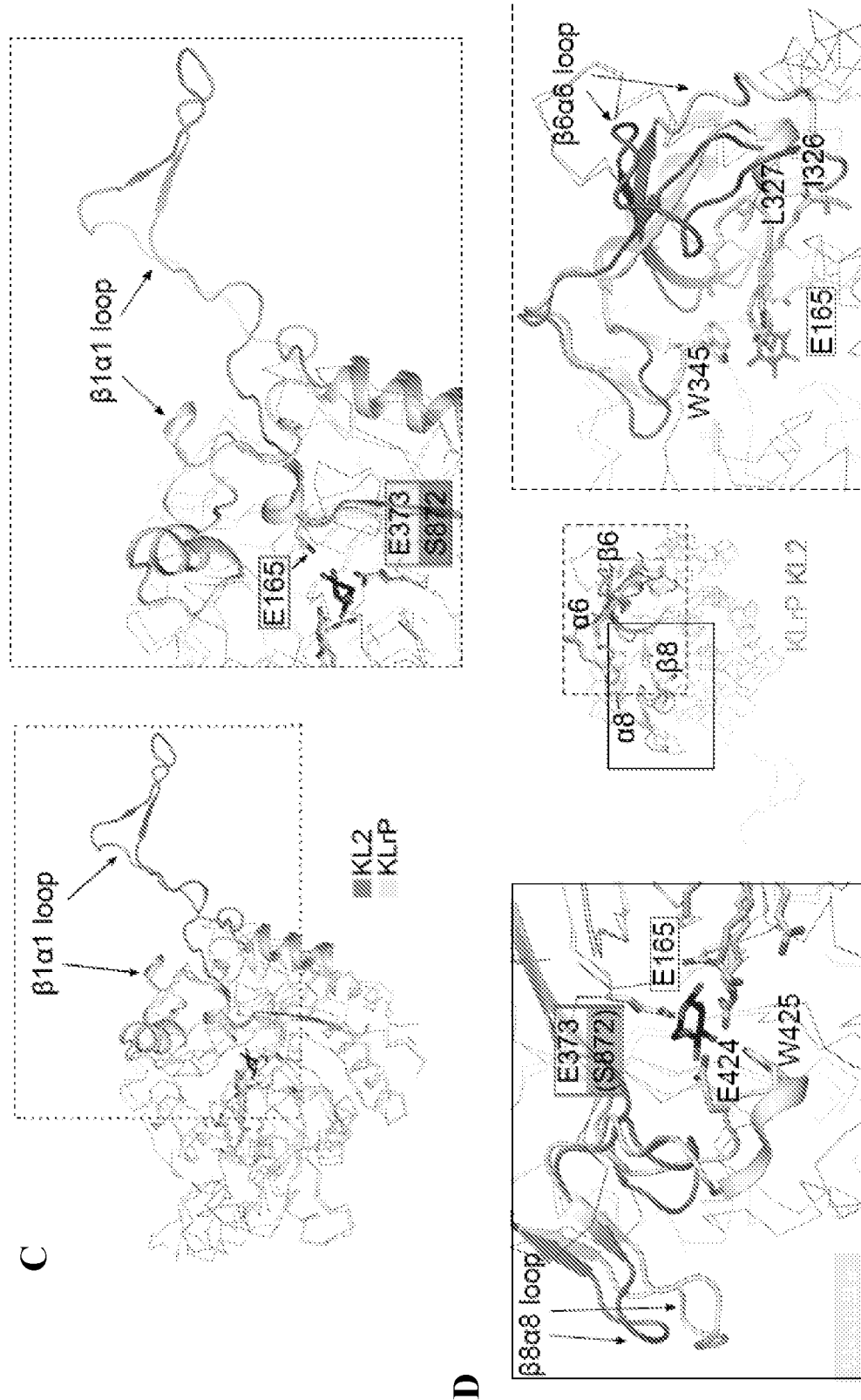
Figure 14:
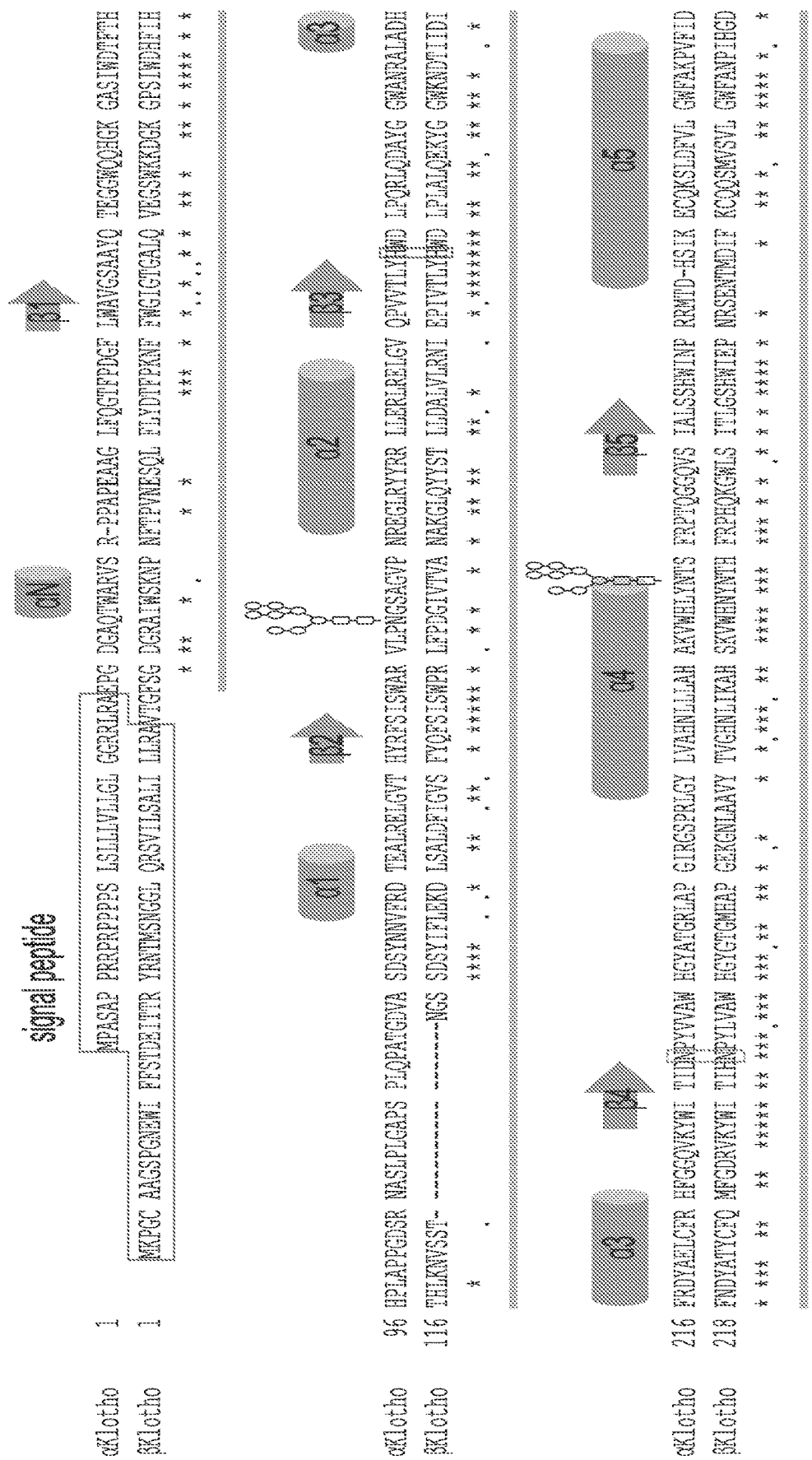
FIG. 14 shows FGF19/FGF21 co-receptor βKlotho is a non-enzymatic scaffold protein analogous to αKlotho. Structure-based sequence alignment of αKlotho (SEQ ID NO:22) and βKlotho (SEQ ID NO:23). The locations of the eight alternating β-strands and α-helices of the TIM fold are indicated above the alignment. Light grey, dark grey, and very light grey bars below the alignment mark the domain boundaries of KL1, KL2, and KL1-KL2 linker. Asterisks denote sequence identity and dots denote sequence similarity. Scissor symbols mark the four proposed sites of αKlotho cleavage by ADAM proteases/secretases. Cleavage 1, which coincides with the end of the rigid core of KL2, results in shedding of the entire αKlotho ectodomain from the cell membrane. While this cleavage product is a functional co-receptor, the αKlotho fragments generated by cleavages 2, 3, and 4 would be devoid of co-receptor activity. Black triangle: site where alternative splicing replaces the C-terminal KL2 sequence with a 15-residue-long unrelated sequence (SEQ ID NO:24). Glycan chain symbols: seven predicted N-linked glycosylation sites. $Zn^{2+}$-chelating residues I426, C739, D745, and D815 of αKlotho are shown, FGFR1c-binding residues D535, S539, Q540, F541, T542, D543, N545, V546, Y547, L548, W549, D550, V551, H552, H553, K555, L557, I558, V560, V564, K566, R568, Y571, V573, and A576 are shown, and FGF23-binding residues F377, Q378, E390, P392, W417, F418, K429, Y432, Y433, K436, F437, R693, N694, M695, D733, I735, V752, D756, I812, E819, D820, I822, K823, Y824, D826, Y827, Q831, E832, M833, T834, I836, N840, Q844, G878, L879, H890, A891, D919, R929, Y930, A931, A932, D933, Q934, and E936 are shown. Light box: β1α1 loop sequence in KL2 termed RBA. βKlotho RBA is about as long as Klotho RBA, and key FGFR-binding residues are conserved between these two RBAs, which is consistent with the similar FGFR-binding specificity of αKlotho and βKlotho (Urakawa et al., "Klotho Converts Canonical FGF Receptor Into a Specific Receptor for FGF23," Nature 444 (7120): 770-774 (2006) and Kurosu et al., "Regulation of Fibroblast Growth Factor-23 Signaling by Klotho," J. Biol. Chem. 281 (10): 6120-6123 (2006), which is hereby incorporated by reference in its entirety). But αKlotho residues in the binding pockets for the FGF23 C-terminal tail are not conserved in βKlotho, conforming to major sequence differences between the C-terminal tails of FGF23 and FGF19/FGF21 (FIG. 15A).
Figure 14:
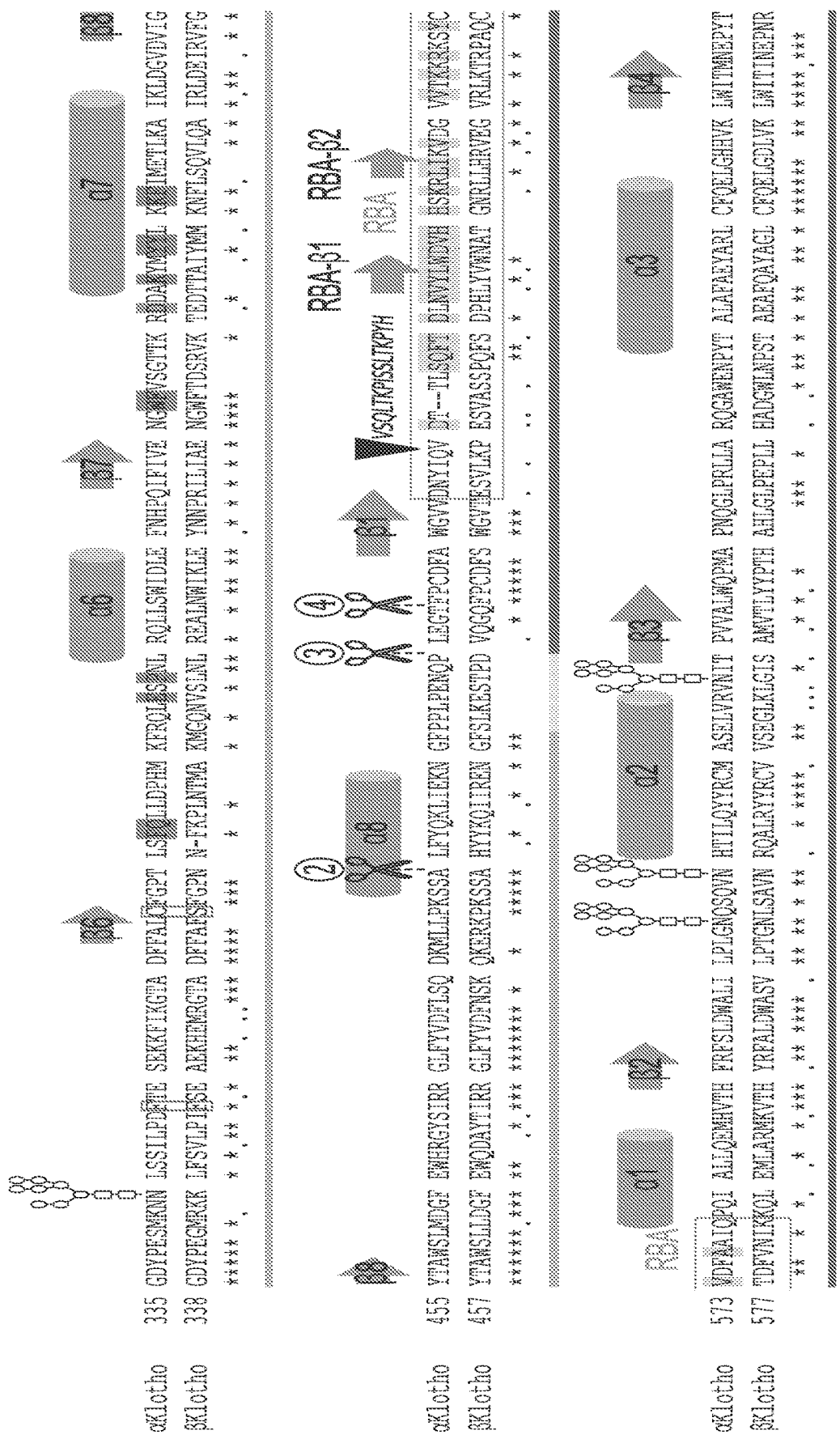
Figures 15B, 15C:
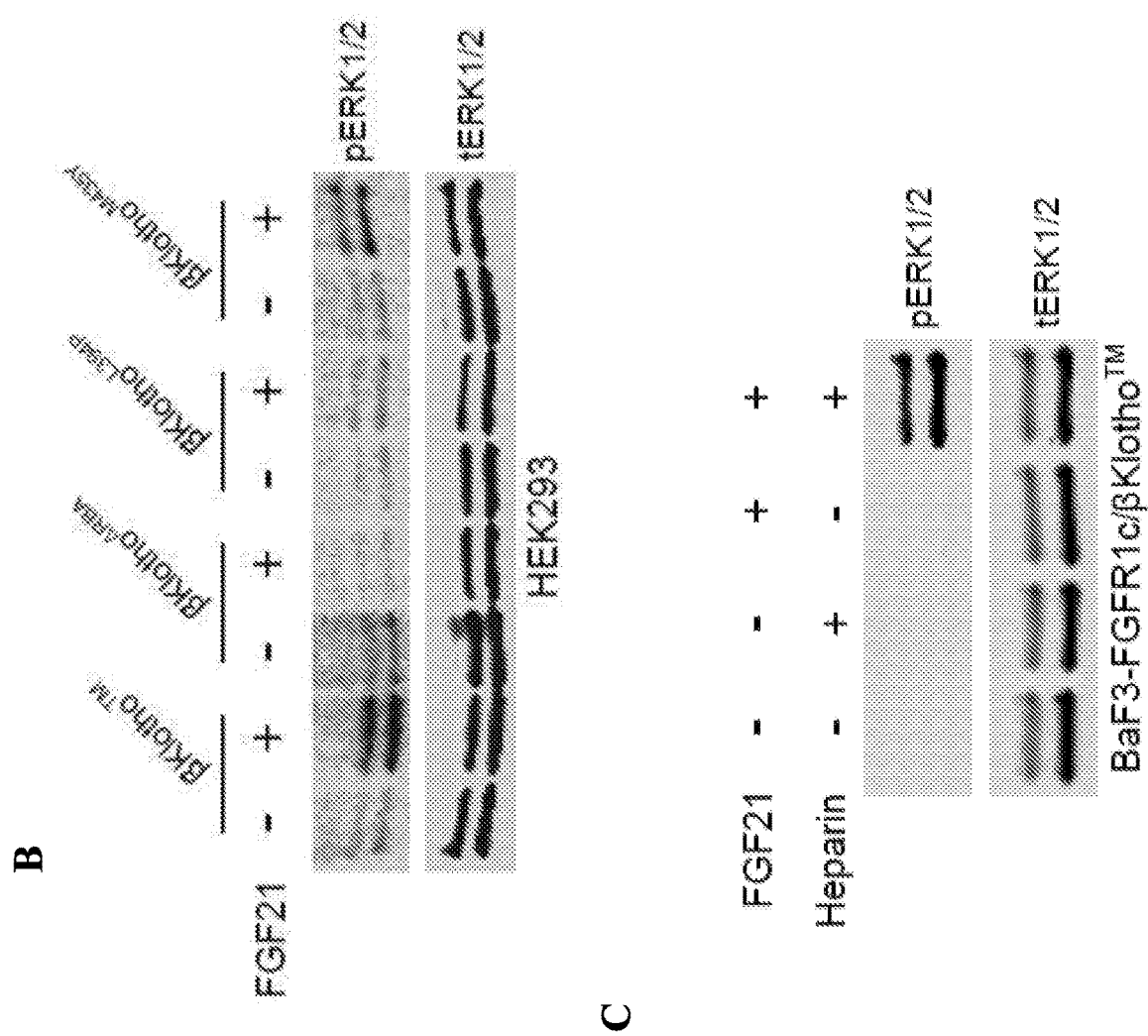

As discussed herein, the ectodomain of wildtype soluble α-Klotho protein includes a KL2 domain, which is identified within SEQ ID NO:1 above (shaded) and corresponds to L515 to P956 of SEQ ID NO:1 (see also FIGS. 10A and 14).

In certain embodiments, modified soluble α-Klotho proteins of the present invention include a KL2 extracellular domain having a modification(s) to substantially decrease or eliminate binding affinity for fibroblast growth factor receptor (FGFR)1c, FGFR3c, and/or FGFR4, as compared to a wildtype soluble α-Klotho protein.

The term binding affinity ($K_D$) as used herein, is intended to refer to the dissociation rate of a particular binding partner (e.g., antigen-antibody, protein-protein, or protein-receptor) interaction. The $K_D$ is the ratio of the rate of dissociation, also called the off-rate ($k_{off}$, to the association rate, or "on-rate ($k_{on}$)." Thus, $K_D$ equals $k_{off}/k_{on}$ and is expressed as a molar concentration (M). It follows that the smaller the $K_D$, the stronger the affinity of binding. Therefore, a $K_D$ of 1 μM indicates weaker binding affinity compared to a $K_D$ of 1 nM. $K_D$ values can be determined using methods well established in the art. One method for determining the $K_D$ is by using surface plasmon resonance (SPR), typically using a biosensor system such as a BIAcore® system.

Although certain modified soluble α-Klotho proteins of the present invention possess substantially reduced or eliminated binding affinity for FGFR1c, the modified soluble α-Klotho proteins maintain the ability to bind FGF23. In certain embodiments, the FGF23 is human FGF23 having the amino acid sequence of SEQ ID NO: 4 (GenBank accession no. AAG09917, which is hereby incorporated by reference in its entirety), as follows:

(GenBank Accession No. NP_075598, which is hereby incorporated by reference in its entirety). In another embodiment, the FGF receptor is FGFR3c receptor. In one particular embodiment, the FGFR3c receptor is the human FGFR3c receptor (GenBank Accession No. NP_000133, which is hereby incorporated by reference in its entirety). In another embodiment, the FGF receptor is FGFR4 receptor. In one particular embodiment, the FGFR4 receptor is the human FGFR4 receptor (GenBank Accession No. NP_002002, which is hereby incorporated by reference in its entirety).

The modified soluble α-Klotho proteins of the present invention include a KL2 extracellular domain having modification(s) to substantially decrease or eliminate binding affinity for FGFR1c, FGFR3c, and/or FGFR4, as compared to a wildtype soluble α-Klotho protein. In certain embodiments, the modification(s) include one or more additions, substitutions, and/or deletions. As discussed herein, the portion of wildtype α-Klotho protein that participates in binding FGFR1c was identified as the bold and underlined portion of SEQ ID NO:1 above (N530 to I578 of SEQ ID NO:1, also shown separately in SEQ ID NO:3) and referred to herein as the α-Klotho receptor binding arm (RBA): Receptor Binding Arm (RBA) found within the extracellular KL2 domain of wildtype soluble alpha-klotho:

(SEQ ID NO: 3)
NYIQVDTTLSQFTDLNVYLWDVHHSKRLIKVDGVVTKKRKSYCVDFAAI

In certain embodiments, one or more residues corresponding to those of wildtype soluble α-Klotho protein that make

```
  1 MLGARLRLWV CALCSVCSMS VLRAYPNASP LLGSSWGGLI HLYTATARNS YHLQIHKNGH

61 VDGAPHQTIY SALMIRSEDA GFVVITGVMS RRYLCMDFRG NIFGSHYFDP ENCRFQHQTL

121 ENGYDVYHSP QYHFLVSLGR AKRAFLPGMN PPPYSQFLSR RNEIPLIHFN TPIPRRHTRS

181 AEDDSERDPL NVLKPRARMT PAPASCSQEL PSAEDNSPMA SDPLGVVRGG RVNTHAGGTG

241 PEGCRPFAKF I
```

In certain embodiments, the binding affinity of modified soluble α-Klotho protein of the present invention to FGF23 is substantially the same as for wildtype soluble α-Klotho protein. In certain embodiments, the modified soluble α-Klotho protein of the present invention posses a binding affinity for FGF23 that is (or that is at least) 70%, 75%, 80%, 85%, 86%, 87%, 88%, 89%, 90%, 91%, 92%, 93%, 94%, 95%, 96%, 97%, 98%, 99%, or 99.9%, or 100% the binding affinity of wildtype soluble α-Klotho protein for FGF23.

In certain embodiments, the binding affinity of the modified soluble α-Klotho proteins of the present invention for FGFR1c, FGFR3c, and/or FGFR4 is decreased by (or by at least) 70%, 75%, 80%, 85%, 86%, 87%, 88%, 89%, 90%, 91%, 92%, 93%, 94%, 95%, 96%, 97%, 98%, 99%, 99.9%, or 100%, as compared to a wildtype soluble α-Klotho protein. Accordingly, in certain embodiments, binding affinity of the modified soluble α-Klotho proteins of the present invention for FGFR1c, FGFR3c, and/or FGFR4 is eliminated.

As described herein, the modified soluble α-Klotho proteins of the present invention have substantially decreased or eliminated binding affinity for FGFR1c, FGFR3c, and/or FGFR4. In one embodiment of the present invention, the FGF receptor is FGFR1c receptor. In one particular embodiment, the FGFR1c receptor is the human FGFR1c receptor contact with FGFR1c are deleted and/or substituted. The one or more residues deleted and/or substituted as described throughout the detailed description and figures may be contiguous or non-contiguous.

Accordingly, in certain embodiments, the modification(s) are of (or within) the RBA of the wildtype soluble α-Klotho protein (i.e., that corresponding to N530 to I578 of SEQ ID NO:1). As such, in certain embodiments, the modified soluble α-Klotho proteins of the present invention do not comprise the amino acid sequence of the RBA of wildtype soluble α-Klotho protein (e.g., N530 to I578 of SEQ ID NO:1, also shown separately in SEQ ID NO:3). In certain embodiments, the modification to substantially decrease or eliminate binding affinity for fibroblast growth factor receptor (FGFR)1c, FGFR3c, and/or FGFR4, as compared to a wildtype soluble α-Klotho protein, comprises a deletion and/or substitution of one or more of residues corresponding to N530 to I578 of SEQ ID NO:1. In certain embodiments, modified soluble α-Klotho proteins of the present invention include deletions and/or substitutions of (including of at least or up to) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 of the 49 amino acid residues of the RBA (i.e., that portion corresponding to N530 to I578 of SEQ ID NO:1).

Accordingly, in certain embodiments, the modified soluble α-Klotho protein does not comprise the amino acid sequence of SEQ ID NO:3. In certain embodiments, the modified soluble α-Klotho protein comprises the amino acid sequence of E34 to D529 of SEQ ID NO: 1 contiguously joined to the amino acid sequence of Q579 to S981 of SEQ ID NO: 1. In certain embodiments, D535-A576 of SEQ ID NO:1 are deleted and/or substituted. In one embodiment, one or more of amino acid residues corresponding to D535, S539, Q540, F541, T542, D543, N545, V546, Y547, L548, W549, D550, V551, H552, H553, K555, L557, I558, V564, K566, R568, Y571, V573, and A576 of SEQ ID NO:1 are deleted and/or substituted. In certain embodiments, modified soluble α-Klotho proteins of the present invention include deletions and/or substitutions of (including of at least, or up to) 1, 2, 3, 4, 5, 6, 7, 8, 9, 10, 11, 12, 13, 14, 15, 16, 17, 18, 19, 20, 21, 22, 23, or 24 of the 24 amino acid residues corresponding to one or more of D535, S539, Q540, F541, T542, D543, N545, V546, Y547, L548, W549, D550, V551, H552, H553, K555, L557, I558, V564, K566, R568, Y571, V573, and A576 of SEQ ID NO:1, or any other residue or combination of residues affecting binding to FGF receptor (e.g., FGFR1c). Exemplary substitutions which would impair or decrease binding affinity with FGFRs as described herein include one or more of Q540A, F541E, Y547E, L548E, W549E, L557E, R568E, and Y571A.

In certain embodiments, the modification to substantially decrease or eliminate binding affinity for fibroblast growth factor receptor (FGFR)1c, FGFR3c, and/or FGFR4, as compared to a wildtype soluble α-Klotho protein, comprises a deletion and/or substitution of one or more of residues corresponding to L544 to T565 of SEQ ID NO:1. In certain embodiments, modified soluble α-Klotho proteins of the present invention include deletions and/or substitutions of (including of at least or up to) 1, 2, 3, 4, 5, 6, 7, 8, 9, 10, 11, 12, 13, 14, 15, 16, 17, 18, 19, 20, 21, or 22 of the 22 amino acid residues corresponding to one or more of L544 to T565 of SEQ ID NO:1.

In certain embodiments, modified soluble α-Klotho proteins of the present invention include deletions and/or substitutions of residues within the KL2 domain that are outside the RBA (e.g., Cys621 in SEQ ID NO:1) that alter RBA confirmation and thereby affect binding to FGF receptor (e.g., FGFR1c).

In certain embodiments, the modified soluble α-Klotho protein of the present invention comprises the amino acid sequence of SEQ ID NO:2 or SEQ ID NO:7, shown below.

Exemplary modified soluble α-Klotho protein (signal peptide underlined, RBA bold underlined; mature protein E34 to S932; modified KL2 domain (LEGTF . . . GFPGP) italic shaded), with RBA deleted as indicated (corresponding to N530 to I578 of SEQ ID NO:1):

(SEQ ID NO: 2)
MPASAPPRRPRPPPPSLSLLLVLLGLGGRRLRAEPGDGAQTWARVSRPPAPEAAGLFQGTFPDGFLWAVGSAAYQ

TEGGWQQHGKGASIWDTFTHHPLAPPGDSRNASLPLGAPSPLQPATGDVASDSYNNVFRDTEALRELGVTHYRFS

ISWARVLPNGSAGVPNREGLRYYRRLLERLRELGVQPVVTLYHWDLPQRLQDAYGGWANRALADHFRDYAELCFR

HFGGQVKYWITIDNPYVVAWHGYATGRLAPGIRGSPRLGYLVAHNLLLAHAKVWHLYNTSFRPTQGGQVSIALSS

HWINPRRMTDHSIKECQKSLDFVLGWFAKPVFIDGDYPESMKNNLSSILPDFTESEKKFIKGTADFFALCFGPTL

SFQLLDPHMKFRQLESPNLRQLLSWIDLEFNHPQIFIVENGWFVSGTTKRDDAKYMYYLKKFIMETLKAIKLDGV

DVIGYTAWSLMDGFEWHRGYSIRRGLFYVDFLSQDKMLLPKSSALFYQKLIEKNGFPPLPENQP*LEGTFPCDFAW*

*GVVD[deleted RBA]QPQIALLQEMHVTHFRFSLDWALILPLGNQSQVNHTILQVYRCMASELVRVNITFVVA*

*LWQPMAPNQGLPRLLARQGAWENPYTALAFAEYARLCFQELGHHVKLWITMNEPYTRNNTYSAGHNLLKAHALAW*

*HVYNEKFRHAQNGKISIALQADWIEPACPFSQKDKEVAERVLEFDIGWLAEPIFGSGDYPWVMRDWLNQRNNFLL*

*PYFTEDEKKLIQGTFDFLALSHYTTILVDSEKEDPIKYNDYLEVQEMTDITWLNSPSQVAVVPWGLRKVLNWLKF*

*KYGDLPMYITENGIDDQLNAEDDQLRVYYMQNYINEALKAHTLDGINLCGYFAYSFNDRTAPREGLYRYAADQFE*

*PKASMKHYRKIIDSNGFPGPETLERFCPEEPTVCTECSFFHTRKS*

Exemplary modified soluble α-Klotho protein (α-Klotho$^{ecto/deltaRBA}$) (signal peptide underlined, RBA bold underlined; mature protein E34 to S959; modified KL2 domain (LEGTF . . . GFPGP) italic shaded), with a portion of the RBA deleted as indicated (corresponding to L544 to T565 of SEQ ID NO:1):

(SEQ ID NO: 7)
MPASAPPRRPRPPPPSLSLLLVLLGLGGRRLRAEPGDGAQTWARVSRPPAPEAAGLFQGTFPDGFLWAVGSAAYQ

TEGGWQQHGKGASIWDTFTHHPLAPPGDSRNASLPLGAPSPLQPATGDVASDSYNNVFRDTEALRELGVTHYRFS

ISWARVLPNGSAGVPNREGLRYYRRLLERLRELGVQPVVTLYHWDLPQRLQDAYGGWANRALADHFRDYAELCFR

-continued

```
HFGGQVKYWITIDNPYVVAWHGYATGRLAPGIRGSPRLGYLVAHNLLLAHAKVWHLYNTSFRPTQGGQVSIALSS

HWINPRRMTDHSIKECQKSLDFVLGWFAKPVFIDGDYPESMKNNLSSILPDFTESEKKFIKGTADFFALCFGPTL

SFQLLDPHMKFRQLESPNLRQLLSWIDLEFNHPQIFIVENGWFVSGTTKRDDAKYMYYLKKFIMETLKAIKLDGV

DVIGYTAWSLMDGFEWHRGYSIRRGLFYVDFLSQDKMLLPKSSALFYQKLIEKNGFPPLPENQPLEGTFPCDFAW

GVVDNYIQVDTTLSQFTD(deleted portion of RBAIKKRKSYCVDFAAIQPQIALLQEMHVTHPRFSLD

WALILFLGNQSQVNHTILQYIRCMASELVRVNITPVVALWQFMAPNQGLPRLLARQGAWENPYTALAFAFYARLC

FQELGHHVKLWITMNEPYTRNMTYSAGHNLLKAHALAWHVYNEKFRHAQNGKISIALQADWIEPACPFSQKDKEV

AERVLEFDIGWLAEPIFGSGDYPWVMRDWLNQRNNFLLPYFTEDEKKLIQGTFDFLALSHYTTILVDSEKEDPIK

YNDYLEVQEMTDITWLNSPSQVAVYFWGLRKVLNWLKFRYGDLPMYIISNGIDDGLHAEDDQLRVYYMQNYINEA

LKAHILDGINLCGYFAYSFNDRTAPRFGLYRYAADQFEPKASWWHIRKIIDSNGFPGPETLERFCPEEFTVCTEC

SFFHTRKS
```

In certain embodiments, the modified soluble α-Klotho protein of the present invention excludes the above-noted signal peptide and comprises the mature modified soluble α-Klotho protein sequence having an amino acid sequence from residue E34 to S932 of SEQ ID NO:2 or from E34 to S959 of SEQ ID NO: 7.

Also encompassed are modified soluble α-Klotho proteins having at least 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to the amino acid sequence of SEQ ID NO: 2 or the amino acid sequence from residue E34 to S932 of SEQ ID NO:2. Also encompassed are modified soluble α-Klotho proteins having at least 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to the amino acid sequence of SEQ ID NO: 7 or the amino acid sequence from residue E34 to S959 of SEQ ID NO:7.

Percent (%) amino acid sequence identity with respect to a given polypeptide sequence identified herein is defined as the percentage of amino acid residues in a candidate sequence that are identical to the amino acid residues in the reference sequence, after aligning the sequences and introducing gaps, if necessary, to achieve the maximum percent sequence identity, and not considering any conservative substitutions as part of the sequence identity. Percent (%) amino acid sequence homology with respect to a given polypeptide sequence identified herein is the percentage of amino acid residues in a candidate sequence that are identical to or strongly similar to the amino acid residues in the reference sequence, after aligning the sequences and introducing gaps, if necessary, to achieve the maximum percent sequence homology. Strongly similar amino acid residues may include, for example, conservative amino acid substitutions known in the art. Alignment for purposes of determining percent amino acid sequence identity and/or homology can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

In certain embodiments, the modified soluble α-Klotho proteins or fragments of wildtype soluble α-Klotho protein as described herein (proteins or polypeptides according to the present invention) may include additional portion(s) coupled to the C-terminal residue and/or the N-terminal residue of the amino acid sequences set forth herein. In some embodiments, the additional portion(s) may be a polypeptide sequence of 1, 2, 3, 4, 5, 6, 7, 8, 9, 10, or more amino acid residues. In certain embodiments, the additional portion(s) include signal peptides to, e.g., direct protein secretion. In other embodiments, the proteins and polypeptides according to the present invention do not include any additional portion(s) coupled to the C-terminal residue and/or the N-terminal residue of the chimeric protein of the present invention, respectively.

In certain embodiments, the proteins or polypeptides according to the present invention may include amino acid substitutions to, for example, (1) reduce susceptibility to proteolysis, (2) reduce susceptibility to oxidation, (3) alter binding affinity for forming protein complexes, or (4) confer or modify other physicochemical or functional properties. For example, single or multiple amino acid substitutions (preferably conservative amino acid substitutions) may be made in the normally-occurring sequence. A conservative amino acid substitution should not substantially change the structural characteristics of the parent sequence. Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al., *Nature* 354:105 (1991), which are each incorporated herein by reference.

Another aspect of the present invention relates to a modified soluble α-Klotho protein possessing a modification as compared to a wildtype soluble α-Klotho, where the wildtype soluble α-Klotho protein comprises the sequence of E34 to S981 of SEQ ID NO:1, and where the modified soluble α-Klotho protein comprises an amino acid sequence at least 80% identical to the amino acid sequence of SEQ ID NO:2 or the amino acid sequence of E34 to S932 of SEQ ID NO:2. In certain embodiments, the modified soluble α-Klotho protein has at least 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to the amino acid sequence of SEQ ID NO: 2 or the amino acid sequence from residue E34 to S932 of SEQ ID NO:2.

In one embodiment, the modified soluble α-Klotho protein comprises the amino acid sequence from residue E34 to S932 of SEQ ID NO:2.

Another aspect of the present invention relates to a modified soluble α-Klotho protein possessing a modification as compared to a wildtype soluble α-Klotho protein, where the wildtype soluble α-Klotho protein comprises the sequence of E34 to S981 of SEQ ID NO:1, and where the modified soluble α-Klotho protein comprises an amino acid sequence at least 80% identical to the amino acid sequence of SEQ ID NO:7 or the amino acid sequence of E34 to 5959 of SEQ ID NO:7. In certain embodiments, the modified soluble α-Klotho protein has at least 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to the amino acid sequence of SEQ ID NO: 7 or the amino acid sequence from residue E34 to S959 of SEQ ID NO:7. In one embodiment, the modified soluble α-Klotho protein comprises the amino acid sequence from residue E34 to S959 of SEQ ID NO:7.

Isolated Fragments of Soluble α-Klotho Protein

Yet another aspect of the present invention relates to an isolated fragment of wildtype soluble α-Klotho protein, where the isolated fragment comprises a fibroblast growth factor receptor (FGFR)1c binding domain and where the isolated fragment has substantially reduced or eliminated binding affinity for fibroblast growth factor (FGF)23, as compared to a wildtype soluble α-Klotho protein. Also encompassed are fragments (e.g., active fragments) of the isolated fragments of wildtype soluble α-Klotho protein described herein. An active fragment of an isolated fragment of wildtype soluble α-Klotho protein is one that has the ability to bind FGFR (e.g., FGFR1c, FGFR3c, and/or FGFR4). Reference isolated fragment(s) of wildtype soluble α-Klotho protein herein refers to the isolated fragment of wildtype soluble α-Klotho protein and fragments thereof.

Suitable wildtype soluble α-Klotho protein is described herein above. In one embodiment, the isolated fragment of wildtype soluble α-Klotho protein is an isolated fragment of the amino acid sequence of SEQ ID NO:1 or of E34 to S981 of SEQ ID NO: 1.

In certain embodiments, the binding affinity of the fragments of wildtype soluble α-Klotho proteins of the present invention for FGF23 is decreased by (or by at least) 70%, 75%, 80%, 85%, 86%, 87%, 88%, 89%, 90%, 91%, 92%, 93%, 94%, 95%, 96%, 97%, 98%, 99%, 99.9%, or 100%, as compared to a wildtype soluble α-Klotho protein. Accordingly, in certain embodiments, binding affinity of the fragments of wildtype soluble α-Klotho proteins of the present invention for FGF23 is eliminated.

The fragment of wildtype soluble α-Klotho protein of the present invention comprises a fibroblast growth factor receptor (FGFR)1c binding domain. As discussed above, the portion of wildtype α-Klotho protein that participates in binding FGFR1c was identified as the bold and underlined portion of SEQ ID NO:1 above (N530 to I578 of SEQ ID NO:1, also shown separately in SEQ ID NO:3) and referred to herein as the RBA: NYIQVDTTLSQFTDLN-VYLWDVHHSKRLIKVDGVVTKKRKSYCVDFAAI (SEQ ID NO:3). In certain embodiments, the fragment of wildtype soluble α-Klotho protein of the present invention comprises the amino acid sequence of SEQ ID NO: 3. Also encompassed are polypeptides having at least 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to the amino acid sequence of SEQ ID NO: 3. In certain embodiments, the fragments of wildtype soluble α-Klotho protein comprise modification(s) as compared to the corresponding sequence of the wildtype soluble α-Klotho protein. The modification may include one or more additions, substitutions, and/or deletions.

Accordingly, a further aspect of the present invention relates to an isolated fragment of wildtype soluble α-Klotho protein, where the isolated fragment comprises an amino acid sequence at least 80% identical to the amino acid sequence of SEQ ID NO:3. Accordingly, encompassed within the present invention are polypeptides at least 80% identical to the amino acid sequence of SEQ ID NO:3. In certain embodiments, the fragment of wildtype soluble α-Klotho protein (or polypeptide) has at least 81%, 82%, 83%, 84%, 85%, 86%, 87%, 88%, 89%, 90%, 91%, 92%, 93%, 94%, 95%, 96%, 97%, 98%, or 99% amino acid sequence identity to the amino acid sequence of SEQ ID NO: 3. In certain embodiments, the isolated fragment of wildtype soluble α-Klotho protein (or polypeptide) comprises the amino acid sequence of SEQ ID NO:3.

Modified soluble α-Klotho proteins according to the present invention and fragments of wildtype soluble α-Klotho protein according to the present invention (also collectively referred to herein as proteins and polypeptides of the present invention) may further include a heterologous sequence (e.g., protein or polypeptide). Such heterologous sequences may be joined to the, e.g., fragments of wildtype soluble α-Klotho proteins described herein to form a fusion protein or polypeptide, whereby one or more amino acid residues (such as a heterologous protein or peptide) are fused at the N-terminus or C-terminus of any proteins or protein fragments described herein. Thus, the term "fusion protein" refers to a protein or polypeptide that has an amino acid sequence derived from two or more proteins. The fusion protein may also include linking regions of amino acids between amino acid portions derived from separate proteins.

Suitable heterologous sequences are described in, for example, U.S. Patent Application Publication No. 2017/0226172 to Mohammadi et al., which is hereby incorporated by reference in its entirety. For example, heterologous peptides and polypeptides include, but are not limited to, an epitope (e.g., FLAG) or a tag sequence (e.g., $His_6$, and the like) to allow for the detection and/or isolation of the fragments of wildtype soluble α-Klotho protein; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region (e.g., an Fc domain); a half life-extending sequence comprising a combination of two or more (e.g., 2, 5, 10, 15, 20, 25, etc) naturally occurring or non-naturally occurring charged and/or uncharged amino acids (e.g., Serine, Glycine, Glutamic or Aspartic Acid) designed to form a predominantly hydrophilic or predominantly hydrophobic fusion partner for, e.g., a fragment of wildtype soluble α-Klotho protein; a functional or non-functional antibody, or a heavy or light chain thereof; and a polypeptide which has an activity, such as a therapeutic activity, different from the, e.g., fragments of wildtype soluble α-Klotho protein of the present invention.

Fusion proteins can be made by fusing heterologous sequences at either the N-terminus or at the C-terminus of, e.g., a fragment of wildtype soluble α-Klotho protein as described herein. A heterologous sequence can be an amino acid sequence or a non-amino acid-containing polymer.

Heterologous sequences can be fused either directly to the, e.g., fragments of wildtype soluble α-Klotho protein either chemically or by recombinant expression from a single polynucleotide or they may be joined via a linker or adapter molecule. A peptidyl linker or adapter molecule can be one or more amino acid residues (or -mers), e.g., 1, 2, 3, 4, 5, 6, 7, 8, or 9 residues (or -mers), preferably from 10 to 50 amino acid residues (or -mers), e.g., 10, 11, 12, 13, 14, 15, 16, 17, 18, 19, 20, 25, 30, 35, 40, 45, or 50 residues (or -mers), and more preferably from 15 to 35 amino acid residues (or -mers). A linker or adapter molecule can also be designed with a cleavage site for a DNA restriction endonuclease or for a protease to allow for the separation of the fused moieties. Suitable linkers are described in, for example, U.S. Patent Application Publication No. 2017/0226172 to Mohammadi et al., which is hereby incorporated by reference in its entirety.

In one embodiment, the heterologous sequence comprises a dimerization domain. The term dimerization domain as used herein refers to the protein domain which enables spontaneous dimerization of embodiments of the fusion proteins described herein. Dimerization domains enabling spontaneous dimerization include but are not limited to leucine zipper, zinc finger domain, or cysteine knot domains. Fc domains, as described herein also allow for dimerization/multimerization of the fusion proteins described herein.

In certain embodiments of the present invention, the proteins or polypeptides of the present invention (e.g., the fragment of wildtype soluble α-Klotho protein) is fused to an Fc domain, e.g., one or more domains of an Fc region of a human IgG. Antibodies comprise two functionally independent parts, a variable domain known as "Fab," that binds an antigen, and a constant domain known as "Fc," that is involved in, among other things, effector functions such as complement activation and attack by phagocytic cells. An Fc has a long serum half-life (Capon et al., "Designing CD4 Immunoadhesins for AIDS Therapy," *Nature* 337: 525-31 (1989), which is hereby incorporated by reference in its entirety) such that when joined together with a therapeutic protein, an Fc domain can provide longer half-life or incorporate such effector functions as Fc receptor binding, protein A binding, complement fixation, and other characteristics that are desirable in a therapeutic protein. In one example, a human IgG hinge, CH2, and CH3 region may be fused at either the amino-terminus or carboxyl-terminus of the proteins or polypeptides of the present application using methods known to the skilled artisan. The resulting fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, or reduced aggregation. Suitable Fc domains, including those modified to alter effector function, are described in, for example, U.S. Patent Application Publication No. 2017/0226172 to Mohammadi et al., which is hereby incorporated by reference in its entirety.

Proteins or polypeptides according to the present invention may be isolated proteins or polypeptides and may be prepared for use in accordance with the present invention using standard methods of synthesis known in the art, including solid phase peptide synthesis (Fmoc or Boc strategies) or solution phase peptide synthesis. Alternatively, proteins or polypeptides of the present invention may be prepared using recombinant expression systems.

Accordingly, another aspect of the present invention relates to isolated nucleic acid molecules encoding the modified soluble α-Klotho proteins or fragments of wildtype soluble α-Klotho protein described herein (collectively also referred to herein as proteins and polypeptides of the present invention). It will be understood that nucleic molecules encoding the proteins or polypeptides of the present invention can be determined based on reference to (or derived from), for example, the nucleotide sequence of wildtype human α-Klotho of SEQ ID NO:5: (GenBank Accession No. NM 004795, which is hereby incorporated by reference in its entirety), as follows.

SEQ ID NO: 5 (human αKlotho gene coding sequence), bolded portion encoding RBA (corresponding to N530 to I578 of SEQ ID NO:1) with underlined bolded portion encoding portion of RBA (corresponding to L544 to T565 of SEQ ID NO:1):

```
  9     AT GCCCGCCAGC GCCCCGCCGC GCCGCCCGCG GCCGCCGCCG CCGTCGCTGT

61 CGCTGCTGCT GGTGCTGCTG GGCCTGGGCG GCCGCCGCCT GCGTGCGGAG CCGGGCGACG

121 GCGCGCAGAC CTGGGCCCGT TTCTCGCGGC CTCCTGCCCC CGAGGCCGCG GGCCTCTTCC

181 AGGGCACCTT CCCCGACGGC TTCCTCTGGG CCGTGGGCAG CGCCGCCTAC CAGACCGAGG

241 GCGGCTGGCA GCAGCACGGC AAGGGTGCGT CCATCTGGGA TACGTTCACC CACCACCCCC

301 TGGCACCCCC GGGAGACTCC CGGAACGCCA GTCTGCCGTT GGGCGCCCCG TCGCCGCTGC

361 AGCCCGCCAC CGGGGACGTA GCCAGCGACA GCTACAACAA CGTCTTCCGC GACACGGAGG

421 CGCTGCGCGA GCTCGGGGTC ACTCACTACC GCTTCTCCAT CTCGTGGGCG CGAGTGCTCC

481 CCAATGGCAG CGCGGGCGTC CCCAACCGCG AGGGGCTGCG CTACTACCGG CGCCTGCTGG

541 AGCGGCTGCG GGAGCTGGGC GTGCAGCCCG TGGTCACCCT GTACCACTGG GACCTGCCCC

601 AGCGCCTGCA GGACGCCTAC GGCGGCTGGG CCAACCGCGC CCTGGCCGAC CACTTCAGGG

661 ATTACGCGGA GCTCTGCTTC CGCCACTTCG GCGGTCAGGT CAAGTACTGG ATCACCATCG

721 ACAACCCCTA CGTGGTGGCC TGGCACGGCT ACGCCACCGG GCGCCTGGCC CCCGGCATCC

781 GGGGCAGCCC GCGGCTCGGG TACCTGGTGG CGCACAACCT CCTCCTGGCT CATGCCAAAG
```

-continued

```
 841 TCTGGCATCT CTACAATACT TCTTTCCGTC CCACTCAGGG AGGTCAGGTG TCCATTGCCC

901 TAAGCTCTCA CTGGATCAAT CCTCGAAGAA TGACCGACCA CAGCATCAAA GAATGTCAAA

961 AATCTCTGGA CTTTGTACTA GGTTGGTTTG CCAAACCCGT ATTTATTGAT GGTGACTATC

1021 CCGAGAGCAT GAAGAATAAC CTTTCATCTA TTCTGCCTGA TTTTACTGAA TCTGAGAAAA

1081 AGTTCATCAA AGGAACTGCT GACTTTTTTG CTCTTTGCTT TGGACCCACC TTGAGTTTTC

1141 AACTTTTGGA CCCTCACATG AAGTTCCGCC AATTGGAATC TCCCAACCTG AGGCAACTGC

1201 TTTCCTGGAT TGACCTTGAA TTTAACCATC CTCAAATATT TATTGTGGAA AATGGCTGGT

1261 TTGTCTCAGG GACCACCAAG AGAGATGATG CCAAATATAT GTATTACCTC AAAAAGTTCA

1321 TCATGGAAAC CTTAAAAGCC ATCAAGCTGG ATGGGGTGGA TGTCATCGGG TATACCGCAT

1381 GGTCCCTCAT GGATGGTTTC GAGTGGCACA GAGGTTACAG CATCAGGCGT GGACTCTTCT

1441 ATGTTGACTT TCTAAGCCAG GACAAGATGT TGTTGCCAAA GTCTTCAGCC TTGTTCTACC

1501 AAAAGCTGAT AGAGAAAAAT GGCTTCCCTC CTTTACCTGA AAATCAGCCC CTAGAAGGGA

1561 CATTTCCCTG TGACTTTGCT TGGGGAGTTG TTGACAACTA CATTCAAGTA GATACCACTC

1621 TGTCTCAGTT TACCGACCTG AATGTTTACC TGTGGGATGT CCACCACAGT AAAAGGCTTA

1681 TTAAAGTGGA TGGGGTTGTG ACCAAGAAGA GGAAATCCTA CTGTGTTGAC TTTGCTGCCA

1741 TCCAGCCCCA GATCGCTTTA CTCCAGGAAA TGCACGTTAC ACATTTTCGC TTCTCCCTGG

1801 ACTGGGCCCT GATTCTCCCT CTGGGTAACC AGTCCCAGGT GAACCACACC ATCCTGCAGT

1861 ACTATCGCTG CATGGCCAGC GAGCTTGTCC GTGTCAACAT CACCCCAGTG GTGGCCCTGT

1921 GGCAGCCTAT GGCCCCGAAC CAAGGACTGC CGCGCCTCCT GGCCAGGCAG GGCGCCTGGG

1981 AGAACCCCTA CACTGCCCTG GCCTTTGCAG AGTATGCCCG ACTGTGCTTT CAAGAGCTCG

2041 GCCATCACGT CAAGCTTTGG ATAACGATGA ATGAGCCGTA CAAGGAAT ATGACATACA

2101 GTGCTGGCCA CAACCTTCTG AAGGCCCATG CCCTGGCTTG GCATGTGTAC AATGAAAAGT

2161 TTAGGCATGC TCAGAATGGG AAAATATCCA TAGCCTTGCA GGCTGATTGG ATAGAACCTG

2221 CCTGCCCTTT CTCCCAAAAG GACAAAGAGG TGGCTGAGAG AGTTTTGGAA TTTGACATTG

2281 GCTGGCTGGC TGAGCCCATT TTCGGCTCTG GAGATTATCC ATGGGTGATG AGGGACTGGC

2341 TGAACCAAAG AAACAATTTT CTTCTTCCTT ATTTCACTGA AGATGAAAAA AAGCTAATCC

2401 AGGGTACCTT TGACTTTTTG GCTTTAAGCC ATTATACCAC CATCCTTGTA GACTCAGAAA

2461 AAGAAGATCC AATAAAATAC AATGATTACC TAGAAGTGCA AGAAATGACC GACATCACGT

2521 GGCTCAACTC CCCCAGTCAG GTGGCGGTAG TGCCCTGGGG GTTGCGCAAA GTGCTGAACT

2581 GGCTGAAGTT CAAGTACGGA GACCTCCCCA TGTACATAAT ATCCAATGGA ATCGATGACG

2641 GGCTGCATGC TGAGGACGAC CAGCTGAGGG TGTATTATAT GCAGAATTAC ATAAACGAAG

2701 CTCTCAAAGC CCACATACTG GATGGTATCA ATCTTTGCGG ATACTTTGCT TATTCGTTTA

2761 ACGACCGCAC AGCTCCGAGG TTTGGCCTCT ATCGTTATGC TGCAGATCAG TTTGAGCCCA

2821 AGGCATCCAT GAAACATTAC AGGAAAATTA TTGACAGCAA TGGTTTCCCG GGCCCAGAAA

2881 CTCTGGAAAG ATTTTGTCCA GAAGAATTCA CCGTGTGTAC TGAGTGCAGT TTTTTTCACA

2941 CCCGAAAGTC TTTACTGGCT TTCATAGCTT TTCTATTTTT TGCTTCTATT ATTTCTCTCT

3001 CCCTTATATT TTACTACTCG AAGAAAGGCA GAAGAAGTTA CAAATAG
```

In one embodiment, the nucleic acid molecule comprises the nucleotide sequence shown in Table 1, including, e.g., the nucleotide sequence of SEQ ID NO: 6 (nucleic acid molecule encoding α-Klotho$^{ecto/deltaRBA}$ of SEQ ID NO: 7) or SEQ ID NO: 28 (nucleic acid molecule encoding RBA of SEQ ID NO: 3):

TABLE 1

| Description | Nucleotide Sequence |
| --- | --- |
| Nucleic acid molecule encoding α-Klotho$^{ecto/deltaRBA}$ of SEQ ID NO: 7 | ATGCCCGCCAGCGCCCCGCCGCGCCGCCCGC GGCCGCCGCCGCCGTCGCTGTCGCTGCTGCT GGTGCTGCTGGGCCTGGGCGGCCGCCGCCTG CGTGCGGAGCCGGGCGACGGCGCGCAGACCT GGGCCCGTTTCTCGCGGCCTCCTGCCCCCGA GGCCGCGGGCCTCTTCCAGGGCACCTTCCCC GACGGCTTCCTCTGGGCCGTGGGCAGCGCCG CCTACCAGACCGAGGGCGGCTGGCAGCAGCA CGGCAAGGGTGCGTCCATCTGGGATACGTTC ACCCACCACCCCCTGGCACCCCCGGGAGACT CCCGGAACGCCAGTCTGCCGTTGGGCGCCCC GTCGCCGCTGCAGCCCGCCACCGGGGACGTA GCCAGCGACAGCTACAACAACGTCTTCCGCG ACACGGAGGCGCTGCGCGAGCTCGGGGTCAC TCACTACCGCTTCTCCATCTCGTGGCGCGA GTGCTCCCAATGGCAGCGCGGGCGTCCCA ACCGCGAGGGGCTGCGCTACTACCGGCGCCT GCTGGAGCGGCTGCGGGAGCTGGGCGTGCAG CCCGTGGTCACCCTGTACCACTGGGACCTGC CCCAGCGCCTGCAGGACGCCTACGGCGGCTG GGCCAACCGCGCCCTGGCCGACCACTTCAGG GATTACGCGGAGCTCTGCTTCCGCCACTTCG GCGGTCAGGTCAAGTACTGGATCACCATCGA CAACCCCTACGTGGTGGCCTGGCACGGCTAC GCCACCGGGCGCCTGGCCCCCGGCATCCGGG GCAGCCCGCGGCTCGGGTACCTGGTGGCGCA CAACCTCCTCCTGGCTCATGCCAAAGTCTGG CATCTCTACAATACTTCTTTCCGTCCCACTC AGGGAGGTCAGGTGTCCATTGCCCTAAGCTC TCACTGGATCAATCCTCGAAGAATGACCGAC CACAGCATCAAAGAATGTCAAAAATCTCTGG ACTTTGTACTAGGTTGGTTTGCCAAACCCGT ATTTATTGATGGTGACTATCCCGAGAGCATG AAGAATAACCTTTCATCTATTCTGCCTGATT TTACTGAATCTGAGAAAAAGTTCATCAAAGG AACTGCTGACTTTTTTGCTCTTTGCTTTGGA CCCCACCTTGAGTTTTCAACTTTTGGACCCTC ACATGAAGTTCCGCCAATTGGAATCTCCCAA CCTGAGGCAACTGCTTTCCTGGATTGACCTT GAATTTAACCATCCTCAAATATTTATTGTGG AAAATGGCTGGTTTGTCTCAGGGACCACCAA GAGAGATGATGCCAAATATATGTATTACCTC AAAAAGTTCATCATGGAAACCTTAAAAGCCA TCAAGCTGGATGGGTGGATGTCATCGGGTA TACCGCATGGTCCCTCATGGATGGTTTCGAG TGGCACAGAGGTTACAGCATCAGGCGTGGAC TCTTCTATGTTGACTTTCTAAGCCAGGACAA GATGTTGTTGCCAAAGTCTTCAGCCTTGTTC TACCAAAAGCTGATAGAGAAAATGGCTTCC CTCCTTTACCTGAAATCAGCCCCTAGAAGG GACATTTCCCTGTGACTTTGCTTGGGGAGTT GTTGACAACTACATTCAAGTAGATACCACTC TGTCTCAGTTTACCGACAAGAAGAGGAAATC CTACTGTGTTGACTTTGCTGCCATCCAGCCC CAGATCGCTTTACTCCAGGAAATGCACGTTA CACATTTTCGCTTCTCCCTGGACTGGGCCCT GATTCTCCCTCTGGGTAACCAGTCCCAGGTG AACCACACCATCCTGCAGTACTATCGCTGCA TGGCCAGCGAGCTTGTCCGTGTCAACATCAC CCCAGTGGTGGCCCTGTGGCAGCCTATGGCC CCGAACCAAGGACTGCCGCGCCTCCTGGCCA GGCAGGGCGCCTGGGAGAACCCCTACACTGC CCTGGCCTTTGCAGAGTATGCCCGACTGTGC TTTCAAGAGCTCGGCCATCACGTCAAGCTTT GGATAACGATGAATGAGCCGTATACAAGGAA TATGACATACAGTGCTGGCCACAACCTTCTG AAGGCCCATGCCCTGGCTTGGCATGTGTACA ATGAAAAGTTTAGGCATGCTCAGAATGGGAA AATATCCATAGCCTTGCAGGCTGATTGGATA GAACCTGCCTGCCCTTTCTCCCAAAAGGACA AAGAGGTGGCTGAGAGAGTTTTGGAATTTGA CATTGGCTGGCTGGCTGAGCCCATTTTCGGC TCTGGAGATTATCCATGGGTGATGAGGGACT GGCTGAACCAAAGAAACAATTTTCTTCTTCC TTATTTCACTGAAGATGAAAAAAAGCTAATC CAGGGTACCTTTGACTTTTTGGCTTTAAGCC ATTATACCACCATCCTTGTAGACTCAGAAAA AGAAGATCCAATAAAATACAATGATTACCTA GAAGTGCAAGAAATGACCGACATCACGTGGC TCAACTCCCCCAGTCAGGTGGCGGTAGTGCC CTGGGGGTTGCGCAAAGTGCTGAACTGGCTG AAGTTCAAGTACGGAGACCTCCCCATGTACA TAATATCCAATGGAATCGATGACGGGCTGCA TGCTGAGGACGACCAGCTGAGGGTGTATTAT ATGCAGAATTACATAAACGAAGCTCTCAAAG CCCACATACTGGATGGTATCAATCTTTGCGG ATACTTTGCTTATTCGTTTAACGACCGCACA GCTCCGAGGTTTGCCTCTATCGTTATGCTG CAGATCAGTTTGAGCCCAAGGCATCCATGAA ACATTACAGGAAATTATTGACAGCAATGGT TTCCCGGGCCCAGAAACTCTGGAAAGATTTT GTCCAGAAGAATTCACCGTGTGTACTGAGTG CAGTTTTTTTCACACCCGAAAGTCTTAG (SEQ ID NO: 6) Portion of RBA deleted: CTGAATGTTTACCTGTGGGATGTCCACCACA GTAAAAGGCTTATTAAAGTGGATGGGGTTGT GACC (SEQ ID NO: 29) |
| Nucleic acid molecule encoding RBA of SEQ ID NO: 3 (underlined portion encoding portion of RBA corresponding to L544 to T565) | AACTA CATTCAAGTA GATACCACTC TGT CTCAGTT TACCGAC<u>CTG AATGTTTACC T GTGGGATGTCCACCACAGT AAAAGGCTTA TTAAAGTGGA TGGGGTTGTG ACCAAGAAG A GGAAATCCTA CTGTGTTGAC</u> TTTGCTG CCA TC (SEQ ID NO: 28) |

Yet another aspect of the present invention is a vector comprising the nucleic acid molecules, as well as a host cell comprising the exogenous nucleic acid molecules or the modified soluble α-Klotho proteins or fragments of wildtype soluble α-Klotho protein described herein.

Accordingly, also encompassed are methods of producing proteins or polypeptides of the present invention comprising growing the host cell under conditions where the protein or polypeptide encoded by the nucleic acid is expressed and, optionally, isolating the protein or polypeptide thereby produced. Nucleic acid molecules according to the present invention can be expressed in a host cell, and the encoded polynucleotides isolated, according to techniques that are known in the art.

Generally, the use of recombinant expression systems involves inserting the nucleic acid molecule encoding the amino acid sequence of the desired protein or polypeptide into an expression system to which the molecule is heterologous (i.e., not normally present). One or more desired nucleic acid molecules encoding a protein or polypeptide of the invention may be inserted into the vector. When multiple nucleic acid molecules are inserted, the multiple nucleic acid molecules may encode the same or different proteins or polypeptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell. The term host cell as used herein is intended to mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

A variety of genetic signals and processing events that control many levels of gene expression (e.g., DNA transcription and messenger RNA (mRNA) translation) can be incorporated into the nucleic acid construct to maximize protein production. For the purposes of expressing a cloned nucleic acid sequence encoding a desired protein, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR, EF-1alpha.

There are other specific initiation signals required for efficient gene transcription and translation in prokaryotic cells that can be included in the nucleic acid construct to maximize protein or polypeptide production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination *In Vitro*," *Methods in Enzymology* 68:473-82 (1979), which is hereby incorporated by reference in its entirety.

A nucleic acid molecule encoding a protein or polypeptide of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in GREEN & SAMBROOK, MOLECULAR CLONING: A LABORATORY MANUAL (4th ed., Cold Spring Harbor Laboratory Press 2012); SHORT PROTOCOLS IN MOLECULAR BIOLOGY (5th ed., Ausubel et al. eds., Wiley 2002); and U.S. Pat. No. 4,237,224 to Cohen and Boyer, which are hereby incorporated by reference in their entirety.

Once the nucleic acid molecule encoding the protein or polypeptide has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (4th ed., Cold Spring Harbor Laboratory Press 2012), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purified proteins or polypeptides may be obtained by several methods readily known in the art, including ion exchange chromatography, hydrophobic interaction chromatography, affinity chromatography, gel filtration, and reverse phase chromatography. The protein is preferably produced in purified form (preferably at least about 80% or 85% pure, more preferably at least about 90% or 95% pure) by conventional techniques. Depending on whether the recombinant host cell is made to secrete the protein into growth medium (see U.S. Pat. No. 6,596,509 to Bauer et al., which is hereby incorporated by reference in its entirety), the protein can be isolated and purified by centrifugation (to separate cellular components from supernatant containing the secreted protein) followed by sequential ammonium sulfate precipitation of the supernatant. The fraction containing the protein is subjected to gel filtration in an appropriately sized dextran or polyacrylamide column to separate the protein of interest from other proteins. If necessary, the protein fraction may be further purified by HPLC.

Pharmaceutical Compositions

Yet a further aspect of the present invention relates to pharmaceutical compositions comprising the modified soluble α-Klotho proteins (or fragments thereof) and/or fragments of wildtype soluble α-Klotho protein (or fragments thereof) described herein and a pharmaceutically acceptable carrier. Modified soluble α-Klotho proteins (or fragments thereof) and/or fragments of wildtype soluble α-Klotho protein (or fragments thereof) described herein are also referred to herein as proteins or polypeptides of the present invention.

A pharmaceutically acceptable carrier includes any material which, when combined with an active ingredient (e.g., proteins or polypeptides of the present invention), allows the ingredient to retain biological activity and is non-reactive with the subject's immune system. Compositions comprising such carriers are formulated by well known conventional methods (see, for example, REMINGTON: THE SCIENCE AND PRACTICE OF PHARMACY (22d edition, Loyd V. Allen ed., 2012), which is hereby incorporated by reference in its entirety). Such carriers include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term pharmaceutically acceptable means it is, within the scope of sound medical judgment, suitable for use in contact with the cells of humans and lower animals without undue toxicity, irritation, allergic response, and the like, and is commensurate with a reasonable benefit/risk ratio.

As discussed above, proteins or polypeptides of the present invention may also be modified using one or more additional or alternative strategies for prolonging the in vivo half-life of the protein. One such strategy involves the generation of D-peptide chimeric proteins, which consist of unnatural amino acids that are not cleaved by endogenous proteases. Alternatively, the proteins or polypeptides of the present invention may be fused to a protein partner that confers a longer half-life to the protein upon in vivo administration. Suitable fusion partners include, without limitation, immunoglobulins (e.g., the Fc portion of an IgG), human serum albumin (HAS) (linked directly or by addition of the albumin binding domain of streptococcal protein G), fetuin, or a fragment of any of these. The proteins or polypeptides of the present invention may also be fused to a macromolecule other than protein that confers a longer half-life to the protein upon in vivo administration. Suitable macromolecules include, without limitation, polyethylene glycols (PEGs). Methods of conjugating proteins or peptides to polymers to enhance stability for therapeutic administration are described in U.S. Pat. No. 5,681,811 to Ekwuribe, which is hereby incorporated by reference in its entirety. Nucleic acid conjugates are described in U.S. Pat. No. 6,528,631 to Cook et al., U.S. Pat. No. 6,335,434 to Guzaev et al., U.S. Pat. No. 6,235,886 to Manoharan et al., U.S. Pat. No. 6,153,737 to Manoharan et al., U.S. Pat. No. 5,214,136 to Lin et al., or U.S. Pat. No. 5,138,045 to Cook et al., which are hereby incorporated by reference in their entirety.

The pharmaceutical composition according to the present invention can be formulated for administration orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The formulations may conveniently be presented in unit dosage form and may be prepared by any of the methods well known in the art of pharmacy.

In certain embodiments of the present invention, the pharmaceutical composition according to the present invention is administered with (or itself includes) another active agent.

The pharmaceutical composition according to the present invention can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The most suitable route may depend on the condition and disorder of the recipient. The formulations may conveniently be presented in unit dosage form and may be prepared by any of the methods well known in the art of pharmacy.

Dosages and desired drug concentrations of pharmaceutical compositions of the present invention may vary depending on the particular use envisioned. The determination of the appropriate dosage or route of administration is well within the skill of an ordinary physician. Those skilled in the art can readily optimize pharmaceutically effective dosages and administration regimens for therapeutic compositions including the proteins and polypeptides according to the present invention, as determined by good medical practice and the clinical condition of the individual patient.

Compositions comprising the proteins or polypeptides of the present invention can be provided by continuous infusion, or by doses at intervals of, e.g., one day, one week, 1-7 times per week, or one month. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µg/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 15 mg/kg, at least 20 mg/kg, at least 25 mg/kg, or at least 50 mg/kg (see, e.g., Yang, et al., 2003, *New Engl. J. Med.* 349:427-434; Herold, et al., 2002, *New Engl. J. Med.* 346:1692-1698; Liu, et al., 1999, *J. Neurol. Neurosurg. Psych.* 67:451-456; Portielji, et al., 2003, *Cancer. Immunol. Immunother.* 52: 133-144, which are hereby incorporated by reference in their entirety). The dose may be at least 15 at least 20 at least 25 at least 30 at least 35 at least at least 45 at least 50 at least 55 at least 60 at least 65 at least 70 at least 75 at least 80 at least 85 at least 90 at least 95 or at least 100 µg. The doses administered to a subject may number at least 1, 2, 3, 4, 5, 6, 7, 8, 9, 10, 11, or 12, or more.

For therapeutic proteins or polypeptides of the present invention, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the proteins or polypeptides of the present invention may be calculated using the patient's weight in kilograms (kg) multiplied by the dose to be administered in mg/kg. The dosage of the proteins or polypeptides of the present invention may be 150 µg/kg or less, 125 µg/kg or less, 100 µg/kg or less, 95 µg/kg or less, 90 µg/kg or less, 85µ/kg or less, 80µ/kg or less, 75µ/kg or less, 70µ/kg or less, 65µ/kg or less, 60µ/kg or less, 55µ/kg or less, 50 µ/kg or less, 45µ/kg or less, 40µ/kg or less, 35µ/kg or less, 30 µ/kg or less, 25µ/kg or less, 20µ/kg or less, 15µ/kg or less, 10µ/kg or less, 5µ/kg or less, 2.5µ/kg or less, 2µ/kg or less, 1.5µ/kg or less, 1µ/kg or less, 0.5µ/kg or less, or 0.1µ/kg or less of a patient's body weight.

Unit dose of the proteins or polypeptides of the present invention may be 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the proteins or polypeptides of the present invention may achieve a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml/ml, or at least 400 µg/ml/ml in a subject. Alternatively, the dosage of the proteins or polypeptides described herein may achieve a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in the subject.

The protein or polypeptide of the present invention or pharmaceutical composition thereof may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. For other patients, it will be necessary to prescribe not more than one or two doses per day. For example, doses of proteins or polypeptides of the present invention may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side effects (see, e.g., Maynard, et al., 1996, A Handbook of SOPs for Good Clinical Practice, Interpharm Press, Boca Raton, Fla.; Dent, 2001, Good Laboratory and Good Clinical Practice, Urch Publ, London, UK, which are hereby incorporated by reference in their entirety).

Where sustained-release administration of a protein or polypeptide of the present invention is desired in a formulation with release characteristics suitable for the treatment of any disease or disorder requiring administration of the protein or polypeptide of the present invention, microencapsulation is contemplated. Microencapsulation of recombinant proteins for sustained release has been successfully performed with human growth hormone (rhGH), interferon- (rhIFN-), interleukin-2, and MN rgp120. Johnson et al., "Preparation and Characterization of Poly(D,L-lactide-coglycolide) Microspheres for Controlled Release of Human Growth Hormone," *Nat. Med.* 2:795-799 (1996); Yasuda, "Sustained Release Formulation of Interferon," *Biomed. Ther.* 27:1221-1223 (1993); Hora et al., "Controlled Release of Interleukin-2 from Biodegradable Microspheres," *Nat. Biotechnol.* 8:755-758 (1990); Cleland, "Design and Production of Single Immunization Vaccines Using Polylactide Polyglycolide Microsphere Systems," in VACCINE DESIGN: THE SUBUNIT AND ADJUVANT APPROACH 439-462 (Powell and Newman, eds. 1995); WO 97/03692; WO 96/40072; WO 96/07399; and U.S. Pat. No. 5,654,010, which are hereby incorporated by reference in their entirety. The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: BIODEGRADABLE POLYMERS AS DRUG DELIVERY SYSTEMS 1-41 (M. Chasin and R. Langer eds. 1990), which is hereby incorporated by reference in its entirety.

In some embodiments, the protein and/or polypeptide of the present invention or a pharmaceutical composition thereof is administered in a therapeutically effective amount in combination with a therapeutically effective amount of a second (or further) agent.

The modified soluble α-Klotho protein(s) according to the present invention and fragment(s) of wildtype soluble α-Klotho protein(s) according to the present invention may be administered in any combination thereof. For example, one or more modified soluble α-Klotho protein(s) according to the present invention may be administered in combination with one or more isolated fragment(s) of wildtype soluble α-Klotho protein according to the present invention. Further, a first modified soluble α-Klotho protein according to the present invention may be administered in combination with one or more other modified soluble α-protein(s) according to the present invention different from the first. Likewise a first fragment of wildtype soluble α-Klotho protein according to the present invention may be administered in combination with one or more other fragments of wildtype soluble α-Klotho protein according to the present invention different from the first. Also encompassed is any combination of proteins and/or polypeptides of the present invention and a therapeutically effective amount of one or more further agents.

Other suitable second (or further agents) include, for example, FGF23c-terminal peptides and compositions described in U.S. Patent Application Publication Nos. 2011/0190207 and 2017/0226172 to Mohammadi et al., each of which is hereby incorporated by reference in its entirety. In certain embodiments, the fragment(s) of wildtype soluble α-Klotho protein according to the present invention are administered in combination with one or more second (or further) agents comprising FGF23 c-terminal peptides and compositions described in U.S. Patent Application Publication Nos. 2011/0190207 and 2017/0226172 to Mohammadi et al., each of which is hereby incorporated by reference in its entirety, where the one or more second (or further) agents does not include the modified soluble α-Klotho protein according to the present invention.

Other suitable second (or further) agents include, for example, therapeutics useful in the treatment of hypophosphatemic conditions, including, e.g., an FGFR inhibitor, phosphate, calcium, osteopontin (OPN), parathyroid hormone or its analogue (PTH), and/or vitamin D or vitamin D analogue.

Other suitable second (or further) agents include, for example, therapeutics useful in the treatment of chronic kidney disease (CKD) or complications thereof.

In one embodiment, the protein or polypeptide of the present invention or pharmaceutical composition thereof is administered in conjunction with the second agent, i.e., the respective periods of administration are part of a single administrative regimen. In one embodiment, the protein or polypeptide of the present invention or pharmaceutical composition thereof and the second agent are administered concurrently, i.e., the respective periods of administration overlap each other. In one embodiment, the protein or polypeptide of the present invention or pharmaceutical composition thereof and the second agent are administered non-concurrently, i.e., the respective periods of administration do not overlap each other. In one embodiment, the protein or polypeptide of the present invention or pharmaceutical composition thereof and the second agent are administered sequentially, i.e., the protein or polypeptide of the present invention or pharmaceutical composition thereof is administered prior to and/or after the administration of the second agent. In one embodiment, the protein or polypeptide of the present invention or pharmaceutical composition thereof and the second agent are administered simultaneously as separate compositions. In one embodiment, the protein or polypeptide of the present invention or pharmaceutical composition thereof and the second agent are administered simultaneously as part of the same composition. The active agents described herein may be administered at the same or differing dosages.

Methods of Treatment

Yet another aspect of the present invention is directed to a method of treating a disease or disorder mediated by interaction of FGF23 with an FGFR/α-Klotho complex. The method involves administering to a patient in need thereof the modified soluble α-Klotho protein and/or the isolated fragment of the wildtype soluble α-Klotho protein invention, as described herein.

A patient or subject, as used herein, shall refer to a mammal, including, but not limited to, a human or non-human mammal, such as a murine, bovine, equine, canine, ovine, or feline.

A disease refers to any condition or disorder that damages or interferes with the normal function of a cell, tissue, or organ.

Diseases or disorders mediated by interaction of FGF23 with an FGF receptor (FGFR)/α-klotho complex include renal phosphate wasting disorders.

Examples of diseases or disorders mediated by interaction of FGF23 with an FGF receptor (FGFR)/α-klotho complex that can be treated include, but are not limited to, autosomal dominant hypophosphatemic rickets (ADHR), X-linked hypophosphatemic rickets (XLH), tumor-induced osteomalacia (TIO), fibrous dysplasia (FD), and chronic kidney disease (CKD).

Accordingly, another aspect of the present invention relates to a method of treating a renal phosphate wasting disorder, the method comprising administering to a patient in need thereof the modified soluble α-Klotho protein and/or the isolated fragment of the wildtype soluble α-Klotho protein of the invention, as described herein.

Yet another aspect of the present invention relates to a method of treating autosomal dominant hypophosphatemic rickets (ADHR), X-linked hypophosphatemic rickets (XLH), tumor-induced osteomalacia (TIO), fibrous dysplasia (FD), or chronic kidney disease (CKD), the method comprising administering to a patient in need thereof the modified soluble α-Klotho protein and/or the isolated fragment of the wildtype soluble α-Klotho protein of the invention, as described herein.

Yet another aspect of the present invention is directed to a method of treating one or more complications of chronic kidney disease (CKD). The method involves administering to a patient in need thereof the modified soluble α-Klotho protein and/or the isolated fragment of the wildtype soluble α-Klotho protein of the invention, as described herein. Proteins and/or polypeptides of the invention, or pharmaceutical compositions thereof, as described herein, can be used to inhibit off-target signaling of FGF23 on the heart tissue in CKD and hence alleviate, e.g., left ventricular hypertrophy (LVH) the primary cause of morbidity/mortality in CKD. Accordingly, the proteins and polypeptides of the invention, or pharmaceutical compositions thereof, may also be used in methods of treating complications of CKD. Such complications include, but are not limited to cardiovascular diseases such as, for example, left ventricular hypertrophy (LVH) and/or vascular calcification. In certain embodiments, treatment of LVH can be measured by modulation of left ventricular (LV) ejection fraction. In certain embodiments, administering the modified soluble α-Klotho protein and/or the isolated fragment wildtype soluble α-Klotho protein of the invention, as described herein (or compositions thereof), according to the present invention results in no further decrease left ventricular (LV) ejection fraction (halting disease progression) or in an increase in LV ejection fraction, as compared to a baseline level prior to the administration.

The proteins and polypeptides of the present invention (or pharmaceutical compositions thereof), as described herein, may be used therapeutically in hypophosphatemic conditions where FGF23 is not the primary cause of hypophosphatemia, and is not down-regulated as a compensatory mechanism, because they enhance renal phosphate retention. Hypophosphatemic conditions which may be treated by the proteins of the present invention include, among others, refeeding syndrome, diabetic ketoacidosis, asthma exacerbations and chronic obstructive pulmonary disease, and recovery from organ (particularly, kidney) transplantation (Gaasbeek et al., "Hypophosphatemia: An Update on its Etiology and Treatment," *Am J Med* 118(10):1094-1101 (2005); Miller et al., "Hypophosphatemia in the Emergency Department Therapeutics," *Am J Emerg Med* 18(4):457-461 (2000); Marinella M A., "Refeeding Syndrome and Hypophosphatemia," *J Intensive Care Med* 20(3):155-159 (2005), each of which is hereby incorporated by reference in its entirety).

A disorder or condition mediated by the interaction between FGF23 and an FGF receptor (FGFR)/α-klotho complex can be treated by administering a protein and/or polypeptide of the present invention, or a pharmaceutical composition thereof, as described herein, to a patient in need thereof in the amount of a therapeutically effective dose. The administration can be performed as described herein, such as by IV injection, intraperitoneal injection, intramuscular injection, or orally in the form of a tablet or liquid formation. In most situations, a desired dosage can be determined by a clinician, as described herein, and can represent a therapeutically effective dose of the protein and/or polypeptide described herein. It will be apparent to those of skill in the art that a therapeutically effective dose will depend, inter alia, upon the administration schedule, the unit dose of agent administered, whether the composition is administered in combination with other therapeutic agents, and the health of the recipient. The term "therapeutically effective dose," as used herein, means that amount of protein and/or polypeptide of the present invention that elicits the biological or medicinal response in a tissue system, animal, or human being sought by a researcher, medical doctor, or other clinician, which includes alleviation of the symptoms of the disease or disorder being treated.

Yet another aspect of the present invention is directed to a method of inhibiting FGF23/FGFR/α-Klotho ternary complex formation in a patient having a disease or disorder mediated by interaction of FGF23 with an FGFR/α-Klotho complex. The method involves administering to the patient the modified soluble α-Klotho protein and/or the isolated fragment of wildtype soluble α-Klotho protein of the invention, as described herein.

Yet another aspect of the present invention is directed to a method of inhibiting FGF23/FGFR/α-Klotho ternary complex formation in a patient having one or more complications of chronic kidney disease (CKD). The method involves administering the patient the modified soluble α-Klotho protein and/or the isolated fragment wildtype soluble α-Klotho protein of the invention, as described herein.

Antibodies

Another aspect of the present invention relates to antibodies specific to the receptor binding arm (RBA) of wildtype soluble α-Klotho protein, as described herein. Accordingly, also encompassed are isolated antibodies capable of binding to the receptor binding arm (RBA), or binding portion thereof, of wildtype soluble α-Klotho protein. In one embodiment, the receptor binding arm comprises the amino acid sequence of N530 to I578 of SEQ ID NO: 1.

Antibody "specificity" refers to selective recognition of the antibody or binding portion thereof as described herein for a particular epitope of the RBA of wildtype soluble α-Klotho protein. The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. The epitope of the antibodies described herein may be "linear" or "conformational". In a linear epitope, all of the points of interaction between the protein and the antibody occur linearly along the primary amino acid sequence of the protein. In a conformational epitope, the points of interaction occur across amino acid residues on the protein that are separated from one another, i.e., noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, 6, 7, 8, 9, 10, 11, 12, 13, 14, 15, 16, 17, 18, 19, 20 or more amino acids in a unique spatial conformation. Antibodies that recognize the same epitope can be verified in a simple immunoassay showing the ability of one antibody to block the binding of another antibody to a target antigen.

In one embodiment, the antibodies described herein are single domain antibodies. The unique binding property or antigen binding specificity of a given antibody is determined by its complementarity determining regions (CDR) typically found in the light and heavy chain variable regions of an immunoglobulin. Single domain antibodies are antibodies whose CDRs are part of a single domain polypeptide. Examples include, but are not limited to, heavy chain variable domain antibodies (including three CDRs) and light chain variable domain antibodies (containing three CDRs). Single domain antibodies can be derived from heavy chains and light chains of conventional 4-chain antibodies, antibodies naturally devoid of light chains, engineered antibodies and single domain scaffolds other than those derived from antibodies. In one embodiment, the single domain antibody of the present invention is a heavy chain single domain antibody, i.e., a $V_HH$ or nanobody. In one embodiment, the heavy chain single domain antibodies described herein are derived from naturally occurring heavy chain antibodies devoid of light chains.

Single domain antibodies are about 10-times smaller than conventional heavy chain and light chain containing IgG molecules. They are single polypeptides that are very stable, as they are resistant to extreme pH and temperature conditions. Moreover, unlike conventional antibodies, single domain antibodies are resistant to the action of proteases. In vitro expression of $V_H$Hs produces high yield, properly folded functional $V_H$Hs. Given their small size, $V_H$Hs are capable of recognizing unique epitopes of an antigen that cannot be bound by traditional full sized antibodies. As such, the anti-wildtype soluble α-Klotho protein single domain antibodies described herein bind unique epitopes of the RBA and/or bind epitopes more efficiently than other anti-wildtype soluble α-Klotho protein antibodies.

The single domain antibodies as described herein can be derived from antibodies raised in Camelidae species, for example in camel, dromedary, llama, vicuña, alpaca and guanaco. Single domain antibodies produced by other species are also within the scope of the invention. For example, single domain antibodies as disclosed herein may be derived from antibodies produced in any species including, but not limited to mouse, human, camel, llama, goat, rabbit, bovine, and cartilaginous fish.

In another embodiment, the antibody as described herein is an antibody fragment. In one embodiment, an antibody fragment is a single-chain polypeptide comprising one CDR as described herein. In another embodiment, the antibody fragment is a single-chain polypeptide comprising two CDRs as described herein. In another embodiment, the antibody fragment is a single-chain polypeptide containing all three CDRs of the heavy chain variable regions as described herein. An antibody fragment as referred to herein may be devoid of one or more framework regions (FR1, FR2, FR3, or FR4) or any portion thereof of the heavy chain variable region.

In one embodiment, the antibody as described herein comprises a $V_H$ domain coupled to one or more heavy chain constant regions ($C_H$). Mammalian heavy chain immunoglobulins typically have three or four constant region domains. Accordingly, the heavy chain variable regions described herein may be coupled to one heavy chain constant region, two heavy chain constant regions, three heavy chain constant regions, or four heavy chain constant regions.

In one embodiment, the antibody as described herein comprises a $V_H$ domain coupled to an Fc region, i.e., the antibody is an Fc-fusion antibody. The Fc region can be composed of the second and third constant domain regions (as it is for IgG, IgA, and IgD antibody isotypes), or composed of the second, third, and fourth constant domain regions (as it is for IgM and IgE antibody isotypes). In one embodiment, the Fc domain is derived from a human immunoglobulin. In one embodiment, the Fc domain is derived from human IgG1 including the $C_H2$ and $C_H3$ regions.

The Fc-region or domain of the fusion polypeptides described herein may impart non-antigen binding functions to the polypeptide, termed "effector functions", such as complement binding, antibody-dependent cell cytotoxicity (ADCC), and other functions mediated through the binding of subregions of this dimeric structure with immune cell surface receptors, Fc-receptors. Certain natural and synthetic variants of the Fc-region polypeptide sequences with altered effector functions that are suitable for use in the fusion polypeptides described herein include the subclass variants; e.g., IgGi, IgG2i, IgG3i, IgG24; and mutant polypeptides as described in e.g. U.S. Pat. No. 5,624,821 to Winter, U.S. Pat. No. 6,528,624 to Idusogie, U.S. Pat. No. 7,183,387 to Presta, and U.S. Pat. No. 7,317,091 to Lazar et al., which are hereby incorporated by reference in their entirety.

In another embodiment, the antibody or fragment thereof comprises two or more variable domain regions couple together. For example, in one embodiment, the antibody as described herein comprises two, or three, or more heavy chain variable regions linked together in tandem. In another embodiment, the heavy chain variable region is fused together with a light chain variable region to form a single-chain variable domain antibody (scFv) or a single-chain variable domain with an Fc portion (i.e., a scFv-Fc, e.g., a minibody). In another embodiment, two or more single-chain antibodies are linked together either in tandem (i.e., tandem scFvs), or such that they dimerize to form diabodies or triabodies. In another embodiment, the antibody is a tetrabody single chain variable fragment. In another embodiment, the antibody is a "linear antibody" which is an antibody comprising a pair of tandem Fd segments ($V_H$—$C_H1$-$V_H$-$C_H1$) that form a pair of antigen binding regions (see Zapata et al. *Protein Eng.* 8(10):1057-1062 (1995), which is hereby incorporated by reference in its entirety).

In another embodiment, the antibody of the disclosure is a conventional immunoglobulin (Ig) molecule comprising four polypeptide chains, i.e., two heavy chains and two light chains linked by disulfide bonds. In accordance with this embodiment, the single-domain antibodies as described herein are coupled to constant domain regions and further coupled to Ig light chains to create a four chain conventional antibody.

Antibody and antibody fragments disclosed herein can be mono-valent, bi-valent, or tri-valent with regard to binding domains, and the binding domains may be mono-specific, bi-specific, or tri-specific in binding specificity by design.

In one embodiment, the antibody or fragment thereof is isolated. As used herein, the term "isolated" refers to an antibody which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., gel filtration, ion exchange or reverse phase HPLC). Method for assessing antibody purity are known in the art (see e.g., Flatman et al., *J. Chromatogr. B* 848:79-87 (2007), which is hereby incorporated by reference in its entirety).

In one embodiment, the antibody or binding fragment thereof described herein is a chimeric antibody. A chimeric antibody is an antibody where one portion of the amino acid sequence of each of the heavy chains is homologous to corresponding sequences in an antibody derived from a particular species or belonging to a particular class, while the remaining segment of each chain is homologous to corresponding sequences in another species or class. Typically, the variable region mimics the variable region of an antibody derived from one species of mammals, while the constant portions are homologous to sequences of antibodies derived from another. For example, the variable region can be any one of the heavy chain variable regions disclosed herein derived from a camelid antibody coupled to one or more constant regions derived from a human immunoglobulin. Methods of making chimeric antibodies are well known in the art, see e.g., U.S. Pat. No. 4,816,567; and Morrison et al., "Chimeric human antibody molecules: mouse antigen-binding domains with human constant region domains," *Proc. Natl. Acad. Sci. USA* 81:6851-6855 (1984), which are hereby incorporated by reference in their entirety).

In another embodiment, the antibody or binding fragment thereof is a CDR-grafted antibody. A "CDR-grafted antibody" is an antibody which comprises variable region sequences of one species, where one or more of the CDR regions are replaced with CDR regions of another species. For example, in one embodiment the CDR grafted antibody comprises human or humanized heavy chain variable regions, where one or more of the CDRs within these regions is replaced with one or more CDRs disclosed herein that are derived from camelid heavy chain antibodies.

In another embodiment, the antibody or binding fragment thereof is a humanized antibody. A humanized antibody is an antibody or a variant, derivative, analog or portion thereof which comprises a framework region having substantially the amino acid sequence of a human antibody and a complementary determining region having substantially the amino acid sequence of a non-human antibody. As used herein, the term "substantially" in the context of a CDR refers to a CDR having an amino acid sequence that is at least 65%, at least 70%, at least 75%, at least 80%, at least 85%, at least 90%, at least 95%, at least 98% or at least 99% identical to the amino acid sequence of a non-human antibody CDR. Likewise, the term "substantially" in the context of a FR refers to a FR having an amino acid sequence that is at least 65%, at least 70%, at least 75%, at least 80%, at least 85%, at least 90%, at least 95%, at least 98% or at least 99% identical to the amino acid sequence of a human FR. A humanized antibody in accordance with the present disclosure comprises, for example, substantially all of at least one variable domains (Fv) in which all or substantially all of the CDR regions correspond to those of a non-human immunoglobulin (i.e., the donor camelid antibody) and all or substantially all of the framework regions are those of a human or humanized immunoglobulin framework sequence (i.e., the acceptor antibody).

Methods of humanizing antibodies are well known in the art, see e.g., Almagro and Fransson, "Humanization of Antibodies," Frontiers in Bioscience 13:1619-1633 (2008), U.S. Pat. No. 6,054,297 to Carter et al., U.S. Pat. No. 8,343,489, and U.S. Patent Application Publication No. US20100261620 to Almagro et al., which are hereby incorporated by reference in their entirety. The human or humanized framework sequences can be chosen based on known structure, i.e., a fixed framework sequence, sequence homology to the framework sequences of the donor antibody (e.g., the antibody from which the CDRs are derived), i.e., a best-fit framework sequence, or a combination of both approaches. Regardless of the method chosen to select the human framework sequence, the sequences can be selected from mature framework sequences, germline gene sequences, or consensus framework sequences. Compatible human framework sequences are those that are similar in both length and sequence to the framework sequence of the donor antibody sequence (i.e., the antibody from which the CDRs are derived) to ensure proper folding of the antibody and binding domain formation.

In one embodiment, the humanized framework sequence of a humanized antibody of the disclosure comprises a consensus framework sequence. A consensus framework sequence is derived from a consensus immunoglobulin sequence, which is the sequence formed from the most frequently occurring amino acids (or nucleotides) in a family of related immunoglobulin sequences (see e.g., WINNAKER, "From Genes to Clones: Introduction to Gene Technology" (1987); Carter et al., *Proc. Natl. Acad. Sci. USA*, 89:4285 (1992); and Presta et al., *J. Immunol.*, 151:2623 (1993), which are hereby incorporated by reference in their entirety). In a family of immunoglobulins, each position in the consensus sequence is occupied by the amino acid residue occurring most frequently at that position in the family. If two amino acids occur equally frequently, either can be included in the consensus sequence.

In another embodiment, a humanized antibody or binding fragment thereof as disclosed herein comprises a fixed framework region. Human heavy chain FR sequences known in the art can be used as heavy chain "acceptor" framework sequences (or simply, "acceptor" sequences) to humanize a non-human antibody using techniques known in the art (see e.g., Sims et al., *J. Immunol.*, 151:2296 (1993); Chothia et al., *J. Mol. Biol.*, 196:901 (1987), which are hereby incorporated by reference in their entirety). In one embodiment, human heavy chain acceptor sequences are selected from the framework sequences listed in publically available databases such as V-base or in the international ImMunoGeneTics® (IMGT®) information system.

Humanized antibodies or binding fragments thereof as described herein may also comprise at least a portion of an immunoglobulin constant region (Fc), typically that of a human immunoglobulin. In one embodiment, the humanized antibody disclosed herein comprises the heavy chain variable domain. The humanized antibody may further comprise the CH1, hinge, CH2, CH3, and CH4 regions of a human heavy chain. In another embodiment, the humanized antibody comprises only a humanized heavy chain. Humanized antibodies and binding fragments thereof as described herein may be selected from any class of immunoglobulins, including IgM, IgG, IgD, IgA and IgE, and any isotype, including without limitation IgG1, IgG2, IgG3 and IgG4. The humanized antibody or binding fragment thereof may comprise sequences from more than one class or isotype, and particular constant domains may be selected to optimize desired effector functions using techniques well-known in the art.

The antibodies and binding fragments thereof described herein can be humanized antibodies (fully or partially humanized) as described supra. Alternatively, the antibodies and binding fragments thereof can be animal antibodies such as, but not limited to, a bird (for example, a duck or a goose), a shark, a whale, or a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.). In one embodiment, the antibodies and binding fragments thereof as described herein are derived from camelid antibodies.

Methods of antibody production, in particular, monoclonal antibody production, may be carried out using the methods described herein and those well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of an animal which has been previously immunized with the antigen of interest (e.g., the RBA polypeptides (e.g., those comprising the amino acid sequence of SEQ ID NO:3), as set forth herein, or a modified soluble α-Klotho protein that varies by at least one amino acid from a wildtype soluble α-Klotho protein and comprises the RBA of SEQ ID NO:3) either in vivo or in vitro.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur J Immunol* 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

In another embodiment, monoclonal antibodies can be isolated from antibody phage libraries generated using the techniques described herein or known in the art, see e.g., McCafferty et al., "Phage Antibodies: Filamentous Phage Displaying Antibody Variable Domains," *Nature* 348:552-554 (1990), which is hereby incorporated by reference in its entirety. Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety, describe the isolation of murine and human antibodies, respectively, using phage libraries. Subsequent publications describe the production of high affinity (nM range) human antibodies by chain shuffling (Marks et al., *BioTechnology* 10:779-783 (1992), which is hereby incorporated by reference in its entirety), as well as combinatorial infection and in vivo recombination as a strategy for constructing very large phage libraries (Waterhouse et al., *Nuc. Acids. Res.* 21:2265-2266 (1993), which is hereby incorporated by reference in its entirety). Thus, these techniques are viable alternatives to traditional monoclonal antibody hybridoma techniques for isolation of monoclonal antibodies.

Alternatively, monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, generate monoclonal antibodies.

The polynucleotide(s) encoding a monoclonal antibody can further be modified using recombinant DNA technology to generate alternative antibodies. For example, the heavy chain constant domains of a camelid monoclonal antibody can be substituted for those regions of a human antibody to generate a chimeric antibody. Alternatively, the heavy chain constant domains of a camelid monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

EXAMPLES

Materials and Methods for Examples 1-5

DNA Expression Constructs: cDNA fragments encoding full-length human αKlotho, βKlotho, and FGFR1c were amplified by polymerase chain reaction (PCR) and subcloned into the lentiviral transfer plasmids pEF1a-IRES-hygro (α/βKlotho) or pEF1α-IRES-Neo (FGFR1c) using a ligation-independent In-Fusion HD cloning kit (#639648, Clontech Laboratories Inc., USA). PCR primers for FGFR1c were designed using NEBaseChanger software version 1.2.6 (New England Biolabs Inc., USA) and primers for α/βKlotho were designed using the primer design tool for the In-Fusion® HD cloning kit (Clontech Laboratories Inc., USA). A cDNA fragment encoding the entire extracellular domain of human αKlotho (residues M1 to S981; αKlotho$^{ecto}$ SEQ ID NO: 1) was subcloned into the mammalian expression plasmid pEF1α/myc-His A. DNA fragments for the mature form (that is, without the signal sequence) of human FGF23 (residues Y25 to I251 of SEQ ID NO: 4), human FGF21 (residues H29 to 5209 of SEQ ID NO: 8, below), and the extracellular D2-D3 region of human FGFR1c (residues D142 to R365 of SEQ ID NO: 9; FGFR1c$^{ecto}$), which is both necessary and sufficient for FGF binding, were amplified by PCR and ligated into the cloning sites of the bacterial expression plasmids pET-30a and pET-28a, respectively.

TABLE 2

| Description | Amino Acid Sequence |
|---|---|
| Human FGF21 (GenBank Accession No. NP_061986, which is hereby incorporated by reference in its entirety) (SEQ ID NO: 8) | 1 MDSDETGFEH SGLWVSVLAG LLLGACQAHP IPDSSPLLQF GGQVRQRYLY TDDAQQTEAH<br>61 LEIREDGTVG GAADQSPESL LQLKALKPGV IQILGVKTSR FLCQRPDGAL YGSLHFDPEA<br>121 CSFRELLLED GYNVYQSEAH GLPLHLPGNK SPHRDPAPRG PARFLPLPGL PPALPEPPGI<br>181 LAPQPPDVGS SDPLSMVGPS QGRSPSYAS |
| Human FGFR1c (GenBank Accession No. NP_075598, which is hereby incorporated by reference in its entirety) (SEQ ID NO: 9) | 1 MWSWKCLLFW AVLVTATLCT ARPSPTLPEQ AQPWGAPVEV ESFLVHPGDL LQLRCRLRDD<br>61 VQSINWLRDG VQLAESNRTR ITGEEVEVQD SVPADSGLYA CVTSSPSGSD TTYFSVNVSD<br>121 ALPSSEDDDD DDDSSSEEKE TDNTKPNRMP VAPYWTSPEK MEKKLHAVPA AKTVKFKCPS<br>181 SGTPNPTLRW LKNGKEFKPD HRIGGYKVRY ATWSIIMDSV VPSDKGNYTC IVENEYGSIN<br>241 HTYQLDVVER SPHRPILQAG LPANKTVALG SNVEFMCKVY SDPQPHIQWL KHIEVNGSKI<br>301 GPDNLPYVQI LKTAGVNTTD KEMEVLHLRN VSFEDAGEYT CLAGNSIGLS HHSAWLTVLE<br>361 ALEERPAVMT SPLYLEIIIY CTGAFLISCM VGSVIVYKMK SGTKKSDFHS QMAVHKLAKS<br>421 IPLRRQVTVS ADSSASMNSG VLLVRPSRLS SSGTPMLAGV SEYELPEDPR WELPRDRLVL<br>481 GKPLGEGCFG QVVLAEAIGL DKDKPNRVTK VAVKMLKSDA TEKDLSDLIS EMEMMKMIGK<br>541 HKNIINLLGA CTQDGPLYVI VEYASKGNLR EYLQARRPPG LEYCYNPSHN PEEQLSSKDL<br>601 VSCAYQVARG MEYLASKKCI HRDLAARNVL VTEDNVMKIA DFGLARDIHH IDYYKKTTNG<br>661 RLPVKWMAPE ALFDRIYTHQ SDVWSFGVLL WEIFTLGGSP YPGVPVEELF KLLKEGHRMD<br>721 KPSNCTNELY MMMRDCWHAV PSQRPTFKQL VEDLDRIVAL TSNQEYLDLS MPLDQYSPSF<br>781 PDTRSSTCSS GEDSVFSHEP LPEEPCLPRH PAQLANGGLK RR |

Single/multiple site mutations, loop deletions and truncations were introduced into expression constructs encoding the wild-type proteins using a Q5 Site-Directed Mutagenesis Kit (#E0554S, New England Biolabs Inc., USA). The integrity of each expression construct was confirmed by restriction enzyme digestion and DNA sequencing. Information on the constructs is provided in the Tables 3 and 4.

TABLE 3

Recombinant Proteins

| Protein Name | Amino Acid Boundaries/ Mutations | Expression Vector | Description |
|---|---|---|---|
| Human αKlotho Extracellular Domain | | | |
| αKlotho$^{ecto}$ | M1 to S981 | pEF1α/myc-His A | Soluble αKlotho ectodomain |
| αKlotho$^{ecto/ΔRBA}$ | αKlotho$^{ecto}$ variant lacking β1α1 loop (L544 to T565) of KL2 | pEF1α/myc-His A | Soluble αKlotho ectodomain with RBA deleted from KL2 domain |

TABLE 3-continued

Recombinant Proteins

| Protein Name | Amino Acid Boundaries/ Mutations | Expression Vector | Description |
| --- | --- | --- | --- |
| Human FGF23, Protease-Resistant Minimal Protein with Full Biological Activity | | | |
| FGF23$^{WT}$ | Y25 to S205 containing R176Q/R179Q ADHR mutations at $^{176}$RHTR$^{179}$ proteolytic cleavage motif past the FGF23 β-trefoil core | pET-30a | Protease-resistant, minimal FGF23 with full biological activity |
| FGF23$^{\Delta HBS}$ | FGF23$^{WT}$ variant carrying R140A/R143A double mutation | pET-30a | HS-binding site mutant of minimal FGF23 protein |
| FGF23$^{\Delta SRBS}$ | FGF23$^{WT}$ variant carrying M149A/N150A/P151A triple mutation | pET-30a | Secondary receptor-binding site mutant of mutant FGF23 protein |
| FGFR23$^{D188A}$ | FGF23$^{WT}$ variant carrying D188A single mutation | pET-30a | αKlotho-binding site mutant of minimal FGF23 protein |
| FGFR23$^{V192D}$ | FGF23$^{WT}$ variant carrying V192D single mutation | pET-30a | αKlotho-binding site mutant of minimal FGF23 protein |
| FGFR23$^{K194E/R196E/R198E}$ | FGF23$^{WT}$ variant carrying K194E/R196E/R198E triple mutation | pET-30a | αKlotho-binding site mutant of minimal FGF23 protein |
| Human FGFR1c Ligand-Binding Domain | | | |
| FGFR1c$^{ecto}$ | D142 to R365 | pET-28a | FGFR1c ligand-binding domain consisting of D2, D3, and D2-D3 linker |
| FGFR1c$^{ecto/\Delta HBS}$ | FGFR1c$^{ecto}$ variant carrying K160Q/K163Q double mutation | pET-28a | HS-binding site mutant of FGFR1c ligand-binding domain |
| FGFR1c$^{ecto/\Delta HBS'}$ | FGFR1c$^{ecto}$ variant carrying K207Q/R209Q double mutation | pET-28a | HS-binding site mutant of FGFR1c ligand-binding domain |
| FGFR1c$^{ecto/\Delta SLBS}$ | FGFR1c$^{ecto}$ variant carrying I203E single mutation | pHLsec | Secondary ligand-binding site mutant of FGFR1c ligand-binding domain |
| FGFR1c$^{ecto/\Delta SLBS'}$ | FGFR1c$^{ecto}$ variant carrying V221D single mutation | pHLsec | Secondary ligand-binding site mutant of FGFR1c ligand-binding domain |
| FGFR1c$^{ecto/\Delta RRBS}$ | FGFR1c$^{ecto}$ variant carrying A171D single mutation | pHLsec | Receptor-receptor-binding site mutant of FGFR1c ligand-binding domain |
| Human FGF21 | | | |
| FGF21$^{WT}$ | H29 to S209 | pET-28a | Full-length human FGF21 |

TABLE 4

Mammalian Expression Constructs

| Construct Name | Amino Acid Boundaries/ Mutations | Expression Vector | Description |
| --- | --- | --- | --- |
| Membrane-Bound Human αKlotho | | | |
| αKlotho ™ | M1 to K1012 | pEF1α-IRES-Hygro | Full-length, membrane-bound αKlotho |
| αKlotho $^{TM\Delta RBA}$ | αKlotho ™ variant lacking β1α1 loop (L538 to V560) of KL2 | pEF1α-IRES-Hygro | Membrane-bound αKlotho with RBA deleted from KL2 domain |
| αKlotho $^{TM/W417A}$ | αKlotho ™ variant carrying W417A single mutation | pEF1α-IRES-Hygro | FGF23-binding site mutant of membrane-bound αKlotho |
| αKlotho $^{TM/K429A}$ | αKlotho ™ variant carrying K429A single mutation | pEF1α-IRES-Hygro | FGF23-binding site mutant of membrane-bound αKlotho |
| αKlotho $^{TM/Y433F}$ | αKlotho ™ variant carrying Y433F single mutation | pEF1α-IRES-Hygro | FGF23-binding site mutant of membrane-bound αKlotho |
| αKlotho $^{TM/D756A}$ | αKlotho ™ variant carrying D756A single mutation | pEF1α-IRES-Hygro | FGF23-binding site mutant of membrane-bound αKlotho |
| αKlotho $^{TM/I822A}$ | αKlotho ™ variant carrying I822A single mutation | pEF1α-IRES-Hygro | FGF23-binding site mutant of membrane-bound αKlotho |
| αKlotho $^{TM/I836A}$ | αKlotho ™ variant carrying I836A single mutation | pEF1α-IRES-Hygro | FGF23-binding site mutant of membrane-bound αKlotho |

TABLE 4-continued

Mammalian Expression Constructs

| Construct Name | Amino Acid Boundaries/ Mutations | Expression Vector | Description |
|---|---|---|---|
| Membrane-Bound Human FGFR1c | | | |
| FGFR1c ™ | M1 to R822 | pEF1α-IRES-Neo | Full-length, membrane bound FGFR1c |
| FGFR1c ™/ΔHBS | FGFR1c ™ variant carrying K160Q/K163Q double mutation | pEF1α-IRES-Neo | HS-binding site mutant of membrane-bound FGFR1c |
| FGFR1c ™/ΔHBS' | FGFR1c ™ variant carrying K207Q/R209Q double mutation | pEF1α-IRES-Neo | HS-binding site mutant of membrane-bound FGFR1c |
| FGFR1c ™/S346Y | FGFR1c ™ variant carrying S346Y single mutation | pEF1α-IRES-Neo | FGF23-binding site mutant of membrane-bound FGFR1c |
| Membrane-Bound Human βKlotho | | | |
| βKlotho ™ | M1 to S1044 | pEF1α-IRES-Hygro | Full-length, membrane-bound βKlotho |
| βKlotho ™/ΔKBA | βKlotho ™ variant lacking β1α1 loop (Q544 to R572) of KL2 | pEF1α-IRES-Hygro | Membrane-bound βKlotho with RBA deleted from KL2 domain |
| βKlotho ™L394P | βKlotho ™ variant carrying L394P single mutation | pEF1α-IRES-Hygro | FGF21-binding site mutant of membrane-bound βKlotho |
| βKlotho ™M435Y | βKlotho ™ variant carrying M435Y single mutation | pEF1α-IRES-Hygro | FGF21-binding site mutant of membrane-bound βKlotho |

Recombinant Protein Expression and Purification: N-acetylglucosaminyltransferase I (GnTI) deficient HEK293S cells (#CRL-3022, American Type Culture Collection (ATCC), USA) were transfected by calcium phosphate co-precipitation with the expression construct encoding αKlotho$^{ecto}$. G418-resistant colonies were selected for αKlotho$^{ecto}$ expression using 0.5 mg/ml G418 (#6483, KSE Scientific, USA). The clone with the highest expression level was propagated in DME/F12 medium (#5H30023.02, HyClone, GE Healthcare, USA) supplemented with 10% Fetal Bovine Serum (FBS) (#35-010-CV, CORNING, USA), 100 U/ml penicillin plus 100 μg/ml streptomycin (#15140-122, Gibco, USA), and 0.5 mg/ml G418. For protein production, 1×10$^6$ cells were seeded in 25 cm cell culture dishes in 20 ml DME/F12 medium containing 10% FBS and grown for 24 hours. Thereafter, the medium was replaced with 25 ml DME/F12 medium containing 1% FBS. Three days later, secreted αKlotho$^{ecto}$ from two liters of conditioned medium was captured on a 5 ml heparin affinity HiTrap column (GE Healthcare, USA) and eluted with a 100 ml linear NaCl gradient (0-1.0 M). Column fractions containing αKlotho$^{ecto}$ were pooled and diluted 10-fold with 25 mM Tris pH 8.0 buffer, and the diluted protein sample was loaded onto an anion exchange column (SOUCRE Q, GE Healthcare, USA) and eluted with a 280 ml linear NaCl gradient (0-0.4 M). As a final purification step, SOURCE Q fractions containing αKlotho$^{ecto}$ were concentrated and applied to a Superdex 200 column (GE Healthcare, USA). αKlotho$^{ecto}$ protein was eluted isocratically in 25 mM HEPES pH 7.5 buffer containing 500 mM NaCl and 100 mM (NH$_4$)$_2$SO$_4$. A mutant of αKlotho$^{ecto}$ lacking the receptor binding arm (αKlotho$^{ecto/ΔRBA}$) was expressed and purified similarly as the wild-type counterpart.

Human wild-type FGF23 and its mutants were expressed in E. coli BL21 DE3 cells. Inclusion bodies enriched in misfolded insoluble FGF23 protein were dissolved in 6 M guanidinium hydrochloride and FGF23 proteins were refolded by dialysis for 2 days at 4° C. against buffer A (25 mM HEPES pH 7.5, 150 mM NaCl, 7.5% Glycerol) followed by buffer B (25 mM HEPES pH 7.5, 100 mM NaCl, 5% Glycerol). Correctly folded FGF23 proteins were captured on a 5 ml heparin affinity HiTrap column (GE Healthcare, USA) and eluted with a 100 ml linear NaCl gradient (0-2.0 M). Final purification of FGF23 proteins was achieved by cation exchange chromatography (SOURCE S, GE Healthcare, USA) with a 280 ml linear NaCl gradient (0-0.4 M). Human FGFR1c$^{ecto}$ and its mutants were also expressed as inclusion bodies in E. coli BL21 DE3 and refolded in vitro by slow dialysis at 4° C. against the following buffers: buffer A (25 mM Tris pH 8.2, 150 mM NaCl, 7.5% glycerol), buffer B (25 mM Tris pH 8.2, 100 mM NaCl, 5% glycerol), and buffer C (25 mM Tris pH 8.2, 50 mM NaCl, 5% glycerol); dialysis against each buffer was for minimally 12 hours. Properly folded FGFR1c proteins were purified by heparin affinity chromatography followed by size-exclusion chromatography as described above. All column chromatography was performed at 4° C. on an AKTA pure 25 L system (GE Healthcare, USA).

Crystallization and X-ray Crystal Structure Determination: To minimize the flexibility and protease-sensitivity of the FGF23-FGFR1c$^{ecto}$-αKlotho$^{ecto}$ complex and hence enhance its propensity to crystallize, a protease-resistant, C-terminally truncated FGF23 protein that lacks C-terminal residues Cys-206 to Ile-251 and carries Arg-to-Gln mutations at positions 176 and 179 of the $^{176}$Arg-His-Thr-Arg$^{179}$ proteolytic cleavage motif was used. These mutations occur naturally in patients with autosomal dominant hypophosphatemic rickets (ADHR) (White et al., "Autosomal Dominant Hypophosphataemic Rickets is Associated with Mutations in FGF23," Nature Genetics 26(3):345-348 (2000), which is hereby incorporated by reference in its entirety). Deletion of the C-terminal residues Cys-206 to Ile-25 does not compromise the phosphaturic activity of FGF23 in mice or its signaling potential in αKlotho™-expressing cultured cells (Goetz et al., "Isolated C-Terminal Tail of FGF23 Alleviates Hypophosphatemia by Inhibiting FGF23-FGFR-Klotho Complex Formation," PNAS USA 107(1):407-412 (2010), which is hereby incorporated by reference in its entirety). Thus, the first 26 amino acids (Ser-180 to Ser-205) of the 72-amino-acid-long C-terminal tail of FGF23, defined as the region past the $^{176}$Arg-His-Thr-Arg$^{179}$ proteolytic cleavage site, comprise the minimal region of the FGF23 C-terminal tail for binding the FGFR1c$^{ecto}$-αKlotho$^{ecto}$ complex (Goetz et al., "Isolated C-Terminal Tail of FGF23 Alleviates Hypophosphatemia by Inhibiting FGF23-FGFR-Klotho Complex Formation," PNAS USA 107(1):407-412 (2010), which is hereby incorporated by reference in its entirety). To prepare the FGF23-FGFR1c$^{ecto}$-αKlotho$^{ecto}$ complex, its purified components were mixed at a molar ratio of 1.2:1.2:1 and spin-concentrated using an Amicon Ultra-15 concentrator (#UFC901024, Merck Millipore, Germany). The concentrated sample was applied to a Superdex 200 column (GE Healthcare, USA) and eluted isocratically in 25 mM HEPES pH 7.5 buffer containing 500 mM NaCl and 100 mM (NH$_4$)$_2$SO$_4$. Column peak fractions were analyzed by SDS-PAGE and peak fractions containing the ternary complex were concentrated to 7 mg/ml. Concentrated ternary complex was screened for crystallization by sitting drop vapor diffusion. A range of commercially available crystallization screen kits was used: Protein Complex Suite (#130715), Classics Suite (#130701), Classics II Suite (#130723), and Classics Lite Suite (#130702) from Qiagen, Germany; Crystal Screen (#HR2-110), Crystal Screen 2 (#HR2-112), Crystal Screen Lite (#HR2-128), PEG/Ion Screen (#HR2-126), and PEGRx1 (#HR2-082) from Hampton Research, USA; and PEG Grid Screening Kit (#36436) and Crystallization Cryo Kit (#75403) from Sigma-Aldrich, USA. Drops consisting of 100 nl reservoir solution and 100 nl protein complex solution were equilibrated against 100 µl well volume set up in 96-well plates (Fisher Scientific, USA) using a Mosquito crystallization robot (TTP Labtech, U.K.). Plates were stored at 18° C. and automatically imaged by Rock Imager 1000 (Formulatrix, USA). Image data were collected and managed using Rock Maker software version 3.1.4.0 (Formulatrix, USA). One crystal hit was obtained after 7 days of plate incubation at 18° C. and one crystallization condition from the Protein Complex Suite (#130715, Qiagen, Germany) was chosen for optimization using the Additive Screen (#HR2-428) from Hampton Research, USA. Crystals were confirmed as protein crystals by UV imaging using Rock Imager 1000 (Formulatrix, USA). Crystal growth in optimized conditions was scaled up in 24-well VDXm plates (Hampton Research, USA) where crystals were grown by hanging drop vapor diffusion. Larger crystals (80×76×35 µm) were obtained within 28 days by mixing 1 µl of protein complex and 1 µl of crystallization solution. Some of those crystals were dissolved in Lämmli sample buffer after thorough rinsing, and analyzed by SDS-PAGE and staining with Coomassie Blue to confirm the presence of all three proteins in the ternary complex.

Crystals of ternary complex were briefly soaked in cryoprotective solution consisting of mother liquor supplemented with 25% (w/v) glycerol. These were then mounted on CryoLoops (Hampton Research, USA) and flash-frozen in liquid nitrogen. Crystal screening for X-ray diffraction and diffraction data collection were performed at 100K on one of the NE-CAT beam lines at the Advanced Photon Source synchrotron of Argonne National Laboratory. X-ray images were recorded with an ADSC Quantum 315 CCD detector with 1° oscillations at 100K, a wavelength of 0.97918 Å, and a crystal-to-detector distance of 420 mm. Crystals of the ternary complex belong to the monoclinic space group C2, and contain one ternary complex molecule in the asymmetric unit. X-ray diffraction data sets were collected to 3.0 Å from native protein crystals, integrated, and scaled using XDS (Kabsch, W., "Xds," Acta. Crystallogr. D Biol. Crystallogr. 66 (Pt 2):125-132 (2010), which is hereby incorporated by reference in its entirety) and SCALA (Evans, P., "Scaling and Assessment of Data Quality," Acta. Crystallogr. D Biol. Crystallogr. 62 (Pt 1):72-82 (2006), which is hereby incorporated by reference in its entirety) from the CCP4 software suite (Winn et al., "Overview of the CCP4 Suite and Current Developments," Acta. Crystallogr. D Biol. Crystallogr. 67 (Pt 4):235-242 (2011), which is hereby incorporated by reference in its entirety).

A clear molecular replacement solution was found for both KL domains using the Phaser module of PHENIX (Adams et al., "PHENIX: A Comprehensive Python-Based System for Macromolecular Structure Solution," Acta. Crystallogr. D Biol. Crystallogr. 66 (Pt 2):213-221 (2010), which is hereby incorporated by reference in its entirety) and homology models of KL1 and KL2, which were built with Rosetta software available through the ROBETTA Protein Structure Prediction Server. However, the FGF23-FGFR1c component of the ternary complex could not be found even after fixing the coordinates of the partial solution found for the KL domains. Through careful inspection of the crystal lattice and the Fo-Fc difference and 2Fo-Fc composite maps generated using the partial model, an FGF23-FGFR1c D2 portion of the FGF23-FGFR1c complex was manually placed. This was created using the experimental crystal structures of SOS-bound FGF23 (Goetz et al., "Molecular Insights into the Klotho-Dependent, Endocrine Mode of Action of Fibroblast Growth Factor 19 Subfamily Members," Mol. Cell Biol. 27(9):3417-3428 (2007), which are is hereby incorporated by reference in its entirety) (PDB ID: 2P39) and the FGF2-bound FGFR1c ectodomain (Plotnikov et al., "Structural Basis for FGF Receptor Dimerization and Activation," Cell 98(5):641-650 (1999), which is hereby incorporated by reference in its entirety) (PDB ID: 1CVS). After a few rounds of refinements, FGFR1c D3 could also be placed manually. Iterative rounds of model building and refinement were carried out using Coot (Emsley et al., "Coot: Model-Building Tools for Molecular Graphics," Acta. Crystallogr. D Biol. Crystallogr. 60 (Pt 12 Pt 1):2126-2132 (2004), which is hereby incorporated by reference in its entirety) and the Phenix.Refine module of PHENIX (Adams et al., "PHENIX: A Comprehensive Python-Based System for Macromolecular Structure Solution," Acta. Crystallogr. D Biol. Crystallogr. 66 (Pt 2):213-221 (2010), which is hereby incorporated by reference in its entirety).

The structure has been refined to 3.0 Å resolution with working and free R-factors of 23.72 and 29.68%, respectively, and good Ramachandran plot statistics. X-ray diffraction data collection and structure refinement statistics are summarized in Table 5. The final model comprises residues Glu-34 to Ser-981 of human αKlotho, residues Met-149 to Glu-360 of human FGFR1c and residues Tyr-25 to Ser-205 of human FGF23. Due to lack of sufficient electron density, the β1α1 loop (residues Leu-98 to Gln-118) of KL1 and residues Glu-957 to Ser-981 C-terminal to KL2, which constitute the extracellular juxtamembrane region that connects KL2 to the transmembrane helix, could not be built. Ordering of the most N-terminal residues Tyr-25 to Pro-30 of FGF23 is due to favorable crystal lattice contacts.

TABLE 5

X-ray Data Collection, Structure Refinement Statistics*

| Protein | FGF23-FGFR1c$^{ecto}$-αKlotho$^{ecto}$ |
|---|---|
| Data Collection | |
| X-ray wavelength (Å) | 0.97918 |
| Space group | C2 |
| Unit Cell Dimensions | |
| a, b, c (Å) | 283.31, 72.60, 95.33 |
| α, β, γ (°) | 90.00, 91.98, 90.00 |
| Resolution (Å) | 50-3.00 (3.18-3.0) |
| No. measured reflections | 294862 |
| No. unique reflections | 39077 |
| Data redundancy | 7.5 (7.6) |
| Data completeness (%) | 99.7 (98.8) |
| $R_{meas}$ (%) | 20.7 (138.0) |
| Signal (<I/σI>) | 11.1 (1.7) |
| Refinement | |
| Resolution (Å) | 48.81-3.00 (3.08-3.00) |
| No. unique reflections | 38950 (2688) |
| No. reflections ($R_{free}$) | 1947 (133) |
| $R_{work}/R_{free}$ | 23.00 (44.46)/27.82 (51.89) |
| No. TLS group | 3 (one per polypeptide chain) |
| Number of atoms | |
| Protein | 10602 |
| Sugar (NAG) | 98 |
| Ion (Zn$^{2+}$) | 1 |
| Solvent | 1 |
| R.m.s. deviations | |
| Bond length (Å) | 0.002 |
| Bond angle (°) | 0.483 |
| Average B factors (Å$^2$) | |
| Protein | 114 |
| Sugar (NAG) | 180 |
| Ion (Zn$^{2+}$) | 116 |
| Solvent | 58 |
| Ramachandran Plot | |
| Favored (%) | 89.06 |
| Allowed (%) | 9.72 |
| Outliers (%) | 1.22 |
| Rotamer outliers (%) | 2.23 |
| No. Cβ Deviations | 0 |
| All-Atom Clashscore | 6.5 |
| PDB ID | 5W21 |

*Values in parenthesis are for the highest resolution shell.

Size Exclusion Chromatography-Multi-Angle Light Scattering (SEC MALS): The SEC-MALS instrument setup consisted of a Waters Breeze 2 HPLC system (Waters, USA), a miniDAWN-TREOS 18-angle static light scattering detector with built-in 658.0-nm wavelength laser (Wyatt Technology Corp., USA), and an Optilab rEX refractive index detector (Wyatt Technology Corp., USA). A Superdex 200 10/300 GL column (GE Healthcare, USA) was placed in-line between the HPLC pump (Waters 1525) and the HPLC UV (Waters 2998 Photodiode Array), laser light scattering, and refractive index detectors. Light scattering and refractive index detectors were calibrated following the manufacturer's guidelines. The refractive index increment (dn/dc) in which n is the refractive index and c is the concentration of the mixture of DDM and CHS in 20 mM Tris-HCl pH 8.0 buffer containing 300 mM NaCl, was determined offline using an Optilab T-rEX refractive index detector. Monomeric bovine serum albumin (#23210, Thermo Scientific, USA) was used as part of routine data quality control.

60 ml or more of 25 mM HEPES pH 7.5 buffer containing 150 mM NaCl were passed through the system at a flow rate of 0.5 mL/min to equilibrate the Superdex 200 10/300 GL column and establish stable baselines for light scattering and refractive index detectors. Purified αKlotho$^{ecto}$, FGER1c$^{ecto}$ (wild type or mutant), and FGF23 (wild type or mutant) proteins were mixed at a molar ratio of 1:1:1 and concentrated to 12.5 µM. 50 µl of protein samples with a molar equivalent of a heparin hexasaccharide (#H006, Iduron, Manchester, U.K.) were injected onto the gel filtration column, and the column eluent was continuously monitored for 280 nm absorbance, laser light scattering, and refractive index. In a separate set of experiments, 50 µl of 1:1:1 FGF23-FGFR1c$^{ecto}$-αKlotho$^{ecto}$ ternary complex at 12.5 µM concentration was mixed with heparin hexasaccharide at molar ratios of 1:0.25, 1:0.5, 1:1, or 1:2, and the mixtures were injected onto the gel filtration column. 50 µl of ternary complex without added heparin hexasaccharide were run as a control. In yet another set of experiments, αKlotho$^{ecto}$ (wild type or mutant) and FGER1c$^{ecto}$ were mixed at a molar ratio of 1:1, and 50 µl of concentrated protein mixtures were injected onto the gel filtration column. 50 µl of concentrated αKlotho$^{ecto}$ (wild type or mutant) alone were run as a control in these experiments. The analyses were performed at ambient temperature. Data were collected every second at a flow rate of 0.5 ml/min. Laser light scattering intensity and eluent refractive index (concentration) data were adjusted manually for the volume delay of UV absorbance at 280 nm, and were processed using ASTRA software (Wyatt Technology Corp., USA). A protein refractive index increment (dn/dc value) of 0.185 ml/g was used for molecular mass calculations.

Cell Line Culture and Stimulation and Analysis of Protein Phosphorylation: HEK293 cells were maintained in DMEM medium (#10-017-CV, CORNING, USA) supplemented with 10% FBS, 100 U/ml of Penicillin and 100 µg/ml Streptomycin. HEK293 cells naturally express multiple FGFR isoforms including FGFR1c, FGFR3c, and FGFR4 but lack αKlotho or βKlotho co-receptors. BaF3 cells, an IL3-dependent hematopoietic pro B cell line, were cultured in RPMI 1640 medium (#10-040-CV, CORNING, USA) supplemented with 10% FBS, 100 U/ml of penicillin, 100 µg/ml streptomycin and 5 ng/ml murine IL-3 (#GFM1, Cell Guidance Systems Ltd, U.K.). BaF3 cells do not express FGFRs, α/βKlotho co-receptors, or HS cofactors, and hence are naturally non-responsive to FGFs. However, via controlled ectopic expression of FGFRs and Klotho co-receptors and exogenous supplementation with soluble HS, these cells can be forced to respond to FGF stimulation. As such, the BaF3 cell line has served as a powerful tool for reconstituting FGF-FGFR cell surface signal transduction complexes in order to dissect the molecular mechanisms of paracrine and endocrine FGF signaling (Suzuki et al., "BetaKlotho is Required for Fibroblast Growth Factor (FGF) 21 Signaling Through FGF Receptor (FGFR) 1c and FGFR3c." *Mol. Endocrinol.* 22(4):1006-1014 (2008); Ornitz et al., "Heparin is Required for Cell-Free Binding of Basic Fibroblast Growth Factor to a Soluble Receptor and for Mitogenesis in Whole Cells," *Mol. Cell Biol.* 12(1):240-247 (1992); and Ornitz et al., "FGF Binding and FGF Receptor Activation by Synthetic Heparan-Derived Di- and Trisaccharides," *Science* 268(5209):432-436 (1995), each of which is hereby incorporated by reference in its entirety).

Stable or transient expression of full-length (transmembrane) human αKlotho, βKlotho, FGFR1c, and mutants of these proteins in HEK293 or BaF3 cells was achieved using lentiviral vectors. To generate lentiviral expression vectors, HEK293 cells were seeded at a density of about 8×10$^5$ in 10 cm cell culture dishes and co-transfected by calcium phosphate co-precipitation with 8 μg of lentiviral transfer plasmid encoding wild-type or mutant αKlotho, βKlotho, or FGFR1c, 1.6 μg of pMD2.G envelope plasmid, and 2.5 μg of psPAX2 packaging plasmid. Fresh medium was added to the cells for a 3-day period after transfection. Cell culture supernatant containing recombinant lentivirus particles was harvested and used to infect $2 \times 10^5$ HEK293 or BaF3 cells in the presence of polybrene (5 μg/ml; #134220, Santa Cruz Biotechnology, USA). Stable transfectants were selected using hygromycin (1 mg/ml, #ant-hg-1, InvivoGen, USA) or G418 (0.5 mg/ml, #6483, KSE Scientific, USA). For transient protein expression, $2 \times 10^5$ HEK293 cells were plated in 6-well cell culture dishes and on the following day, the cells were infected with recombinant lentivirus in the presence of polybrene (16 μg).

For cell stimulation studies, unmodified and stably transfected HEK293 cells were seeded in 6-well cell culture plates at a density of $4 \times 10^5$ cells per well and maintained for 24 hours in cell culture medium without FBS. In the case of transiently transfected HEK293 cells, medium containing lentivirus particles was removed from the cells after approximately 12 hours incubation, and the cells were also serum-starved for 24 hours. Stably transfected BaF3 cells were seeded in 10 cm cell culture dishes at a density of $6 \times 10^6$ cells and serum-starved for 6 hours. Unmodified HEK293 cells were stimulated for 10 minutes with wild-type or mutant FGF23 both in the presence and absence of wild-type or mutant $\alpha Klotho^{ecto}$. HEK293 cells stably or transiently expressing wild-type αKlotho™ or its mutants were stimulated with wild-type or mutant FGF23 alone. In one set of experiments, HEK293 cells expressing wild-type αKlotho™ were pretreated with $\alpha Klotho^{ecto}$ for 10 minutes prior to stimulation with wild-type FGF23. BaF3 cells expressing wild-type or mutant FGFR1c were stimulated with wild-type or mutant FGF23 in the presence or absence of $\alpha Klotho^{ecto}$ and heparin. BaF3 cells co-expressing wild-type αKlotho™ and wild-type or mutant FGFR1c were stimulated with wild-type or mutant FGF23 in the presence of heparin. BaF3 cells co-expressing wild-type FGFR1c and wild-type or mutant βKlotho™ were stimulated with wild-type FGF21 in the presence or absence of heparin.

After stimulation, cells were lysed, and lysate samples containing approximately 30 μg total cellular protein were electrophoresed on 12% sodium dodecyl sulfate-polyacrylamide gels and electrotransferred onto a nitrocellulose membrane. The membrane was blocked for 1 hour at ambient temperature in Tris-buffered saline pH 7.6 containing 0.05% Tween-20 and 5% BSA (#BP1600-100, Fisher BioReagents, USA). Rabbit monoclonal antibodies to phosphorylated ERK1/2 (#4370, Cell Signaling Technology, USA) and total (phosphorylated and unphosphorylated) ERK1/2 (#4695, Cell Signaling Technology, USA) were diluted 1:2,000 and 1:1,000, respectively, in blocking buffer. After overnight incubation at 4° C. with one of these diluted antibodies, the blot was washed with Tris-buffered saline pH 7.6 containing 0.05% Tween-20, and then incubated at ambient temperature for half an hour with 1:10,000 diluted IRDye secondary antibody (#926-32211 (goat anti-rabbit), LI-COR, USA). After another round of washing with Tris-buffered saline pH 7.6 containing 0.05% Tween-20, the blot was imaged on an Odyssey Fc Dual-mode Imaging System (LI-COR, USA).

αKlotho Treatment of Mice and Serum/Urinary Phosphate Analysis: Mice of the strain 129/Sv (Charles River Laboratories, USA) were housed in a room with 22±1° C. temperature and 12:12 hour light/dark cycle, and had ad libitum access to tap water and Teklad global 16% rodent diet (Envigo, USA). Twenty 6-week old mice of each gender were assigned to receive either recombinant $\alpha Klotho^{ecto}$ protein diluted in isotonic saline (0.1 mg/kg BW) or protein diluent only (buffer control). Mice were placed in metabolic cages for a one-day acclimation, and returned to the cages for 24-hour urine collection following IP injection of $\alpha Klotho^{ecto}$ protein or buffer control. After urine collection, mice were placed under isofluorane anesthesia, and blood was drawn from the retro-orbital sinus and transferred into tubes containing a few drops of sterile solution of heparin (Sagent Pharmaceuticals, USA). After centrifugation at 3,000 g at 4° C. for 5 minutes, supernatant plasma was taken out of the tubes and stored at −80° C. Blood and urine samples were also collected before injection of $\alpha Klotho^{ecto}$ or buffer control. Phosphate and creatinine concentrations in plasma and urine were measured using a Vitros Chemistry Analyzer (Ortho-Clinical Diagnosis, USA) and a P/ACE MDQ Capillary Electrophoresis System equipped with a photodiode detector (Beckman-Coulter, USA), respectively.

In a separate set of experiments, mice were given an IP injection of wild-type $\alpha Klotho^{ecto}$ (0.1 mg/kg BW), RBA deletion mutant, $\alpha Klotho^{ecto/\Delta RBA}$ (0.1 mg/kg BW), or protein diluent only (six mice per group), and blood and urine samples were collected for measurement of phosphate and creatinine as described above. In yet another set of experiments, mice were injected IP with 0.1 mg/kg BW of wild-type $\alpha Klotho^{ecto}$, mutant $\alpha Klotho^{ecto/\Delta RBA}$, or protein diluent only (three to four mice per group), and kidneys were harvested from the mice under isofluorane anesthesia four hours after the injection. Total RNA was extracted from the kidneys using RNAeasy kit (Qiagen, USA), and Egr1 mRNA levels were quantified by real time PCR with cyclophilin as control. Template cDNA for the PCR was generated using SuperScript III First Strand Synthesis System (Invitrogen, USA) and oligo-(dT) primers. PCR primers for Egr1 were 5'-GAGGAGATGATGCTGCTGAG-3' (SEQ ID NO: 10) and 5'-TGCTGCTGCTGCTATTACC-3' (SEQ ID NO: 11). PCR primers for cyclophilin were 5'-GTCTCTTTTCGCCGCTTGCT-3'(SEQ ID NO: 12) and 5'-TCTGCTGTCTTTGGAACTTTGTCTG-3' (SEQ ID NO: 13). Real time PCR was performed in triplicate for each kidney RNA sample. Except for Egr1 expression analysis, data were analyzed by paired Student's t test.

Enzymatic Assay: To examine $\alpha Klotho^{ecto}$ for glycoside-hydrolase activity, 4-Methylumbelliferyl-β-D-Xylopyranoside (#M7008, Sigma-Aldrich, USA), 4-Methylumbelliferyl-β-D-glucuronide (#474427, Sigma-Aldrich, USA) and 4-Methylumbelliferyl-α-D-N-acetylneuraminic acid (#69587, Sigma-Aldrich, USA) were selected as substrates and commercially available recombinant Neuraminidase (#10269611001, Roche Diagnostics GmbH, Germany) and β-Glucuronidase (#G0251, Sigma-Aldrich, USA) were used as positive controls. 20 μg of $\alpha Klotho^{ecto}$ or the control enzymes were added into reaction buffer [0.1 M sodium citrate buffer pH 5.6, 0.05 M NaCl, 0.01% Tween 20] containing 0.5 mM substrate at a final volume of 100 μl, and the reaction mixtures were incubated at 37° C. for 2 hours. Enzymatic activity was assessed by quantifying fluorescence intensity of released 4-methylumbelliferone at an excitation wavelength of 360 nm and an emission wavelength of 450 nm using a FlexStation 3 Multi-Mode Microplate Reader (Molecular Devices, USA).

Fluorescence Dye-Based Thermal Shift Assay: SYPRO Orange dye (#S6650, ThermoFisher Scientific, USA) was used as the fluorescent probe. 15 μl of 20 μM solutions of protein samples (wild-type and mutated forms of FGF23; $\alpha Klotho^{ecto}$ or $\alpha Klotho^{ecto/\Delta RBA}$ alone; 1:1 mixtures of $\alpha Klotho^{ecto}$ or $\alpha Klotho^{ecto/\Delta RBA}$ with FGF23 C-terminal tail peptide) were mixed with 5 µl of working dye solution (1:25 dilution) in duplicate in PCR strips. A temperature gradient from 4° C. to 100° C. at 1° C./minute increment was carried out with a CFX96 Touch™ Real-Time PCR Detection System (Bio-Rad, USA). Fluorescence was recorded as a function of temperature in real time. The melting temperature (Tm) was calculated with StepOne software v2.2 as the maximum of the derivative of the resulting SYPRO Orange fluorescence curves.

Figures 2A, 2B, 2C:
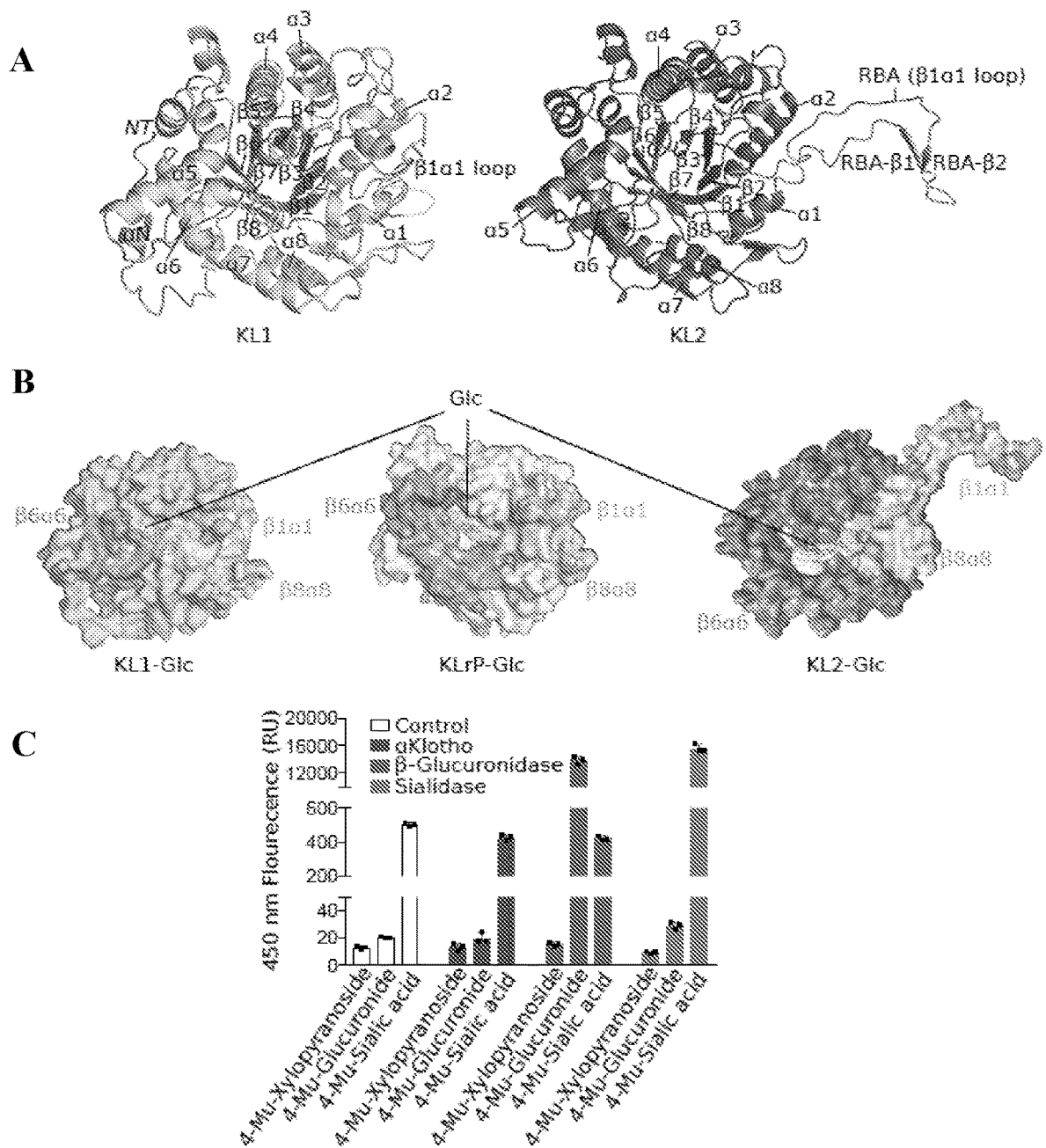
FIGS. 2A-2C show that αKlotho is a non-enzymatic molecular scaffold.
Figure 5A:
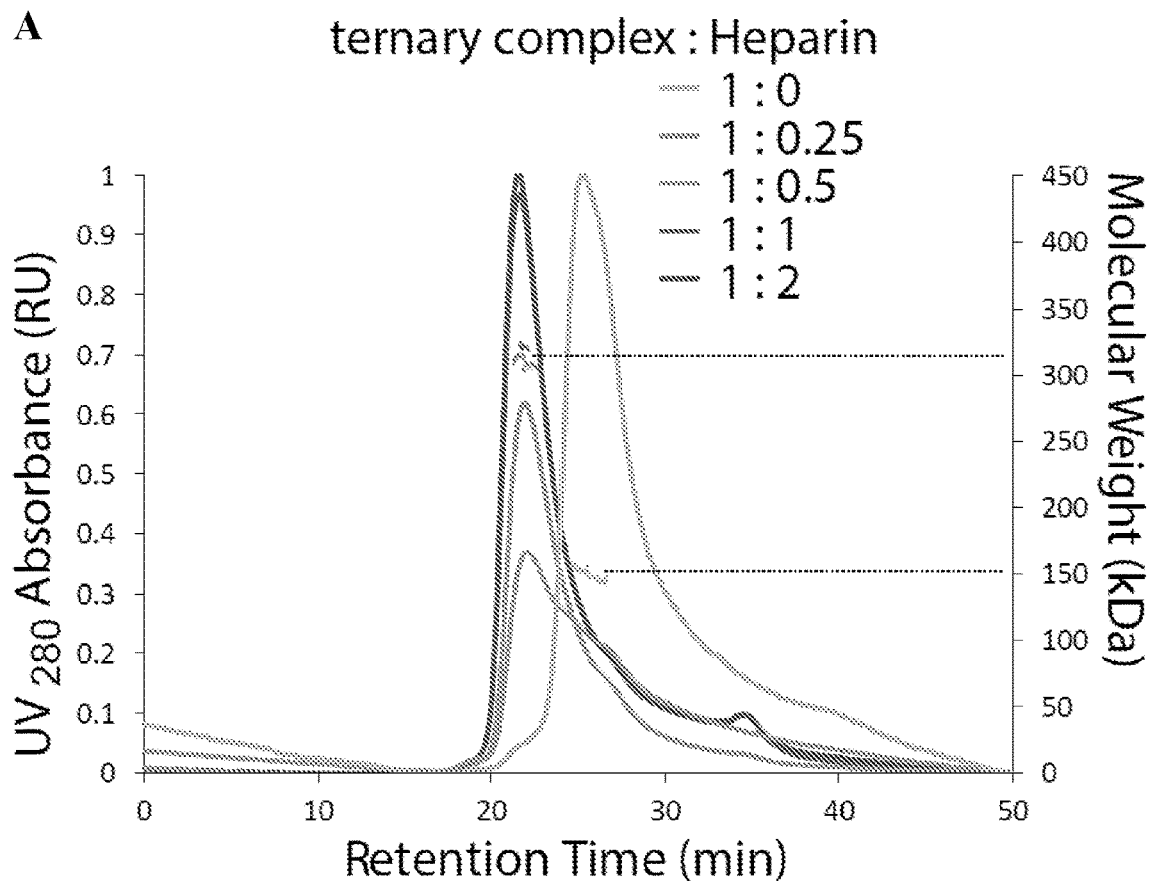
FIGS. 5A-5G show that HS dimerizes two 1:1:1 FGF23-FGFR1c-αKlotho complexes into a symmetric 2:2:2:2 FGF23-FGFR 1c-αKlotho-HS signal transduction unit.
Figure 5B:
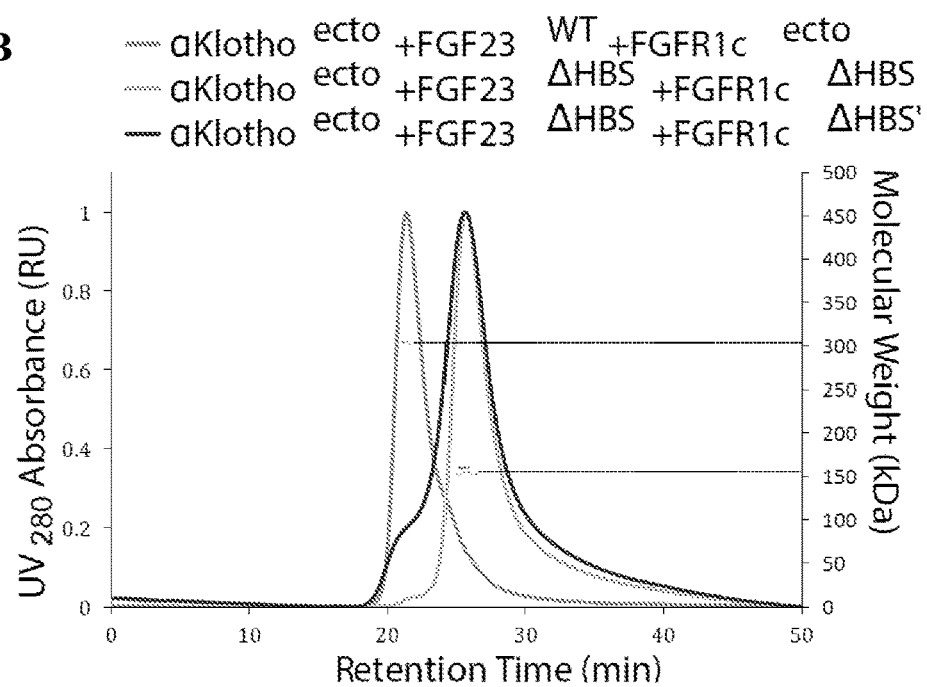
Figures 5C, 5D:
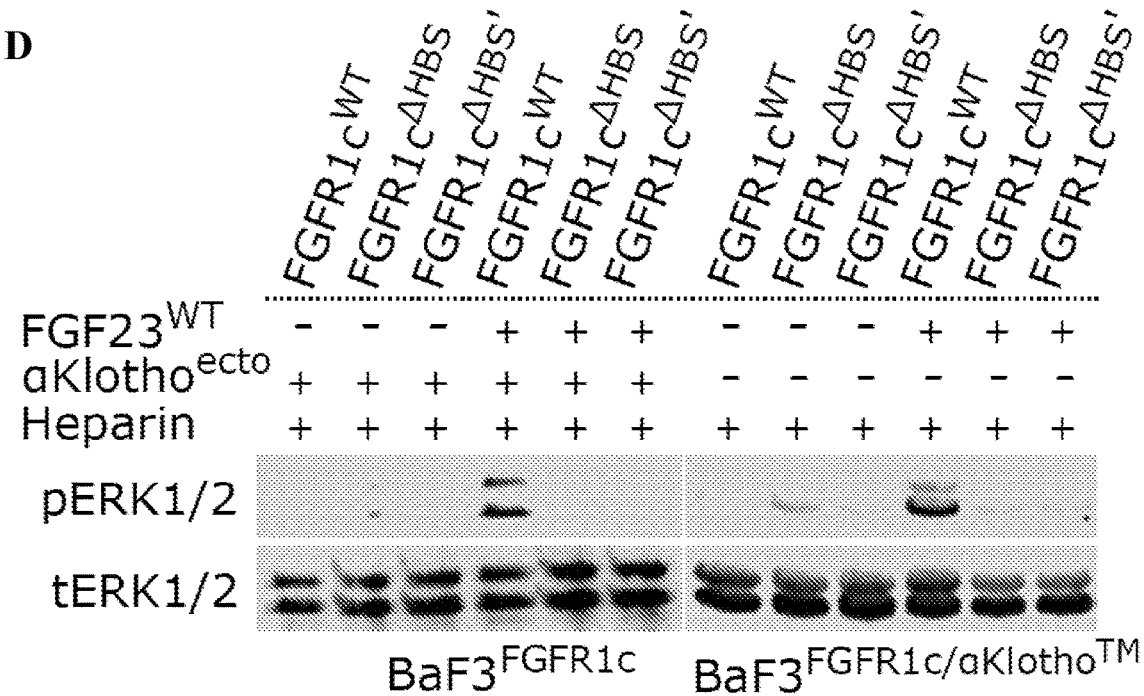
Figure 5E:
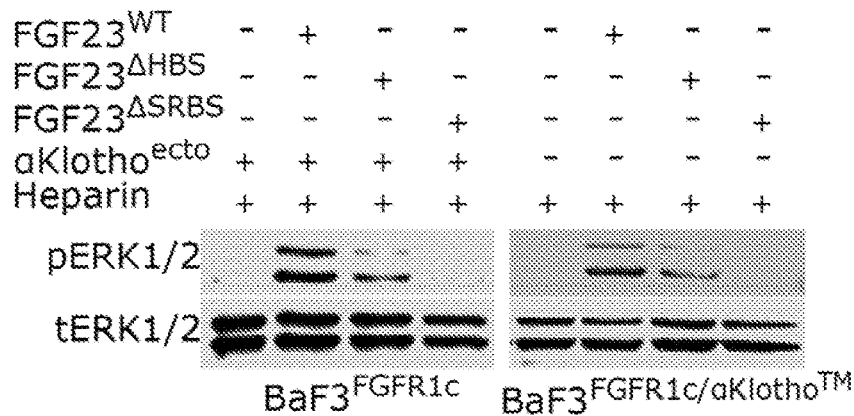
Figure 5F:
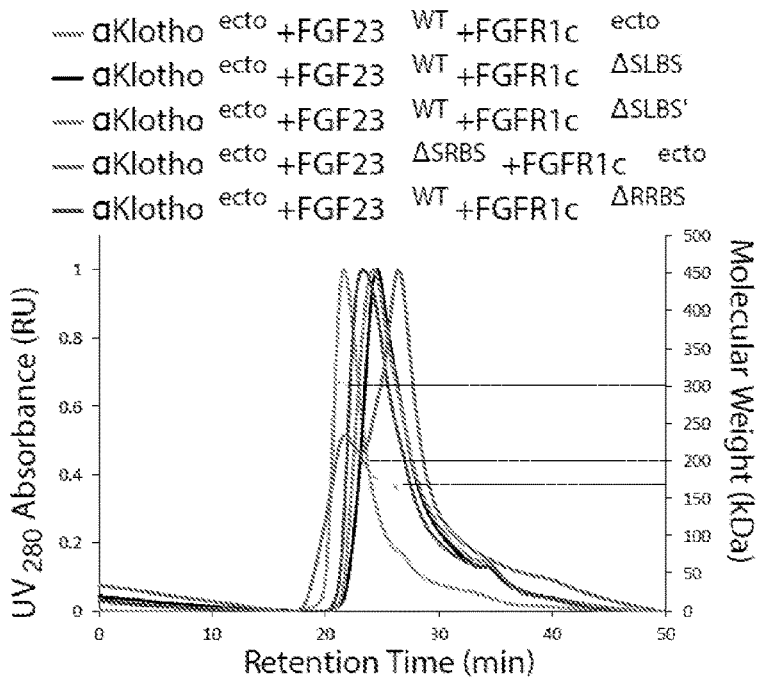
Figure 6A:
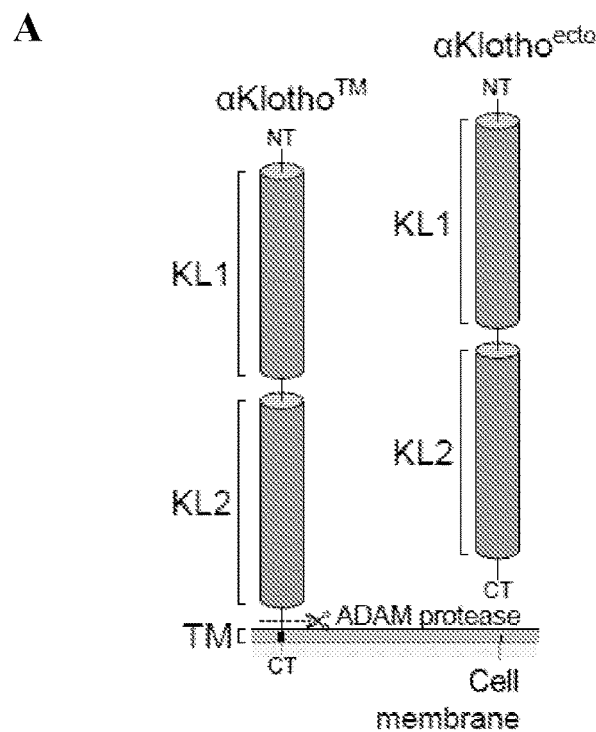
FIGS. 6A-6D show that αKlotho$^{ecto}$ functions as a coreceptor for FGF23.
Figure 6B:
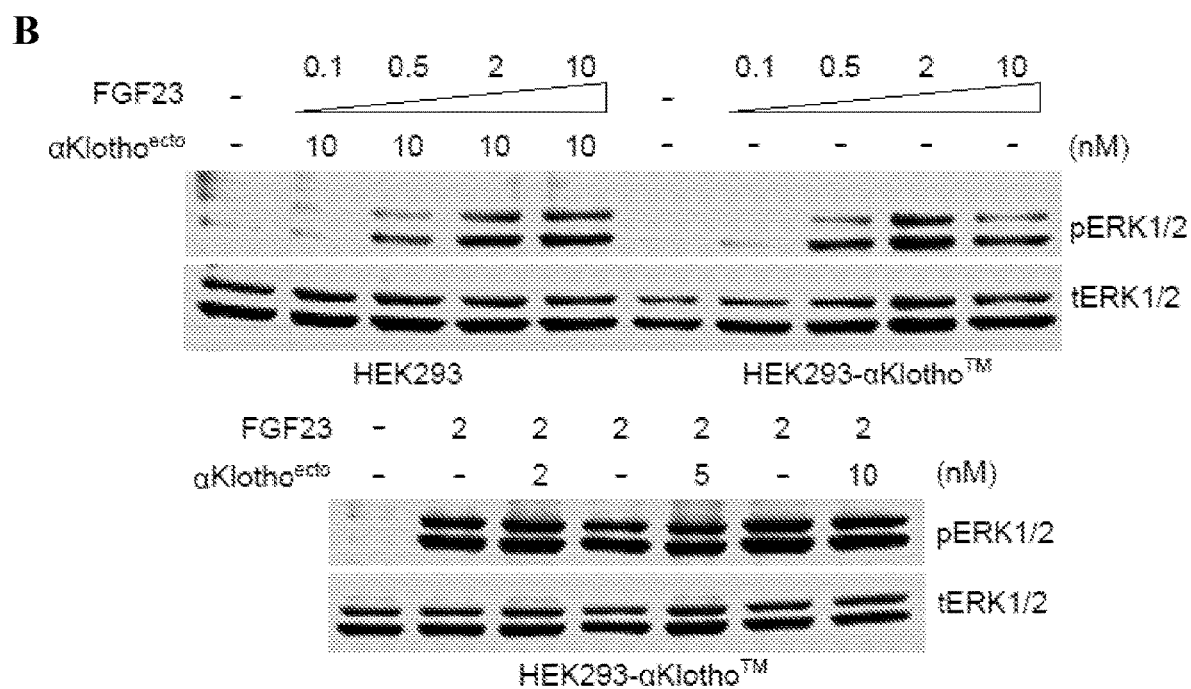
Figure 6C:
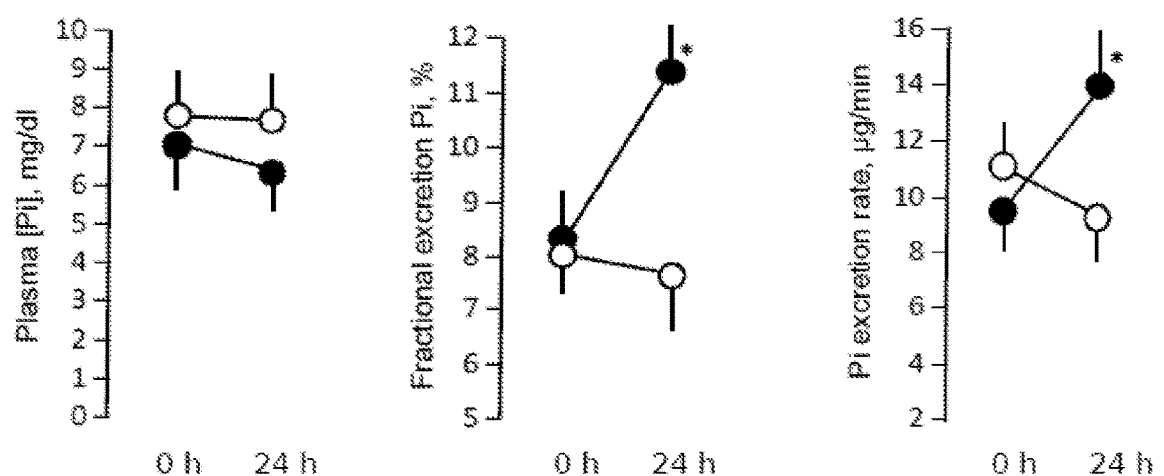
Figure 6D:
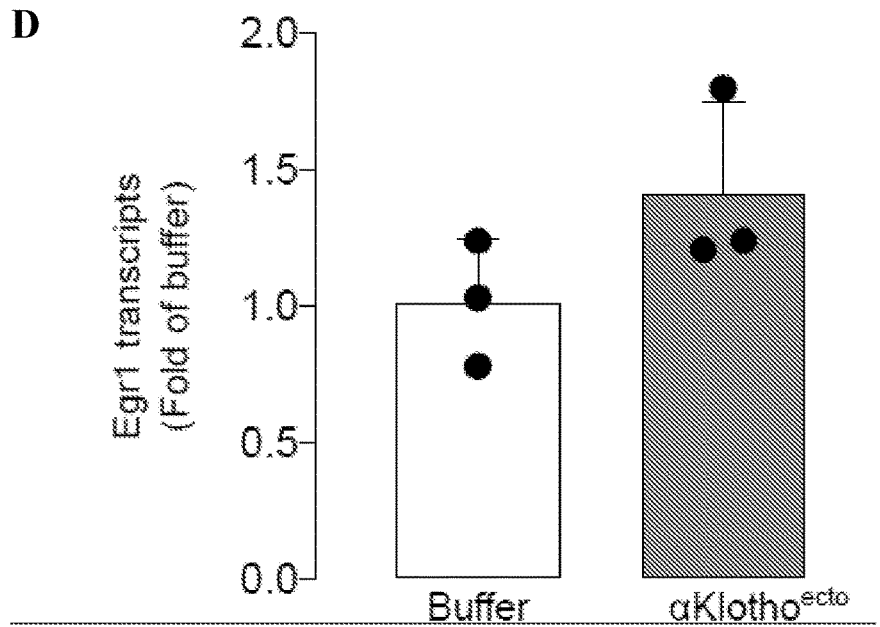
Figures 12A, 12B:
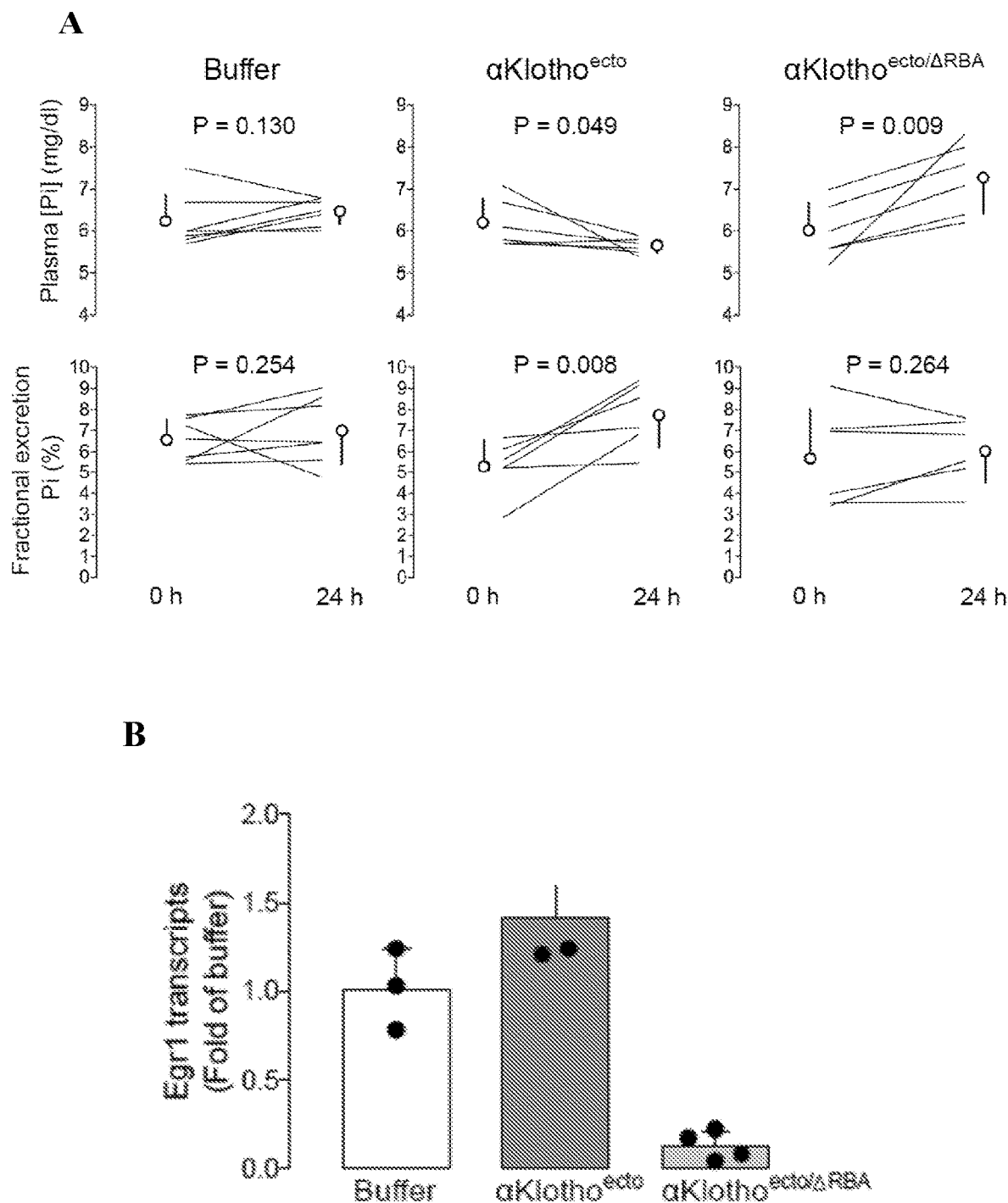
FIGS. 12A-12E show that deletion of receptor binding arm of αKlotho$^{ecto}$ generates an FGF23 ligand trap.
Figure 12C:
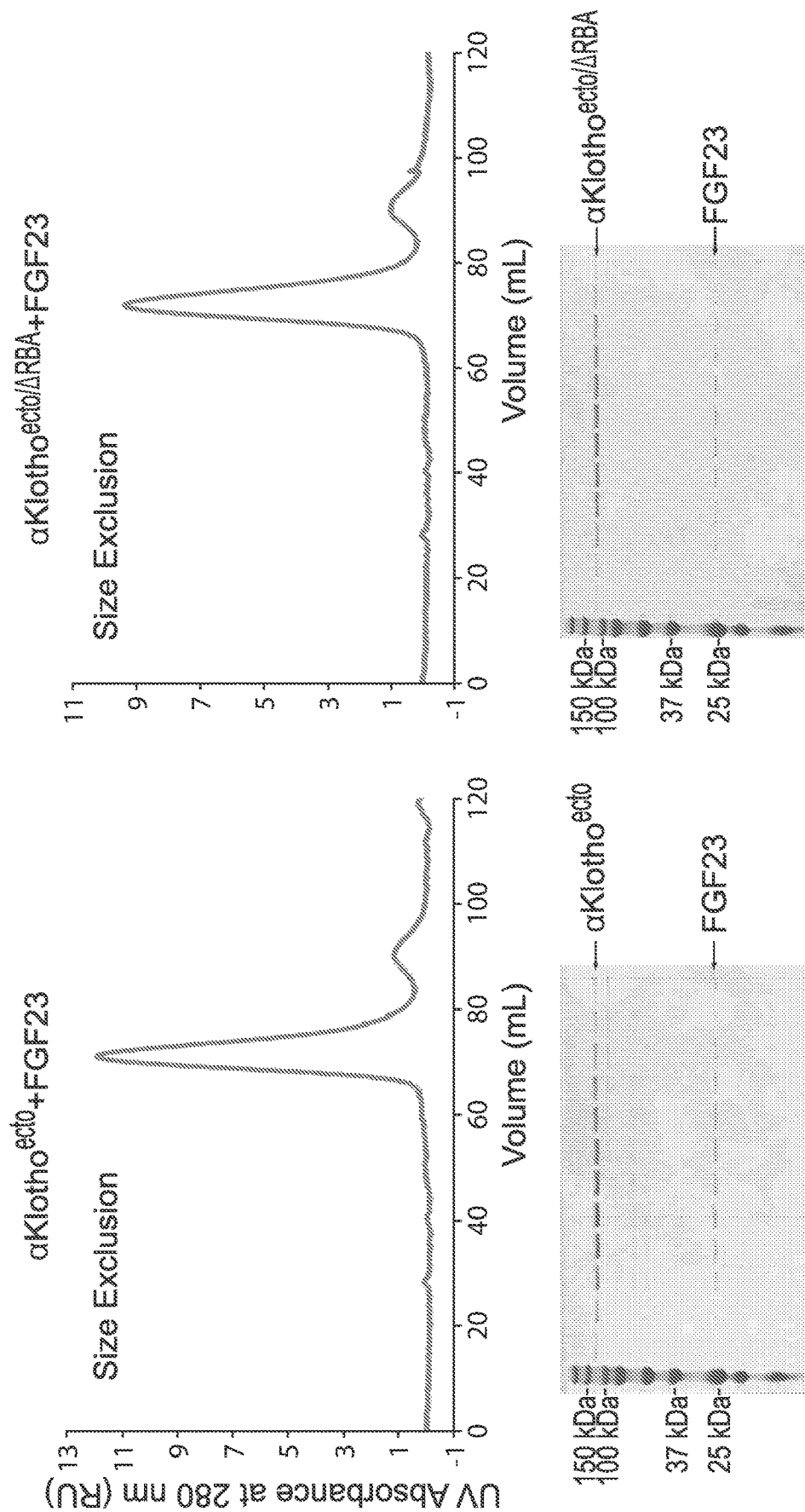
Figure 12D:
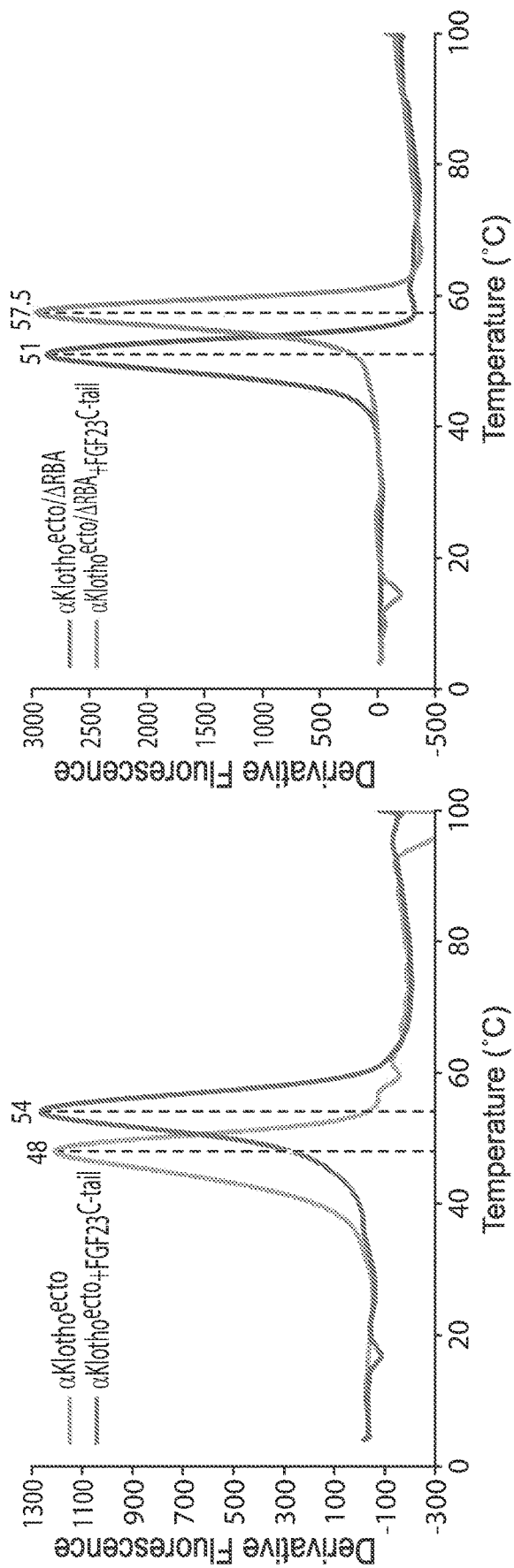
Figure 12E:
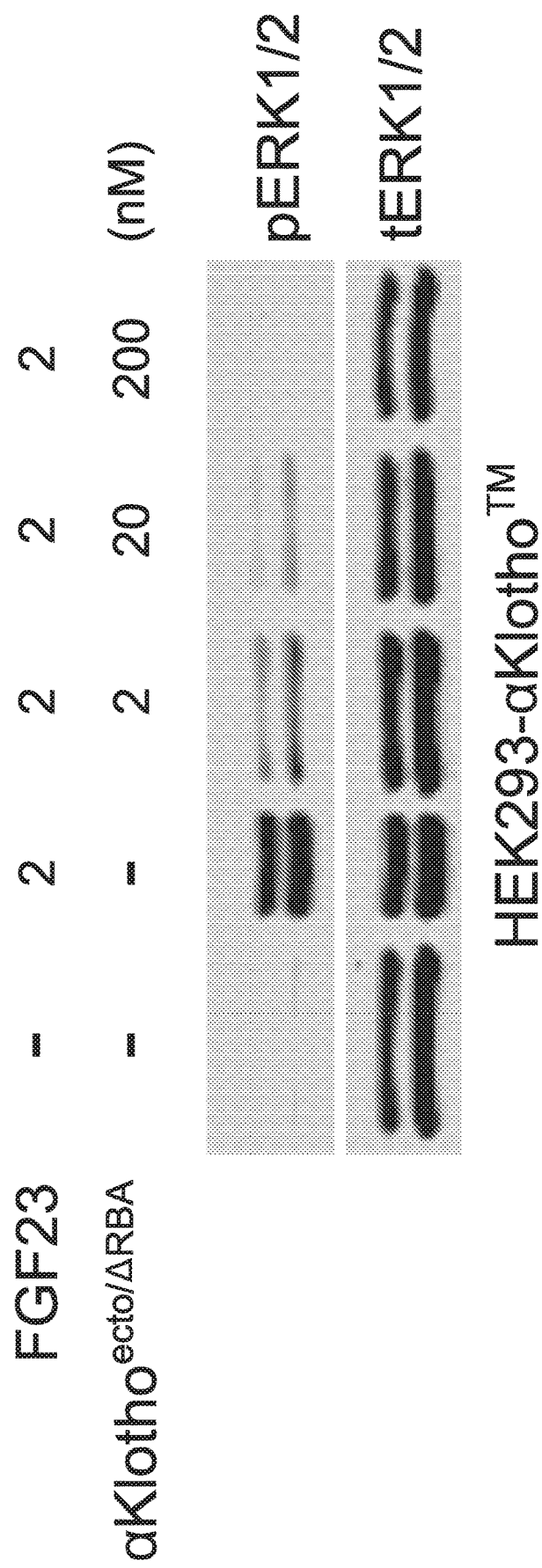

Statistics and Reproducibility: Glycoside-hydrolase activity of αKlotho$^{ecto}$, neuraminidase, and β-glucuronidase was measured in triplicate; one triplicate representative of three independent experiments is shown in FIG. 2C. Each set of immunoblot experiments, (data shown in FIGS. 4B-4E, 5C-5E, 6B, 9C, 12E, and 15B-15C), was independently repeated three times. Renal mRNA levels of Egr1 and cyclophilin were each measured in triplicate, and mean values of relative Egr1 mRNA concentrations from three independent samples for buffer control, three independent samples for αKlotho$^{ecto}$ treatment, and four independent samples for αKlotho$^{ecto/\Delta RBA}$ treatment are shown in FIGS. 6D and 12B, respectively. Protein elution profiles from size-exclusion columns shown in FIGS. 4A, 5A-5B, 5F, and 12C are each representative of three independent experiments.

The Examples of the present application demonstrate, inter alia, that circulating αKlotho$^{ecto}$ is an on-demand bona fide co-receptor for FGF23. Also described infra is the crystal structure of αKlotho$^{ecto}$ in complex with FGFR1c$^{ecto}$ and FGF23. The structure reveals that αKlotho serves as a non-enzymatic scaffold that simultaneously tethers FGFR1c and GFG23 to implement FGF23-FGFR1c proximity and hence stability. Surprisingly, heparan sulfate (HS), a mandatory cofactor for paracrine FGFs, is still required as an ancillary cofactor to promote the formation of a symmetric 2:2:2:2 FGF23-GFGR1c-αKlotho-HS quaternary signaling complex.

Example 1—Soluble αKlotho$^{ecto}$ Acts as a Co-Receptor for FGF23

To determine whether soluble αKlotho$^{ecto}$ can support FGF23 signaling, αKlotho-deficient HEK293 cells—which naturally express FGFRs—were incubated with a concentration of αKlotho$^{ecto}$ sufficient to drive all available cell surface cognate FGFRs into binary complexed form. Following brief rinses with PBS, the cells were stimulated with increasing concentrations of FGF23. In parallel, a HEK293 cell line overexpressing membrane-bound αKlotho (HEK293-αKlotho™) was treated with increasing concentrations of FGF23. The dose-response for FGF23-induced ERK phosphorylation in αKlotho$^{ecto}$-pretreated untransfected HEK293 cells was similar to that observed in HEK293-αKlotho™ cells (FIG. 6B, upper panel), suggesting that αKlotho$^{ecto}$ can serve as a co-receptor for FGF23. Pre-treatment of HEK293-αKlotho™ cells with αKlotho$^{ecto}$ did not result in any further increase in FGF23 signaling, implying that all cell surface FGFRs in this cell line were in binary FGFR-αKlotho™ form (FIG. 6B, lower panel). These results indicate that soluble and transmembrane forms of αKlotho possess a similar capacity to support FGF23 signaling. Consistent with these results, injection of wild-type mice with αKlotho$^{ecto}$ protein led to an increase in renal phosphate excretion and a decrease in serum phosphate (FIG. 6C). Notably, it also led to a 1.5-fold increase in Egr1 transcripts in the kidney (FIG. 6D), demonstrating that αKlotho$^{ecto}$ can serve as a bona fide co-receptor to support FGF23 signaling in renal proximal tubules. In light of these data, it was posited that the pleiotropic anti-aging effects of αKlotho are all dependent on FGF23.

Example 2—Structural Basis for αKlotho Co-Receptor Function

Figures 7A, 7B:
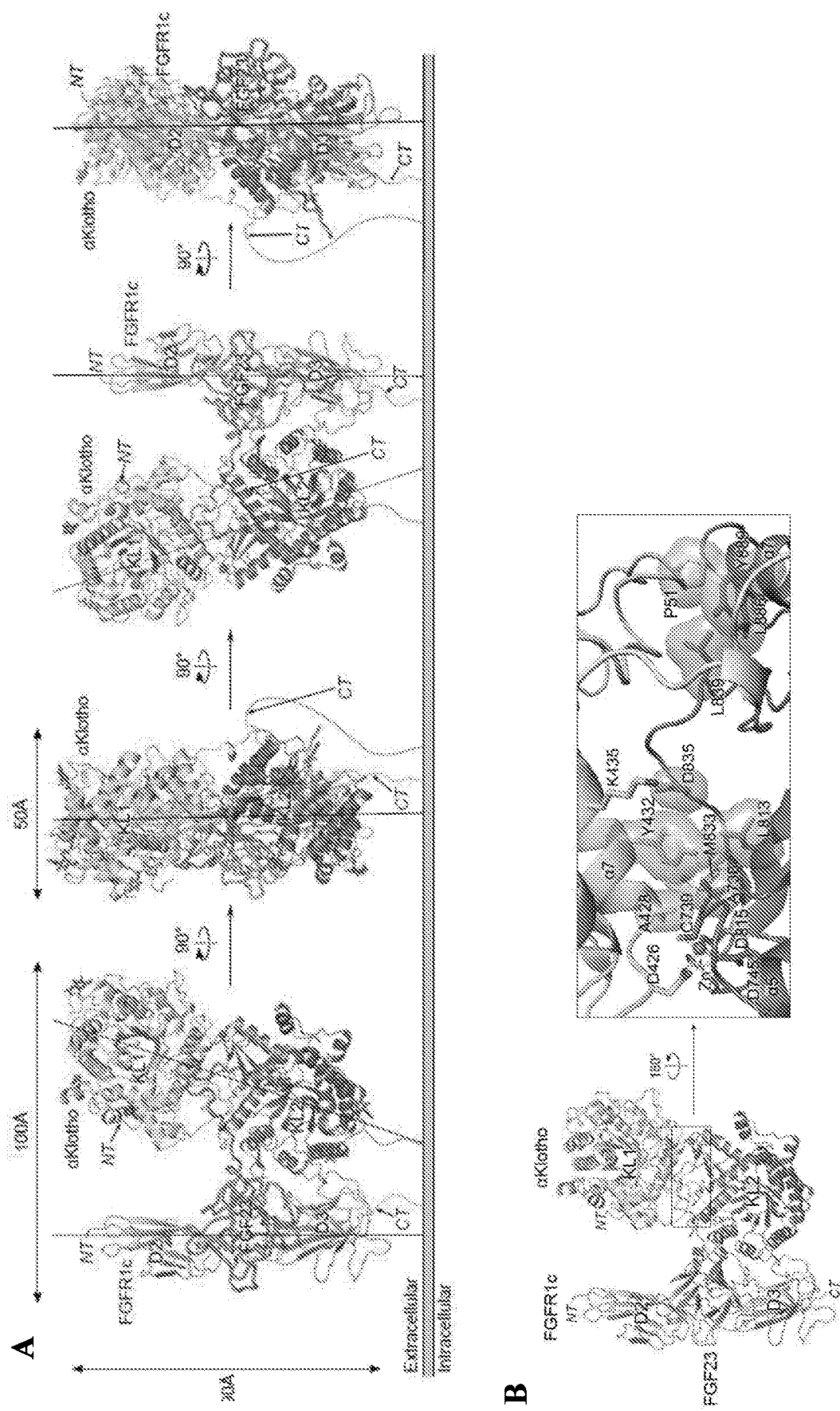
FIGS. 7A-7C show that the topology of ternary complex is consistent with its orientation on the cell surface.

The crystal structure of a human 1:1:1 FGF23-FGFR1c$^{ecto}$-αKlotho$^{ecto}$ ternary complex at 3.0 Å resolution was solved (Table 5). In this complex, αKlotho$^{ecto}$ serves as a massive scaffold, tethering both FGFR1c and FGF23 to itself. In doing so, αKlotho$^{ecto}$ enforces FGF23-FGFR1c proximity and thus augments FGF23-FGFR1c binding affinity (FIG. 1). The overall geometry of the ternary complex is compatible with its formation on the cell surface (FIG. 7A).

Figures 8A, 8B, 8C:
FIGS. 8A-8C show the structural basis for FGF23's weak FGFR-binding affinity.
Figures 9D, 9E:
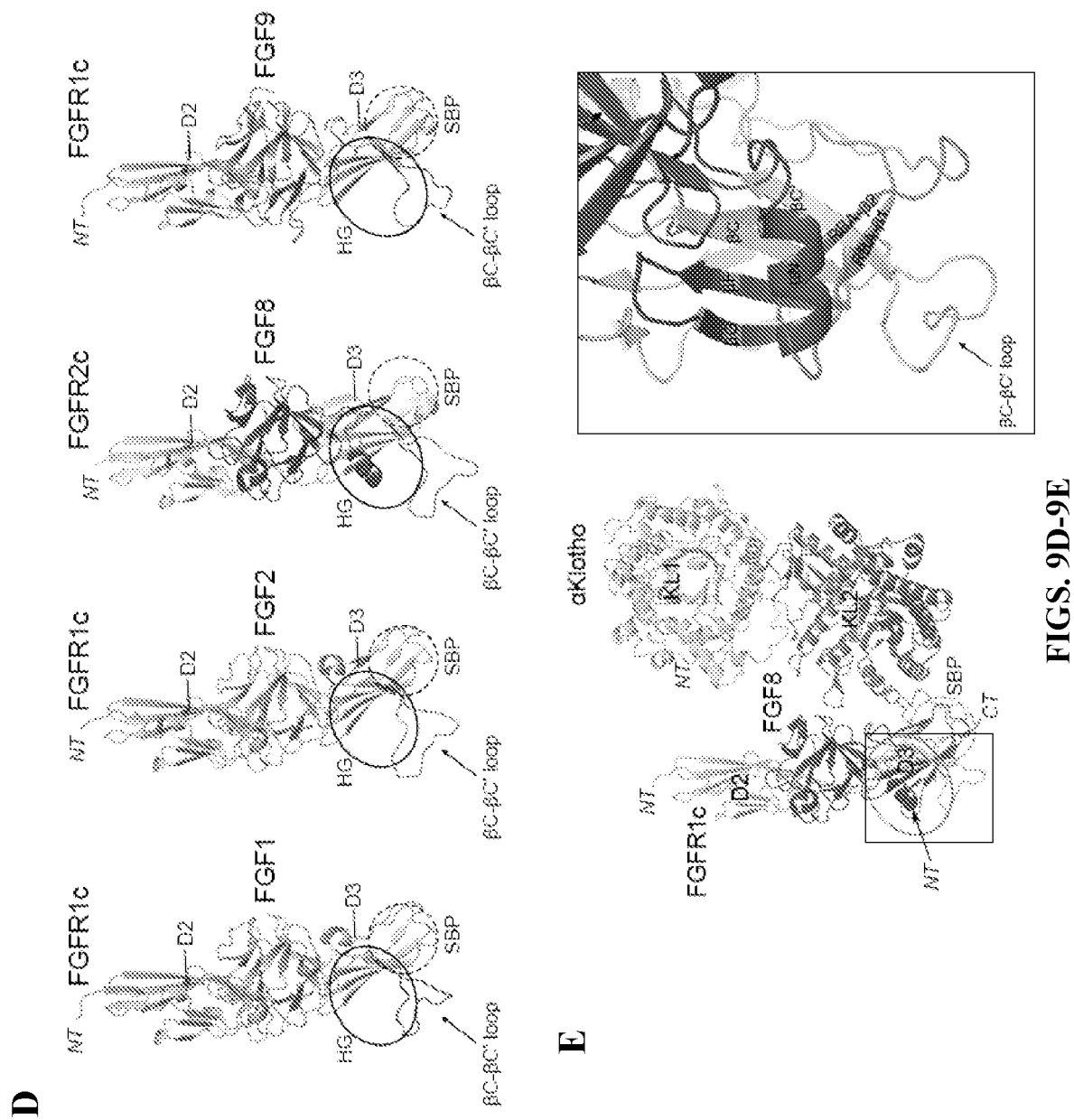

The binary FGF23-FGFR1c$^{ecto}$ complex adopts a canonical FGF-FGFR complex topology in which FGF23 is bound between the receptor's D2 and D3 domains, engaging both these domains and a short interdomain linker (FIG. 8A). However, compared to paracrine FGFs, FGF23 makes fewer/weaker contacts with the D3 domain and D2-D3 linker, explaining the inherently low affinity of FGF23 for FGFR1c (FIGS. 8B-8C). Notably, analysis of the binding interface between FGF23 and FGFR1c D3 in the crystal structure reveals specific contacts between FGF23 and a serine residue uniquely present in the "c" splice isoforms of FGFR1-3 and FGFR4 (FIG. 9A). Indeed, replacing this "c"-isoform specific serine residue with a "b"-isoform specific tyrosine impaired FGF23 signaling (FIGS. 9B-9C). The conclusion drawn is that the FGFR binding specificity inherent to FGF23 operates alongside that of αKlotho (FIGS. 9D-9E) to restrict FGF23 signaling to the "c" splice isoforms and FGFR4 (Urakawa et al., "Klotho Converts Canonical FGF Receptor into a Specific Receptor for FGF23," Nature 444(7120):770-774 (2006) and Kurosu et al., "Regulation of Fibroblast Growth Factor-23 Signaling by Klotho," J. Biol. Chem. 281:6120-6123 (2006), each of which is hereby incorporated by reference in its entirety).

Figures 3A, 3B, 3C:
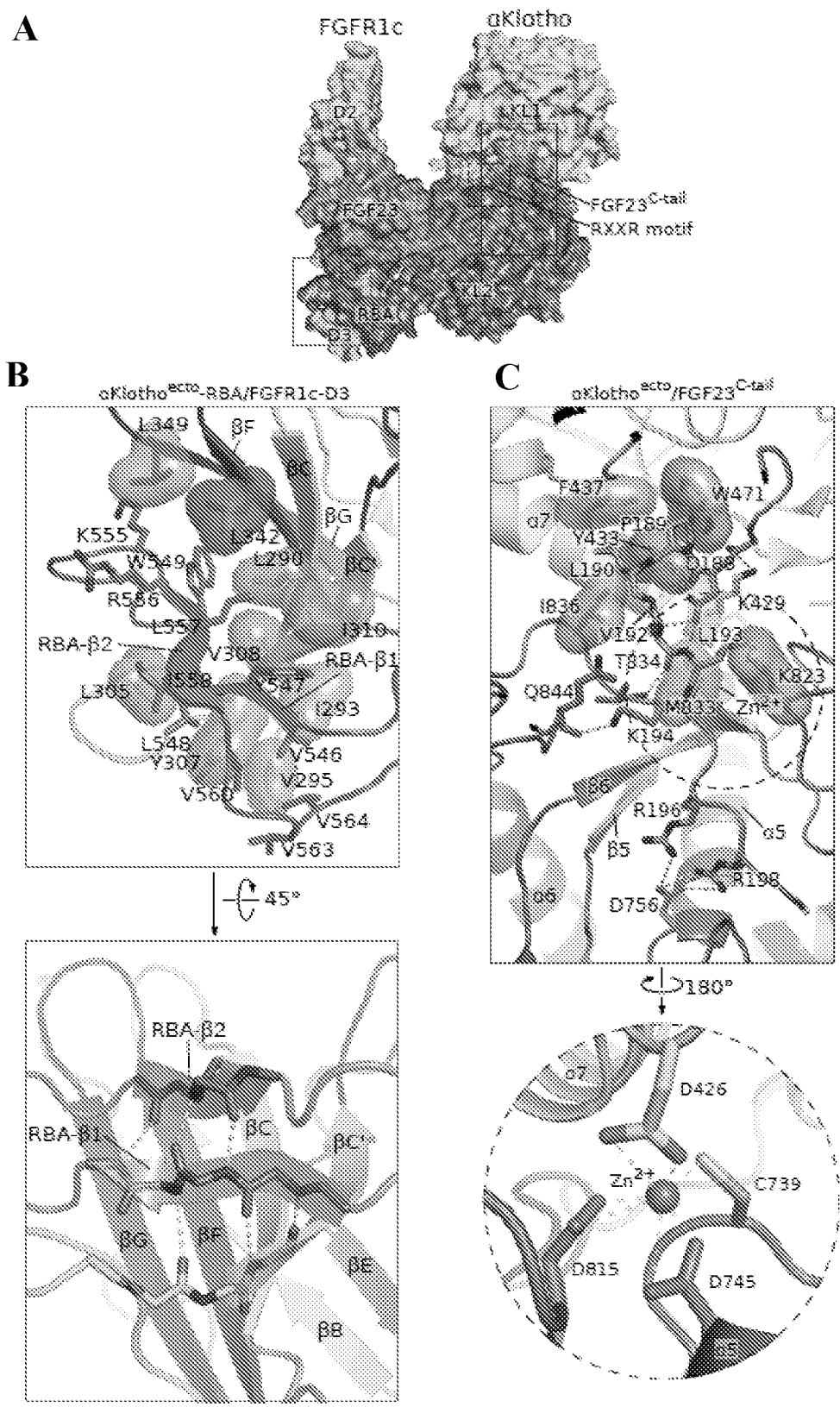
FIGS. 3A-3C show that αKlotho simultaneously tethers FGFR 1c by its D3 domain and FGF23 by its C-terminal tail.
Figure 7C:
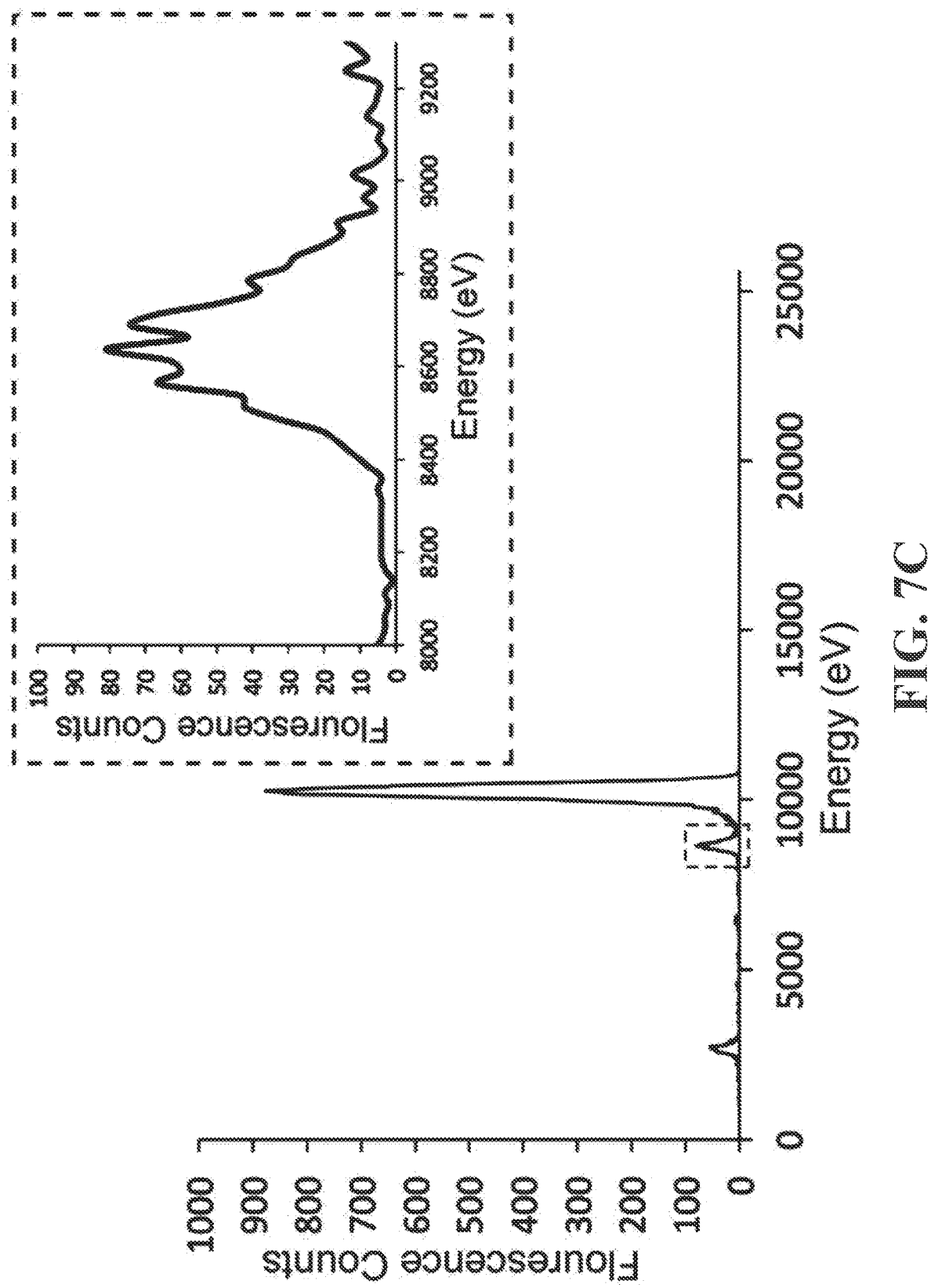

In the ternary complex, αKlotho$^{ecto}$ exists in an extended conformation. Consistent with their sequence homology to the glycoside hydrolase A (GH-A) clan (Henrissat et al., "Structural and Sequence-Based Classification of Glycoside Hydrolases," Curr. Opin. Struct. Biol. 7(5):637-644 (1997), which is hereby incorporated by reference in its entirety), αKlotho KL1 (Glu-34 to Phe-506) and KL2 (Leu-515 to Ser-950) domains each assume a $(13a)_8$ TIM barrel fold consisting of an inner eight-stranded parallel β-barrel and eight surrounding α-helices (FIG. 2A and FIG. 10A). The two KL domains are connected by a short, proline-rich and hence stiff linker (Pro-507 to Pro-514) (FIGS. 1A-1B). KL1 sits atop KL2, engaging it via a few interdomain contacts involving the N-terminus preceding the β1 strand, the α7 helix of KL1, and the β5α5, β6α6 loops and the α7 helix of KL2 (FIGS. 7A-7B). Intriguingly, one of the interdomain contacts is mediated by a $Zn^{2+}$ ion (FIG. 3C and FIGS. 7B-7C). These contacts stabilize the observed elongated conformation of αKlotho$^{ecto}$, creating a deep cleft between the two KL domains. This merges with a wide-open central β-barrel cavity in KL2, and forms a large binding pocket that tethers the distal C-terminal tail of FGF23 past the $^{176}$Arg-His-Thr-Arg$^{179}$ proteolytic cleavage site (FIG. 1B). Meanwhile, the long β1α1 loop of KL2 (FIG. 2A) protrudes as much as 35 Å away from the KL2 core to latch onto the FGFR1c D3 domain, thus anchoring the receptor to αKlotho (FIG. 1B). Accordingly, this KL2 loop was named the "Receptor Binding Arm" (RBA; residues 530-578; FIG. 10A).

The TIM barrels of KL1 and KL2 were superimposed onto that of Klotho Related Protein (KLrP; also known as GBA3), the cytosolic member of the Klotho family with proven glycosylceramidase activity (Hayashi et al., "Klotho-Related Protein is a Novel Cytosolic Neutral Beta-Glycosylceramidase," *J. Biol. Chem.* 282(42):30889-30900 (2007), which is hereby incorporated by reference in its entirety). This comparison revealed major conformational differences in the loops surrounding the entrance to the catalytic pocket in KL1 and KL2 (FIG. 2B and FIGS. 10B-10D). Moreover, both KL domains lack one of the key catalytic glutamates deep within the putative catalytic pocket. These substantial differences are incompatible with an intrinsic glycosidase activity for αKlotho (Chang et al., "The Beta-Glucuronidase Klotho Hydrolyzes and Activates the TRPV5 Channel," *Science* 310(5747):490-493 (2005) and Cha et al., "Removal of Sialic Acid Involving Klotho Causes Cell-Surface Retention of TRPV5 Channel Via Binding to Galectin-1," *PNAS USA* 105(28):9805-9810 (2008), each of which is hereby incorporated by reference in its entirety). Indeed, αKlotho$^{ecto}$ failed to hydrolyze substrates for both sialidase and β-glucuronidase in vitro (FIG. 2C). Together, these data define αKlotho as the only known example of a TIM barrel protein that serves purely as a non-enzymatic molecular scaffold.

Example 3—Binding Interface Between αKlotho and FGFR1c

Figures 11A, 11B:
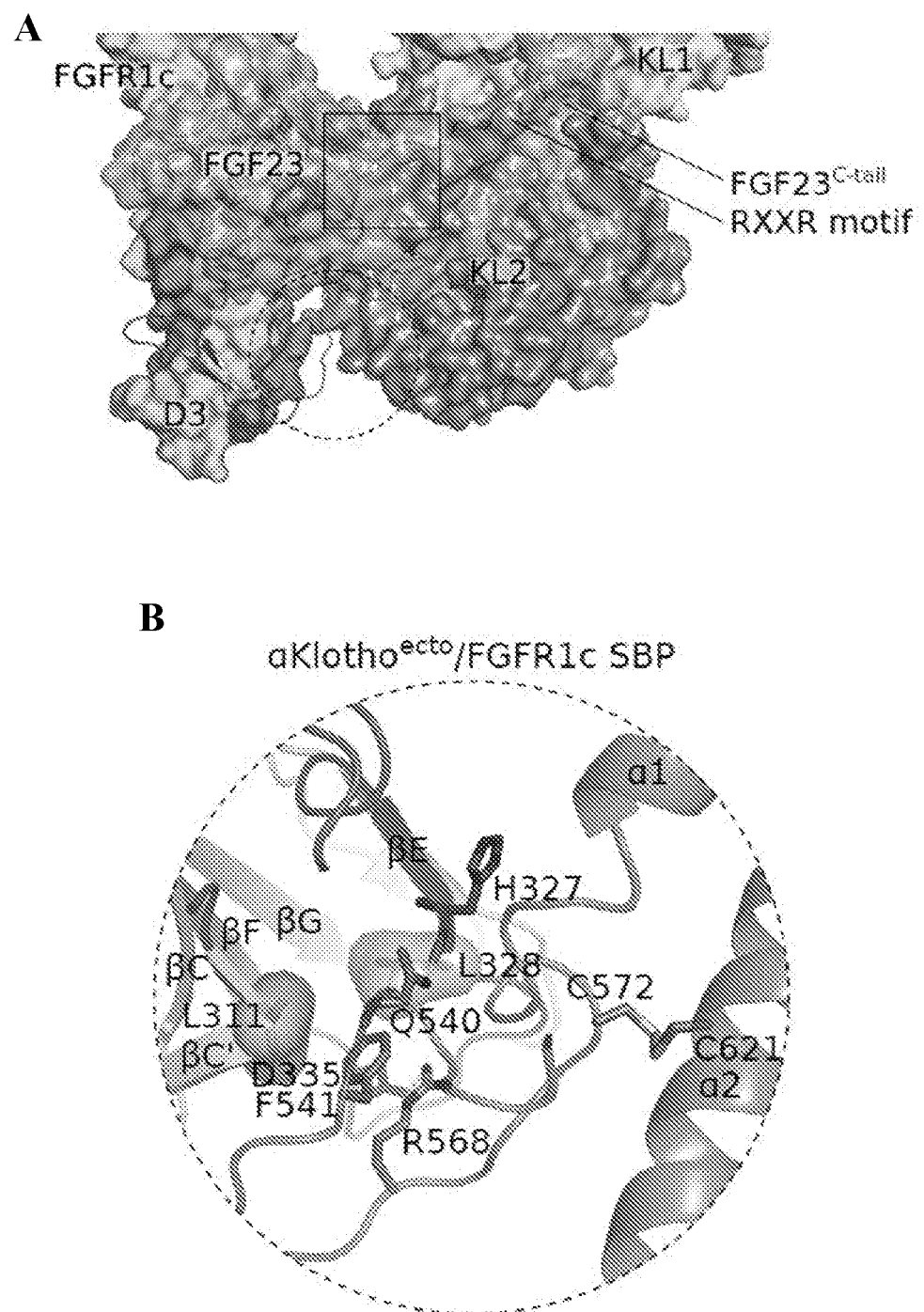
FIGS. 11A-11C show the αKlotho interaction with rigid core of FGF23 and a second binding pocket next to the hydrophobic groove in FGFR1c D3.

The interface between αKlotho RBA and FGFR1c D3 (FIG. 3A) buries over 2,200 Å$^2$ of solvent-exposed surface area, which is consistent with the high affinity of αKlotho binding to FGFR1c ($K_D$=72 nM)$^{10}$. At the distal tip of the RBA, residues $^{547}$Tyr-Leu-Trp$^{549}$ and $^{556}$Ile-Leu-Arg$^{558}$ form a short β-strand pair (RBA-β1:RBA-β2) as their hydrophobic side chains are immersed in a wide hydrophobic groove between the four-stranded βC'-βC-βF-βG sheet and the βC-βC' loop of FGFR1c D3 (FIG. 3B, upper panel). The RBA-β1:RBA-β2 strand pair forms an extended sheet with the βC'-βC-βF-βG sheet of D3 as the backbone atoms of RBA-β1 and D3 βC' make three hydrogen bonds which further augment the interface (FIG. 3B, lower panel). Residues at the proximal end of the RBA engage a second smaller binding pocket at the bottom edge of D3 next to the hydrophobic groove (FIGS. 11A-11B). Both αKlotho binding pockets in the receptor D3 domain differ between "b" and "c" splice isoforms. Leu-342, for example, is strictly conserved in the "c" splice isoforms of FGFR1-3 and FGFR4. This explains the previously described binding selectivity of αKlotho for this subset of FGFRs (FIG. 9A) (Urakawa et al., "Klotho Converts Canonical FGF Receptor into a Specific Receptor for FGF23," *Nature* 444(7120): 770-774 (2006); Kurosu et al., "Regulation of Fibroblast Growth Factor-23 Signaling by Klotho," *J. Biol. Chem.* 281:6120-6123 (2006); and Goetz et al., "Klotho Coreceptors Inhibit Signaling by Paracrine Fibroblast Growth Factor 8 Subfamily Ligands," *Mol. Cell. Biol.* 32(10):1944-1954 (2012), each of which is hereby incorporated by reference in its entirety).

Figure 4A:
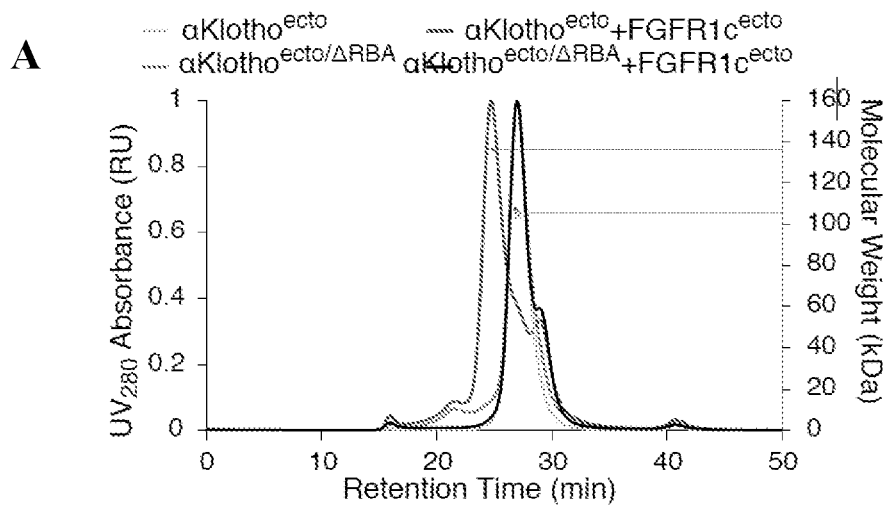
FIGS. 4A-4E show results from mutagenesis experiments that validate the crystallographically-deduced mode of ternary complex formation.
Figure 4B:
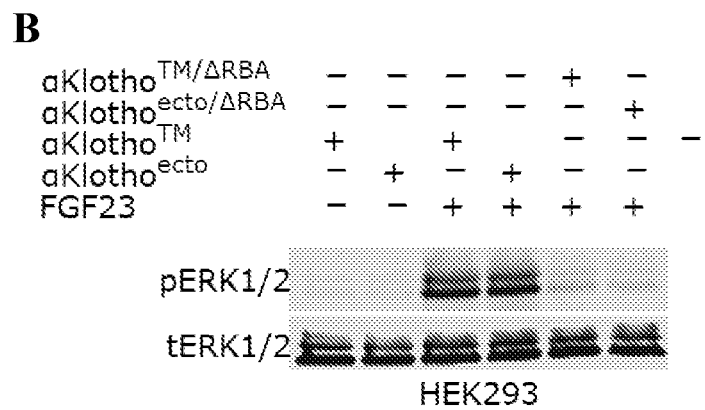

Consistent with the crystal structure, soluble αKlotho lacking the RBA (αKlotho$^{ecto/\Delta RBA}$) failed to form a binary complex with FGFR1c$^{ecto}$ in solution (FIG. 4A) and hence could not support FGF23 signaling (FIG. 4B). Likewise, membrane-bound αKlotho lacking the RBA (αKlotho$^{TM/\Delta RBA}$) was also disabled in acting as a FGF23 co-receptor (FIG. 4B). Importantly, αKlotho$^{ecto/\Delta RBA}$ did not exhibit any phosphaturic activity in vivo (FIG. 12A). On the contrary, the αKlotho$^{ecto/\Delta RBA}$ mutant antagonized the activity of native αKlotho by sequestering FGF23 into functionally inactive binary complexes, i.e. by acting as an FGF23 ligand trap (FIG. 12A-12E). These data refute the concept that αKlotho$^{ecto}$ functions as an FGF23-independent phosphaturic enzyme (Hu et al., "Klotho: A Novel Phosphaturic Substance Acting as an Autocrine Enzyme in the Renal Proximal Tubule," *FASEB J.* 24(9):3438-3450 (2010), which is hereby incorporated by reference in its entirety). This conclusion is supported by a gene knockout study which compared the phenotypes of Fgf23$^{-/-}$, Klotho$^{-/-}$, and Fgf23$^{-/-}$/Klotho$^{-/-}$ mice (Andrukhova et al., "Klotho Lacks an FGF23-Independent Role in Mineral Homeostasis," *J. Bone Miner. Res.* 32(10):2049-2061 (2017), which is hereby incorporated by reference in its entirety).

Example 4—Binding Interface Between αKlotho and FGF23

Figure 11C:
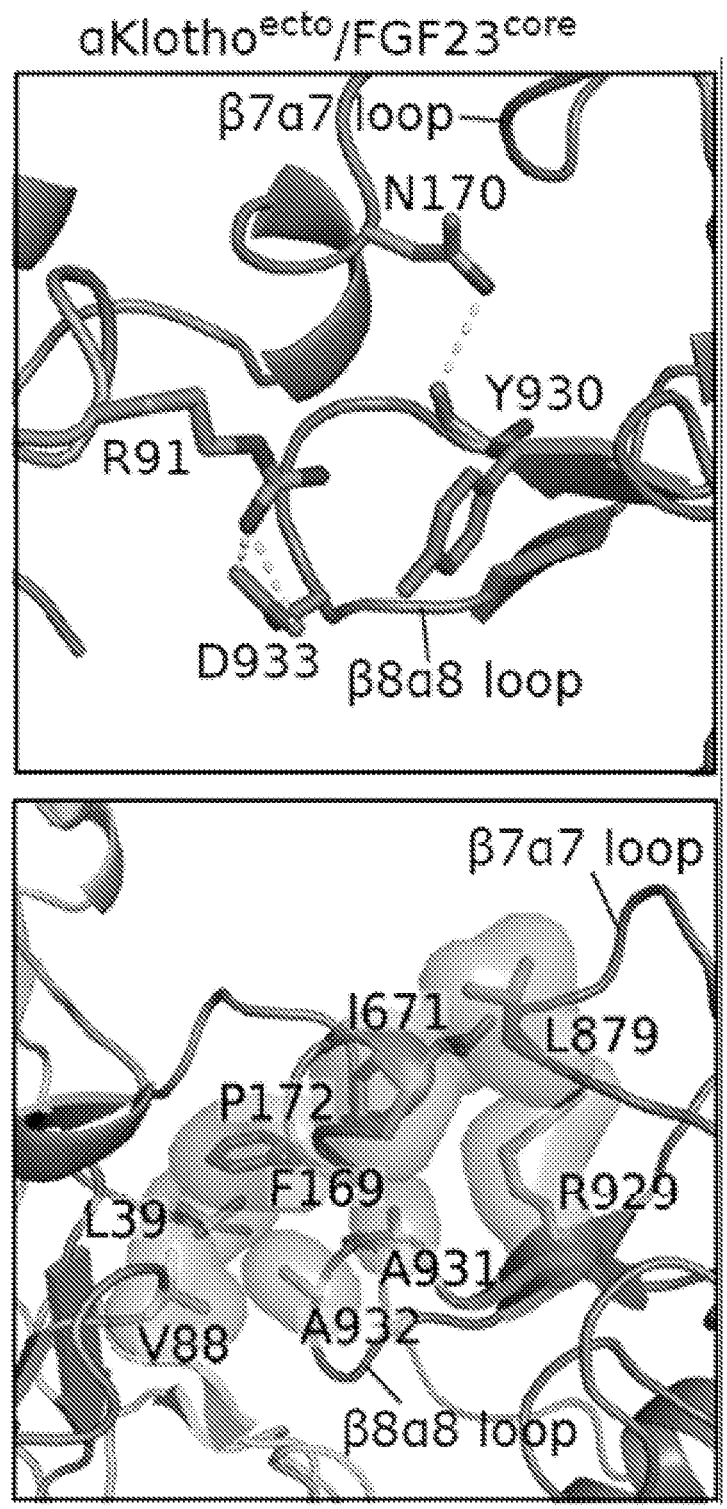

Regions from both KL domains act together to recruit FGF23 (FIG. 1B), thus explaining why only an intact αKlotho ectodomain is capable of supporting FGF23 signaling (Kurosu et al., "Regulation of Fibroblast Growth Factor-23 Signaling by Klotho," *J. Biol. Chem.* 281:6120-6123 (2006) and Wu et al., "C-Terminal Tail of FGF19 Determines its Specificity Toward Klotho Co-Receptors," *J. Biol. Chem.* 283(48):33304-33309 (2008), each of which is hereby incorporated by reference in its entirety). The interactions between FGF23 and αKlotho result in the burial of a large amount of solvent-exposed surface area (2,732 Å$^2$), of which nearly two-thirds (1961 Å$^2$) are buried between the FGF23 C-terminal tail and αKlotho, with the remaining one-third buried between the FGF23 core and αKlotho (FIG. 3A). At the interface between αKlotho and FGF23 C-terminal tail, FGF23 residues $^{188}$Asp-Pro-Leu-Asn-Val-Leu$^{193}$ adopt an unusual cage-like conformation (FIGS. 3A, 3C) which is tethered by residues from both KL domains via hydrogen bonds and hydrophobic contacts deep inside the KL1-KL2 cleft (FIG. 3C). Further downstream, the side chains of Lys-194, Arg-196, and Arg-198 of the FGF23 C-terminal tail dip into the central barrel cavity of KL2, making hydrogen bonds with multiple αKlotho residues (FIG. 3C). At the interface between the FGF23 β-trefoil core and αKlotho, residues from the β5-136 turn and the αC helix of FGF23 make hydrogen bonds and hydrophobic contacts with residues in the short β7-α7 and β8-α8 loops at the upper rim of the KL2 cavity (FIGS. 11A, 11C).

Figure 4C:
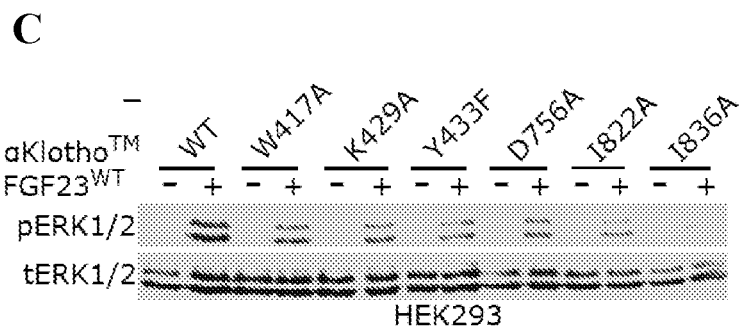
Figure 4D:
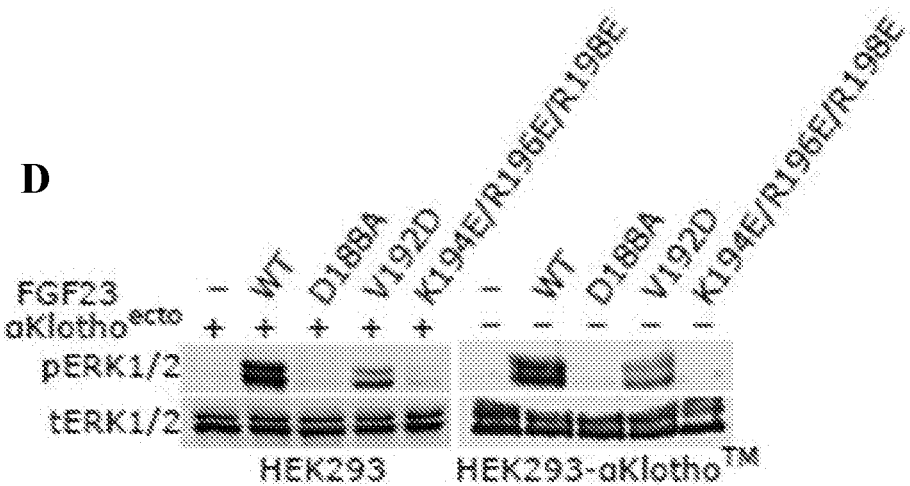
Figure 4E:
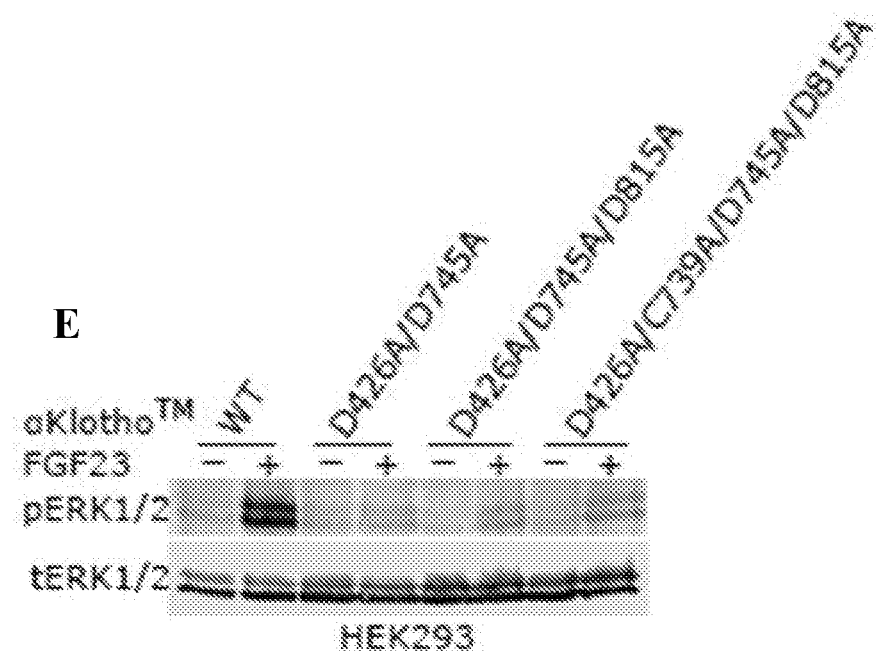

To test the biological relevance of the observed contacts between αKlotho and FGF23 C-terminal tail, multiple mutations were introduced into αKlotho™ and FGF23 in order to disrupt αKlotho-FGF23 binding (FIG. 4C). Consistent with the structure-based predictions, all αKlotho™ mutants showed an impaired ability to support FGF23 signaling (FIG. 4C). The FGF23 mutants also exhibited a reduced ability to signal, regardless of whether soluble or membrane-bound αKlotho served as co-receptor (FIG. 4D). Remarkably, the FGF23$^{D188A}$ mutant (which eliminates the intramolecular hydrogen bonds that support cage conformation) was totally inactive, underscoring the importance of the cage-like conformation in the tethering of FGF23 to αKlotho. Notably, tethering of this cage-like structure requires a precise alignment of residues from both KL domains deep within the KL1-KL2 cleft (FIG. 3C), implying that their correct apposition is critically important for αKlotho co-receptor activity. These structural observations suggest that the bound Zn$^{2+}$ ion serves as a prosthetic group in αKlotho by minimizing interdomain flexibility and hence promoting co-receptor activity. Consistent with such a role, mutants of membrane-anchored αKlotho™ carrying alanine in place of two, three, or all four $Zn^{2+}$ coordinating amino acids (FIG. 3C) showed a reduced ability to support FGF23 signaling (FIG. 4E). Together with the data on the impact of RBA deletion, these results corroborate the biological relevance of the crystallographically-deduced mode by which αKlotho implements FGF23-FGFR1c proximity and thus confers high binding affinity.

Example 5—FGF23 Signaling is αKlotho and HS-Dependent

Both FGF23 and FGFR1c have a measurable (albeit weak) binding affinity for HS. Because HS is ubiquitously expressed, whether it participates in the apparent αKlotho$^{ecto}$-mediated FGF23-FGFR dimerization in cell-based and in vivo experiments was investigated. The molecular mass of the ternary complex was analyzed in the absence and presence of increasing molar equivalents of homogenously sulfated heparin hexasaccharide (HS6). Consistent with previous observations, in the absence of HS6, the ternary complex migrated as a monomeric species (Goetz et al., "Isolated C-Terminal Tail of FGF23 Alleviates Hypophosphatemia by Inhibiting FGF23-FGFR-Klotho Complex Formation," *PNAS USA* 107(1):407-412 (2010), which is hereby incorporated by reference in its entirety) with an apparent molecular mass of 150 kDa, in good agreement with the theoretical value for a 1:1:1 complex (160 kDa) (FIG. 5A). With increasing molar ratios of HS6 to ternary complex, the peak for monomeric ternary complex diminished, while a new peak with a molecular mass of 300 kDa (corresponding to a 2:2:2 FGF23-FGFR1c$^{ecto}$-αKlotho$^{ecto}$ dimer) appeared and increased in prominence. Excess HS6 beyond a 1:1 molar ratio of HS6 to ternary complex did not lead to any further increase in the amount of dimer complex formed, as judged by the integrated area of the dimer complex peak (FIG. 5A). These results indicate that HS is required for the dimerization of 1:1:1 FGF23-FGFR1c$^{ecto}$-αKlotho$^{ecto}$ complexes, and that at least a 1:1 molar ratio of HS6 to ternary complex is required for complete dimerization of the complex in solution (FIG. 5A). To further confirm the HS-dependency of dimerization, mutations were introduced into the HS-binding sites of FGFR1c (K160Q/K163Q, FGFR1c$^{\Delta HBS}$, and K207Q/R209Q, FGFR1c$^{\Delta HBS'}$) and FGF23 (R140A/R143A; FGF23$^{\Delta HBS}$). Neither mutating the HS-binding site in FGFR1c nor mutating that site in FGF23 impacted the formation of a monomeric 1:1:1 FGF23-FGFR1c-αKlotho complex in solution, demonstrating that αKlotho-mediated stabilization of the FGF23-FGFR complex is HS-independent. However, ternary complexes containing any of these three mutants failed to dimerize in the presence of HS6 (FIG. 5B).

Reconstitution experiments in the context of BaF3 cells (an FGFR, □Klotho, and HS triple deficient cell line (Ornitz et al., "Heparin is Required for Cell-Free Binding of Basic Fibroblast Growth Factor to a Soluble Receptor and for Mitogenesis in Whole Cells," *Mol. Cell Biol.* 12(1):240-247 (1992), which is hereby incorporated by reference in its entirety) showed that both soluble αKlotho$^{ecto}$ and membrane-bound αKlotho™ required HS to support FGF23-mediated FGFR1c activation in a more physiological context (FIG. 5C). The impact of the HS-binding site mutations in FGFR1c and FGF23 on FGFR1c activation by FGF23 in BaF3 cells was also examined (FIG. 5D). In agreement with the solution binding data, activation by FGF23 of HS-binding site mutants of FGFR1c in BaF3 cells was markedly impaired, regardless of whether soluble or membrane-bound αKlotho served as the co-receptor (FIG. 5D). Similarly, the HS-binding site mutant of FGF23 showed a significantly reduced ability to activate FGFR1c (FIG. 5E). These in vitro and cell-based analyses unequivocally demonstrate that whereas HS fulfills a dual role in paracrine FGF signaling—enhancing 1:1 FGF-FGFR binding and promoting 2:2 FGF-FGFR dimerization—it shares this task with αKlotho in FGF23 signaling. Thus, αKlotho primarily acts to promote 1:1 FGF23-FGFR1c binding, whereas HS induces dimerization of the resulting FGF23-FGFR1c-αKlotho complexes.

Figure 5G:
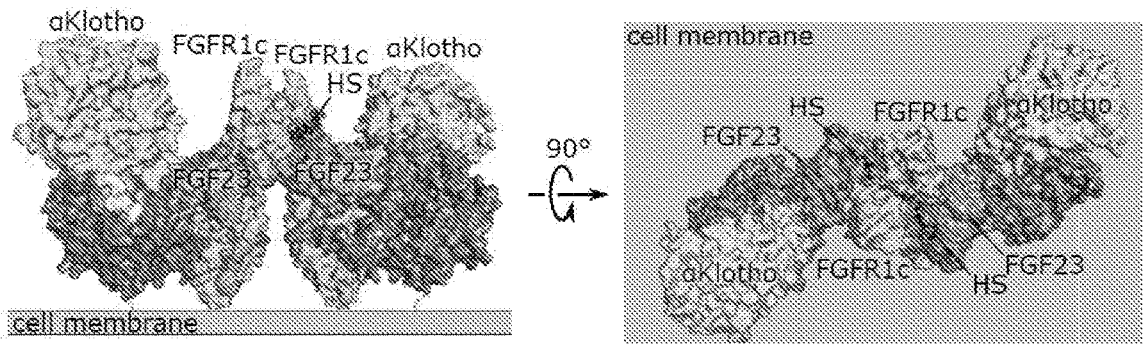
Figure 13A:
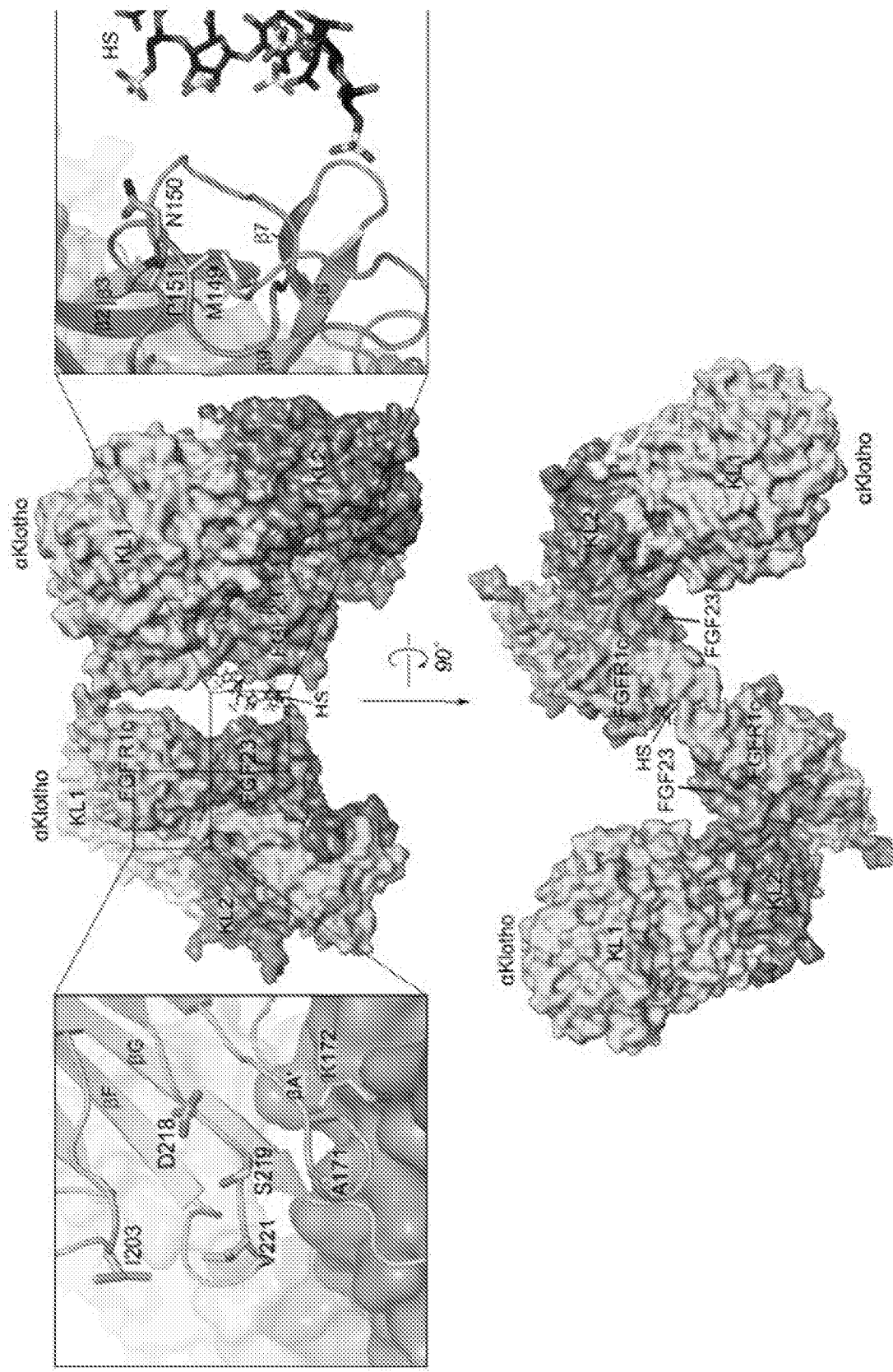
FIGS. 13A-13B show FGF23-FGFR 1c$^{ecto}$-αKlotho$^{ecto}$-HS quaternary dimer models.
Figure 13B:
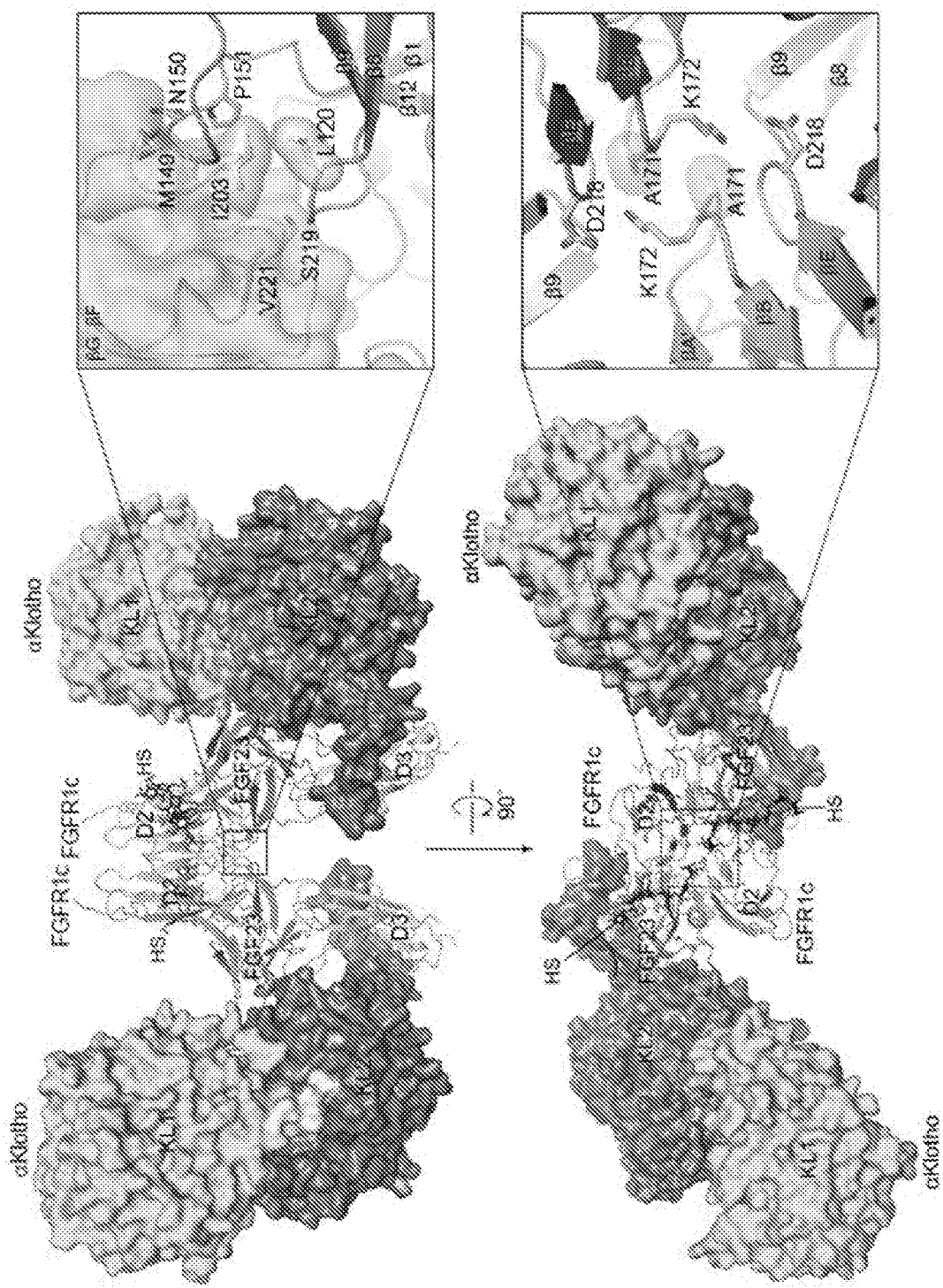

Based on the crystallographically-deduced 2:2:2 (PDB ID: 1FQ9) (Schlessinger et al., "Crystal Structure of a Ternary FGF-FGFR-Heparin Complex Reveals a Dual Role for Heparin in FGFR Binding and Dimerization," *Mol. Cell* 6(3):743-750 (2000), which is hereby incorporated by reference in its entirety) and 2:2:1 (PDB ID: 1E00) (Pellegrini et al., "Crystal Structure of Fibroblast Growth Factor Receptor Ectodomain Bound to Ligand and Heparin," *Nature* 407(6807):1029-1034 (2000), which is hereby incorporated by reference in its entirety) paracrine FGF-FGFR-HS dimerization models, two distinct HS-induced 2:2:2 endocrine FGF23-FGFR1c-αKlotho quaternary dimers can be envisioned that differ dramatically in the composition of the dimer interface (FIG. 13). Specifically, in the 2:2:2:1 model, there would be no protein-protein contacts between the two 1:1:1 FGF-FGFR-αKlotho protomers (FIG. 13A). By contrast, in the 2:2:2:2 model, FGF23 and FGFR from one 1:1:1 FGF-FGFR-αKlotho protomer would interact with the D2 domain of FGFR in the adjacent 1:1:1 FGF-FGFR-αKlotho protomer across a two-fold dimer interface (FIG. 13B). Based on the fundamental differences in the composition of the dimer interface between these two models, mutations were introduced into the secondary-receptor-binding site (SRBS) in FGF23 (M149A/N150A/P151A; FGF23$^{\Delta SRBS}$) and into the corresponding secondary-ligand-binding site (SLBS) in FGFR1c D2 (I203E, FGFR1c$^{\Delta SLBS}$, and V221D, FGFR1c$^{\Delta SLBS'}$), both of which are unique to the 2:2:2:2 quaternary dimer model. The direct receptor-receptor binding site in FGFR1c D2 (A171D; FGFR1c$^{\Delta RRBS}$), another binding site unique to the 2:2:2:2 model, was also mutated (FIG. 13B). While all these FGF23 and FGFR1c mutants were able to form ternary complexes with αKlotho$^{ecto}$, the ternary complexes containing any of the mutated proteins were impaired in their ability to dimerize in the presence of HS6 in solution (FIG. 5F). Moreover, FGF23$^{\Delta SRBS}$ mutant showed a markedly diminished ability to activate FGFR1c in BaF3 cells (FIG. 5E). The loss-of-function effects of these mutations are consistent with a 2:2:2:2 quaternary dimer model (FIG. 13B). Hence, it is posited that HS engages the HS-binding sites of FGFR1c and FGF23 in two stabilized 1:1:1 FGF23-FGFR1c-αKlotho ternary complexes to promote the formation of a two-fold symmetric 2:2:2:2 FGF23-FGFR1c-αKlotho-HS dimer (FIG. 5G). In doing so, HS enhances reciprocal interactions of FGFR1c D2 and FGF23 from one ternary complex with FGFR1c D2 in the other ternary complex, thereby buttressing the dimer (FIG. 13B). This replicates the role that HS plays in paracrine FGF signaling (Schlessinger et al., "Crystal Structure of a Ternary FGF-FGFR-Heparin Complex Reveals a Dual Role for Heparin in FGFR Binding and Dimerization," *Mol. Cell* 6(3):743-750 (2000), which is hereby incorporated by reference in its entirety). In contrast to HS, αKlotho molecules do not directly participate in the dimer interface (FIG. 5G), but rather indirectly support HS-induced dimerization by enhancing 1:1 FGF23-FGFR1c binding affinity. Hence, it appears that FGF23 strikes a fine balance between losing a large amount of HS-binding affinity to enable its endocrine mode of action and retaining sufficient HS-binding affinity to allow HS-mediated dimerization of two 1:1:1 FGF23-FGFR1c-αKlotho complexes. These considerations do not formally exclude the possibility that 2:2:2:2 and 2:2:2:1 quaternary dimers might co-exist as a higher order cluster on the cell surface, as has been proposed for paracrine 2:2:2 and 2:2:1 FGF-FGFR1-HS dimers (Harmer et al., "Towards a Resolution of the Stoichiometry of the Fibroblast Growth Factor (FGF)-FGF Receptor-Heparin Complex," *J. Mol. Biol.* 339(4):821-834 (2004), which is hereby incorporated by reference in its entirety).

FGF19 and FGF21, the other two endocrine FGFs, require βKlotho as an obligate co-receptor to bind and activate cognate FGFRs (Ogawa et al., "BetaKlotho is Required for Metabolic Activity of Fibroblast Growth Factor 21," *PNAS USA* 104(18):7432-7437 (2007) and Kurosu et al., "Tissue-Specific Expression of BetaKlotho and Fibroblast Growth Factor (FGF) Receptor Isoforms Determines Metabolic Activity of FGF19 and FGF21," *J. Biol. Chem.* 282(37):26687-26695 (2007), each of which is hereby incorporated by reference in its entirety) so as to mediate effects that regulate, for example, metabolic pathways involved in bile acid biosynthesis or fatty acid oxidation (Holt et al., "Definition of a Novel Growth Factor-Dependent Signal Cascade for the Suppression of Bile Acid Biosynthesis," *Genes Dev.* 17(13):1581-1591 (2003) and Potthoff et al., "FGF21 Induces PGC-1alpha and Regulates Carbohydrate and Fatty Acid Metabolism During the Adaptive Starvation Response," *PNAS USA Natl* 106(26):10853-10858 (2009), each of which is hereby incorporated by reference in its entirety). Based on the structural analysis and supporting cell-based data shown in FIGS. 14-15, it is hypothesized that βKlotho, similar to αKlotho, functions as a non-enzymatic molecular scaffold to promote signaling by these two FGF hormones.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A modified soluble α-Klotho protein, wherein the modified soluble α-Klotho protein comprises a KL2 extracellular domain comprising a modification to eliminate binding affinity of the modified soluble α-Klotho protein for fibroblast growth factor receptor (FGFR) 1c, FGFR3c, and/or FGFR4, as compared to a wildtype soluble α-Klotho protein, wherein the wildtype soluble α-Klotho protein comprises the amino acid sequence of E34 to S981 of SEQ ID NO: 1, and wherein the modified soluble α-Klotho protein comprises the amino acid sequence of E34 to S932 of SEQ ID NO:2 or E34 to S959 of SEQ ID NO: 7.

2. The modified soluble α-Klotho protein according to claim 1, wherein the modified soluble α-Klotho protein binds fibroblast growth factor (FGF) 23.

3. A pharmaceutical composition comprising the modified soluble α-Klotho protein according to claim 1 and a pharmaceutically acceptable carrier.

4. The modified soluble α-Klotho protein according to claim 1, wherein the modified soluble α-Klotho protein comprises the amino acid sequence of E34 to S932 of SEQ ID NO:2.

5. The modified soluble α-Klotho protein according to claim 1, wherein the modified soluble α-Klotho protein comprises the amino acid sequence of E34 to S959 of SEQ ID NO:7.

6. A modified soluble α-Klotho protein possessing a modification as compared to a wildtype soluble α-Klotho protein, wherein the modified soluble α-Klotho protein comprises the amino acid sequence of E34 to S932 of SEQ ID NO:2 or E34 to S959 of SEQ ID NO:7.

7. The modified soluble α-Klotho protein according to claim 6, wherein the modified soluble α-Klotho protein comprises the amino acid sequence of E34 to S932 of SEQ ID NO:2.

8. The modified soluble α-Klotho protein according to claim 6, wherein the modified soluble α-Klotho protein comprises the amino acid sequence of E34 to S959 of SEQ ID NO:7.

* * * * *